US007011959B1

(12) United States Patent
Santi et al.

(10) Patent No.: US 7,011,959 B1
(45) Date of Patent: Mar. 14, 2006

(54) HETEROLOGOUS PRODUCTION OF POLYKETIDES

(75) Inventors: Daniel Santi, San Francisco, CA (US); Larry Peck, San Carlos, CA (US); Linda Dayem, Belmont, CA (US); James Kealey, San Rafael, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 0 days.

(21) Appl. No.: 09/699,136

(22) Filed: Oct. 27, 2000

Related U.S. Application Data

(60) Provisional application No. 60/161,703, filed on Oct. 27, 1999.

(51) Int. Cl.
*C12P 19/62* (2006.01)

(52) U.S. Cl. .................... 435/76; 435/252.33
(58) Field of Classification Search ........... 435/252.33, 435/76
See application file for complete search history.

(56) References Cited

U.S. PATENT DOCUMENTS

| 5,672,491 | A | 9/1997 | Khosla et al. ............... 435/148 |
| 5,962,290 | A | 10/1999 | Khosla et al. ............... 435/183 |
| 6,033,883 | A | 3/2000 | Barr et al. .................. 435/148 |
| 6,262,340 | B1 * | 7/2001 | Betlach et al. |
| 6,303,342 | B1 * | 10/2001 | Julien et al. |

FOREIGN PATENT DOCUMENTS

| WO | WO 97/13845 | 4/1997 |
| WO | WO 98/49315 | 11/1998 |
| WO | WO 99/02669 | 1/1999 |
| WO | WO 01/27306 | 4/2001 |

OTHER PUBLICATIONS

Tuchman et al. Enhanced Production of Arginine and Urea by Genetically Engineered *Escherichia coli* K-12 Strains. Applied and Environmental Microbiology (1997) 63(1):33-38.*
Gokhale et al. Dissecting and Exploiting Intermodular Communication in Polyketide Synthases. Science (1999) 284:482-485.*
Hunaiti et al. Source of Methylmalonyl-Coenzyme A for Erythromycin Synthesis: Methylmalonyl-Coenzyme A Mutase from Streptomyces erythreus. Antimicrobial Agents and Chemotherapy (1984) 25(2):173-178.*
Wawszkiewicz et al. Propionyl-CoA* Dependent H14CO3-Exchange into Methylmalonyl-CoA in Extracts of Streptomyces erythraeus. Biochemische Zeitschrift (1964) 340:213-227.*
WO 98/27203, WIPO.
WO 99/19518, WIPO.
WO 00/20601, WIPO.
Bramwell et al., Microbiology (1996) 142(3):649-655.
Donadio et al., Molecular Microbiology (1996) 19(5):977-984.
Kao et al., Science (1994) 265(5171):509-512.
Khosla et al., Annual Review of Biochemistry (1999) 68:219-253.
McKie et al., Biochemical Journal (1990) 269(2):293-298.
Pfeifer et al., Science (2001) 291(5509):1790-1792.
Pfeifer et al., Microbiology and Molecular Biology Reviews (2001) 65(1):106-118.
Stassi et al., Proceedings of the National Academy of Sciences of USA (1998) 95(13):7305-7309.
Tang et al., Journal of Bacteriology (1994) 176(19):6107-6119.
Vrijbloed et al., Journal of Bacteriology (1999) 181(18):5600-5605.
Zhang et al., Applied Biochemistry and Biotechnology (1999) 82(3):209-225.
Amaratunga et al., Biochemistry (1996) 35:2453-2463.
Birch et al., J. Bacteriol. (1993) 175:3511-3519.
Francalanci et al., Biochem. J. (1986) 236:489-494.
Haller et al., Biochemistry (2000) 39(16):4622-4629.
Jackson et al., Gene (1995) 167:127-132.
Kealey et al., Proc. Natl. Acad. Sci. USA (1998) 95:505-509.
Leadlay, Biochem. J. (1981) 197:413-419.
Leadlay and Fuller. Biochem. J. (1983) 213:635-642.
Marsh et al., Biochem. J. (1989) 260:345-352.
Redenbach et al., Mol. Microbiol. (1996) 21(1):77-96.
Roberts et al., Eur. J. Biochem. (1993) 214:305-311.
Rodriguez and Gramajo, Microbiology (1999) 145(Pt 11):3109-3119.
Fuller and Leadlay, Biochem. J. (1983) 213:643-650.

* cited by examiner

*Primary Examiner*—Kathleen Kerr
(74) *Attorney, Agent, or Firm*—Gary W. Ashley

(57) ABSTRACT

Recombinant *E. coli* host cells that comprise recombinant DNA expression vectors that drive expression of methylmalonyl CoA mutase from *Propionibacterium shermanii* or *Streptomyces cinnamonensis* as well as *Propionibacterium shermanii* epimerase can produce S-methylmalonyl CoA, a required substrate for the production of polyketides by most modular polyketide synthases and is not present in wild-type *E. coli* host cells.

19 Claims, 9 Drawing Sheets

Biosynthesis of 6-Deoxyerythronolide B (6-dEB), the Aglycone of Erythromycin, by a Modular PKS P= yeast promoter
T= yeast terminator
L1 = BamHI, Not I
L2 = XbaI, EcoRI, SalI, RsrII, AvrII, NsiI, SpeI
L3 = Xho, KpnI

HETEROLOGOUS PRODUCTION OF POLYKETIDES

CROSS-REFERENCE TO RELATED APPLICATIONS

This patent application claims priority to U.S. provisional patent application Ser. No. 60/161,703, filed 27 Oct. 1999, which is incorporated herein by reference.

STATEMENT OF GOVERNMENT INTEREST

This invention was supported in part by SBIR Grant No. GM56575. The United States government has certain rights in this invention.

FIELD OF THE INVENTION

The present invention provides recombinant methods and materials for producing polyketides by recombinant DNA technology. The invention relates to the fields of agriculture, animal husbandry, chemistry, medicinal chemistry, medicine, molecular biology, pharmacology, and veterinary technology.

BACKGROUND OF THE INVENTION

Polyketides represent a large family of diverse compounds synthesized from 2-carbon units through a series of condensations and subsequent modifications. Polyketides occur in many types of organisms, including fungi and mycelial bacteria, in particular, the actinomycetes. There are a wide variety of polyketide structures, and the class of polyketides encompasses numerous compounds with diverse activities. Erythromycin, FK-506, FK-520, megalomicin, narbomycin, oleandomycin, picromycin, rapamycin, spinocyn, and tylosin are examples of such compounds. Given the difficulty in producing polyketide compounds by traditional chemical methodology, and the typically low production of polyketides in wild-type cells, there has been considerable interest in finding improved or alternate means to produce polyketide compounds. See PCT publication Nos. WO 93/13663; WO 95/08548; WO 96/40968; 97/02358; and 98/27203; U.S. Pat. Nos. 4,874,748; 5,063,155; 5,098,837; 5,149,639; 5,672,491; 5,712,146; and 5,962,290; and Fu et al., 1994, Biochemistry 33: 9321–9326; McDaniel et al., 1993, Science 262: 1546–1550; and Rohr, 1995, Angew. Chem. Int. Ed. Engl. 34(8): 881–888, each of which is incorporated herein by reference.

Polyketides are synthesized in nature by polyketide synthase (PKS) enzymes. These enzymes, which are complexes of multiple large proteins, are similar to the synthases that catalyze condensation of 2-carbon units in the biosynthesis of fatty acids. PKS enzymes are encoded by PKS genes that usually consist of three or more open reading frames (ORFs). Two major types of PKS enzymes are known; these differ in their composition and mode of synthesis. These two major types of PKS enzymes are commonly referred to as Type I or "modular" and Type II "iterative" PKS enzymes. A third type of PKS found primarily in fungal cells has features of both the Type I and Type II enzymes and is referred to as a "fungal" PKS enzyme.

Modular PKSs are responsible for producing a large number of 12-, 14-, and 16-membered macrolide antibiotics including erythromycin, megalomicin, methymycin, narbomycin, oleandomycin, picromycin, and tylosin. Each ORF of a modular PKS can comprise one, two, or more "modules" of ketosynthase activity, each module of which consists of at least two (if a loading module) and more typically three (for the simplest extender module) or more enzymatic activities or "domains." These large multifunctional enzymes (>300,000 kDa) catalyze the biosynthesis of polyketide macrolactones through multistep pathways involving decarboxylative condensations between acyl thioesters followed by cycles of varying 3-carbon processing activities (see O'Hagan, D. *The polyketide metabolites; E. Horwood: New York*, 1991, incorporated herein by reference).

During the past half decade, the study of modular PKS function and specificity has been greatly facilitated by the plasmid-based *Streptomyces coelicolor* expression system developed with the 6-deoxyerythronolide B (6-dEB) synthase (DEBS) genes (see Kao et al., 1994, *Science*, 265: 509–512, McDaniel et al., 1993, *Science* 262: 1546–1557, and U.S. Pat. Nos. 5,672,491 and 5,712,146, each of which is incorporated herein by reference). The advantages to this plasmid-based genetic system for DEBS are that it overcomes the tedious and limited techniques for manipulating the natural DEBS host organism, *Saccharopolyspora erythraea*, allows more facile construction of recombinant PKSs, and reduces the complexity of PKS analysis by providing a "clean" host background. This system also expedited construction of the first combinatorial modular polyketide library in *Streptomyces* (see PCT publication Nos. WO 98/49315 and 00/024907, each of which is incorporated herein by reference).

The ability to control aspects of polyketide biosynthesis, such as monomer selection and degree of β-carbon processing, by genetic manipulation of PKSs has stimulated great interest in the combinatorial engineering of novel antibiotics (see Hutchinson, 1998, *Curr. Opin. Microbiol.* 1: 319–329; Carreras and Santi, 1998, *Curr. Opin. Biotech.* 9: 403–411; and U.S. Pat. Nos. 5,712,146 and 5,672,491, each of which is incorporated herein by reference). This interest has resulted in the cloning, analysis, and manipulation by recombinant DNA technology of genes that encode PKS enzymes. The resulting technology allows one to manipulate a known PKS gene cluster either to produce the polyketide synthesized by that PKS at higher levels than occur in nature or in hosts that otherwise do not produce the polyketide. The technology also allows one to produce molecules that are structurally related to, but distinct from, the polyketides produced from known PKS gene clusters.

There has been a great deal of interest in expressing polyketides produced by Type I and Type II PKS enzymes in host cells that do not normally express such enzymes. For example, the production of the fungal polyketide 6-methylsalicylic acid (6-MSA) in heterologous *E. coli*, yeast, and plant cells has been reported. See Kealey et al., January 1998, Production of a polyketide natural product in non-polyketide-producing prokaryotic and eukaryotic host, *Proc. Natl. Acad. Sci. USA* 95:505–9, U.S. Pat. No. 6,033,883, and PCT Patent Publication Nos. 98/27203 and 99/02669, each of which is incorporated herein by reference. Heterologous production of 6-MSA required or was considerably increased by co-expression of a heterologous acyl carrier protein synthase (ACPS) and that, for *E. coli*, media supplements were helpful in increasing the level of the malonyl CoA substrate utilized in 6-MSA biosynthesis. See also, PCT Patent Publication No. 97/13845, incorporated herein by reference.

The biosynthesis of other polyketides requires substrates other than or in addition to malonyl CoA. Such substrates include, for example, propionyl CoA, 2-methylmalonyl CoA, 2-hydroxymalonyl CoA, and 2-ethylmalonyl CoA. Of the myriad host cells possible for utilization as polyketide producing hosts, many do not naturally produce such substrates. Given the potential for making valuable and useful polyketides in large quantities in heterologous host cells, there is a need for host cells capable of making the substrates required for polyketide biosynthesis. The present invention helps meet that need by providing recombinant host cells, expression vectors, and methods for making polyketides in diverse host cells.

SUMMARY OF THE INVENTION

The present invention provides recombinant host cells and expression vectors for making products in host cells that are otherwise unable to make those products due to the lack of a biosynthetic pathway to produce a precursor required for biosynthesis of the product. The present invention also provides methods for increasing the amounts of a product produced in a host cell by providing recombinant biosynthetic pathways for production of a precursor utilized in the biosynthesis of a product.

In one embodiment, the host cell does not produce the precursor, and the host cell is modified by introduction of a recombinant expression vector so that it can produce the precursor. In another embodiment, the precursor is produced in the host cell in small amounts, and the host cell is modified by introduction of a recombinant expression vector so that it can produce the precursor in larger amounts. In a preferred embodiment, the precursor is a primary metabolite that is produced in first cell but not in a second heterologous cell. In accordance with the methods of the invention, the genes that encode the enzymes that produce the primary metabolite in the first cell are transferred to the second cell. The transfer is accomplished using an expression vector of the invention. The expression vector drives expression of the genes and production of the metabolite in the second cell.

In a preferred embodiment, the product is a polyketide. The polyketide is a polyketide synthesized by either a modular, iterative, or fungal PKS. The precursor is selected from the group consisting of malonyl CoA, propionyl CoA, methylmalonyl CoA, ethylmalonyl CoA, and hydroxymalonyl or methoxymalonyl CoA. In an especially preferred embodiment, the polyketide utilizes methylmalonyl CoA in its biosynthesis. In one preferred embodiment, the polyketide is synthesized by a modular PKS that requires methylmalonyl CoA to synthesize the polyketide.

In one embodiment, the host cell is either a procaryotic or eukaryotic host cell. In one embodiment, the host cell is an *E. coli* host cell. In another embodiment, the host cell is a yeast host cell. In another embodiment, the host cell is an Actinomycetes host cell, including but not limited to a *Streptomyces* host cell. In another embodiment, the host cell is a plant host cell. In a preferred embodiment, the host cell is either an *E. coli* or yeast host cell, the product is a polyketide, and the precursor is methylmalonyl CoA.

In one embodiment, the invention provides a recombinant expression vector that comprises a promoter positioned to drive expression of one or more genes that encode the enzymes required for biosynthesis of a precursor. In a preferred embodiment, the promoter is derived from a PKS gene. In a related embodiment, the invention provides recombinant host cells comprising one or more expression vectors that drive expression of the enzymes that produce the precursor.

In another embodiment, the invention provides a recombinant host cell that comprises not only an expression vector of the invention but also an expression vector that comprises a promoter positioned to drive expression of a PKS. In a related embodiment, the invention provides recombinant host cells comprising the vector that produces the PKS and its corresponding polyketide. In a preferred embodiment, the host cell is an *E. coli* or yeast host cell.

These and other embodiments of the invention are described in more detail in the following description, the examples, and claims set forth below.

DETAILED DESCRIPTION OF THE INVENTION

Figure 1:
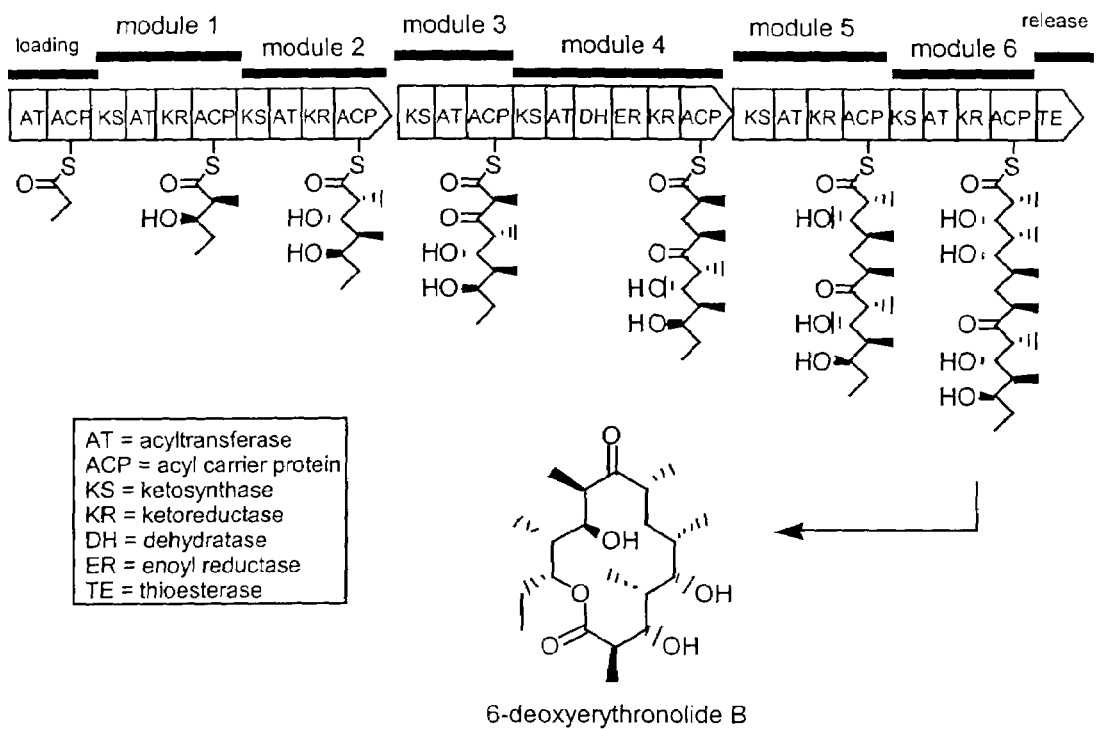
FIG. 1 shows the modules and domains of DEBS and the biosynthesis of 6-dEB from propionyl CoA and methylmalonyl CoA.

The present invention provides recombinant host cells and expression vectors for making products in host cells, which are otherwise unable to make those products due to the lack of a biosynthetic pathway to produce a precursor required for biosynthesis of the product. As used herein, the term recombinant refers to a cell, compound, or composition produced at least in part by human intervention, particularly by modification of the genetic material of a cell. The present invention also provides methods for increasing the amounts of a product produced in a host cell by providing recombinant biosynthetic pathways for production of a precursor utilized in the biosynthesis of a product.

In one embodiment, the host cell does not produce the precursor, and the host cell is modified by introduction of a recombinant expression vector so that it can produce the precursor. In another embodiment, the precursor is produced in the host cell in small amounts, and the host cell is modified by introduction of a recombinant expression vector so that it can produce the precursor in larger amounts. In a preferred embodiment, the precursor is a primary metabolite that is produced in first cell but not in a second heterologous cell. In accordance with the methods of the invention, the genes that encode the enzymes that produce the primary metabolite in the first cell are transferred to the second cell. The transfer is accomplished using an expression vector of the invention. The expression vector drives expression of the genes and production of the metabolite in the second cell.

The invention, in its most general form, concerns the introduction, in whole or in part, of a metabolic pathway from one cell into a heterologous host cell. The invention also encompasses the modification of an existing metabolic pathway, in whole or in part, in a cell, through the introduction of heterologous genetic material into the cell. In all embodiments, the resulting cell is different with regard to its cellular physiology and biochemistry in a manner such that the bio-synthesis, bio-degradation, transport, biochemical modification, or levels of intracellular metabolites allow production or improve expression of desired products. The invention is exemplified by increasing the level of polyketides produced in a heterologous host and by restricting the chemical composition of products to the desired structures.

Thus, in a preferred embodiment, the product produced by the cell is a polyketide. The polyketide is a polyketide synthesized by either a modular, iterative, or fungal PKS. The precursor is selected from the group consisting of malonyl CoA, propionyl CoA, methylmalonyl CoA, ethylmalonyl CoA, and hydroxymalonyl or methoxymalonyl CoA. In an especially preferred embodiment, the polyketide utilizes methylmalonyl CoA in its biosynthesis. In one preferred embodiment, the polyketide is synthesized by a modular PKS that requires methylmalonyl CoA to synthesize the polyketide.

The polyketide class of natural products includes members having diverse structural and pharmacological properties (see Monaghan and Tkacz, 1990, *Annu. Rev. Microbiol.* 44: 271, incorporated herein by reference). Polyketides are assembled by polyketide synthases through successive condensations of activated coenzyme-A thioester monomers derived from small organic acids such as acetate, propionate, and butyrate. Active sites required for condensation include an acyltransferase (AT), acyl carrier protein (ACP), and beta-ketoacylsynthase (KS). Each condensation cycle results in a β-keto group that undergoes all, some, or none of a series of processing activities. Active sites that perform these reactions include a ketoreductase (KR), dehydratase (DH), and enoylreductase (ER). Thus, the absence of any beta-keto processing domain results in the presence of a ketone, a KR alone gives rise to a hydroxyl, a KR and DH result in an alkene, while a KR, DH, and ER combination leads to complete reduction to an alkane. After assembly of the polyketide chain, the molecule typically undergoes cyclization(s) and post-PKS modification (e.g. glycosylation, oxidation, acylation) to achieve the final active compound.

Macrolides such as erythromycin and megalomicin are synthesized by modular PKSs (see Cane et al., 1998, *Science* 282: 63, incorporated herein by reference). For illustrative purposes, the PKS that produces the erythromycin polyketide (6-deoxyerythronolide B synthase or DEBS; see U.S. Pat. No. 5,824,513, incorporated herein by reference) is shown in FIG. 1. DEBS is the most characterized and extensively used modular PKS system. DEBS synthesizes the polyketide 6-deoxyerythronolide B (6-dEB) from propionyl CoA and methylmalonyl CoA. In modular PKS enzymes such as DEBS, the enzymatic steps for each round of condensation and reduction are encoded within a single "module" of the polypeptide (i.e., one distinct module for every condensation cycle). DEBS consists of a loading module and 6 extender modules and a chain terminating thioesterase (TE) domain within three extremely large polypeptides encoded by three open reading frames (ORFs, designated eryAI, eryAII, and eryAIII).

Each of the three polypeptide subunits of DEBS (DEBSI, DEBSII, and DEBSIII) contains 2 extender modules, DEBSI additionally contains the loading module. Collectively, these proteins catalyze the condensation and appropriate reduction of 1 propionyl CoA starter unit and 6 methylmalonyl CoA extender units. Modules 1, 2, 5, and 6 contain KR domains; module 4 contains a complete set, KR/DH/ER, of reductive and dehydratase domains; and module 3 contains no functional reductive domain. Following the condensation and appropriate dehydration and reduction reactions, the enzyme bound intermediate is lactonized by the TE at the end of extender module 6 to form 6-dEB.

More particularly, the loading module of DEBS consists of two domains, an acyl-transferase (AT) domain and an acyl carrier protein (ACP) domain. In other PKS enzymes, the loading module is not composed of an AT and an ACP but instead utilizes a partially inactivated KS, an AT, and an ACP. This partially inactivated KS is in most instances called $KS^Q$, where the superscript letter is the abbreviation for the amino acid, glutamine, that is present instead of the active site cysteine required for full activity. The AT domain of the loading module recognizes a particular acyl CoA (propionyl for DEBS, which can also accept acetyl) and transfers it as a thiol ester to the ACP of the loading module. Concurrently, the AT on each of the extender modules recognizes a particular extender-CoA (methylmalonyl for DEBS) and transfers it to the ACP of that module to form a thioester. Once the PKS is primed with acyl- and malonyl-ACPs, the acyl group of the loading module migrates to form a thiol ester (trans-esterification) at the KS of the first extender module; at this stage, extender module 1 possesses an acyl-KS and a methylmalonyl ACP. The acyl group derived from the loading module is then covalently attached to the alpha-carbon of the malonyl group to form a carbon—carbon bond, driven by concomitant decarboxylation, and generating a new acyl-ACP that has a backbone two carbons longer than the loading unit (elongation or extension). The growing polyketide chain is transferred from the ACP to the KS of the next module, and the process continues.

The polyketide chain, growing by two carbons each module, is sequentially passed as a covalently bound thiol ester from module to module, in an assembly line-like process. The carbon chain produced by this process alone would possess a ketone at every other carbon atom, producing a poyketone, from which the name polyketide arises. Commonly, however, the beta keto group of each two-carbon unit is modified just after it has been added to the growing polyketide chain but before it is transferred to the next module by either a KR, a KR plus a DH, or a KR, a DH, and an ER. As noted above, modules may contain additional enzymatic activities as well.

Once a polyketide chain traverses the final extender module of a PKS, it encounters the releasing domain or thioesterase found at the carboxyl end of most PKSs. Here, the polyketide is cleaved from the enzyme and typically cyclized. The resulting polyketide can be modified further by tailoring or modification enzymes; these enzymes add carbohydrate groups or methyl groups, or make other modifications, i.e., oxidation or reduction, on the polyketide core molecule. For example, the final steps in conversion of 6-dEB to erythromycin A include the actions of a number of modification enzymes, such as: C-6 hydroxylation, attachment of mycarose and desosamine sugars, C-12 hydroxylation (which produces erythromycin C), and conversion of mycarose to cladinose via O-methylation.

With this overview of PKS and post-PKS modification enzymes and their substrates, one can better appreciate the benefits provided by the present invention. DEBS is produced naturally in Saccharopolyspora erythraea and has been transferred to a variety of Streptomyces species, such as S. coelicolor CH999 and S. lividans K4-114 and K4-155, in which it functions without further modification of the host cell to produce 6-dEB. Thus, S. erythraea, S. coelicolor, and S. lividans make the required precursors for 6-dEB synthesis. However, many other non-Saccharopolyspora, non-Streptomyces host cells do not make all of the required precursors or make them only at levels sufficient to support only very small amounts of polyketide biosynthesis.

The present invention provides recombinant DNA expression vectors and methods for making a polyketide and its required precursors in any host cell. In one embodiment, the host cell is either a procaryotic or eukaryotic host cell. In a preferred embodiment, the host cell is an E. coli host cell. In another preferred embodiment, the host cell is a yeast host cell. In another embodiment, the host cell is a plant host cell. In a preferred embodiment, the host cell is either an E. coli or yeast host cell, the product is a polyketide, and the precursor is methylmalonyl CoA.

The recombinant expression vectors of the invention comprise a promoter positioned to drive expression of one or more genes that encode the enzymes required for biosynthesis of a precursor. In a preferred embodiment, the promoter is derived from a PKS gene. In another preferred embodiment, the promoter is one derived from a host cell gene or from a virus or phage that normally infects the host cell and is heterologous to the gene that encodes the biosynthetic enzyme.

In another embodiment, the invention provides a recombinant host cell that comprises not only an expression vector of the invention but also an expression vector that comprises a promoter positioned to drive expression of a PKS. In a related embodiment, the invention provides recombinant host cells comprising the vector that produces the PKS and its corresponding polyketide. In a preferred embodiment, the host cell is an E. coli or yeast host cell.

Neither E. coli nor yeast makes sufficient methylmalonyl CoA to support biosynthesis of large amounts of polyketides that require methylmalonyl CoA in their biosynthesis, and most species do not produce the methylmalonyl CoA substrate at all. In one embodiment, the present invention provides E. coli, yeast, and other host cells that produce methylmalonyl CoA in amounts sufficient to support polyketide biosynthesis. In preferred embodiments, the cells produce sufficient amounts of methylmalonyl CoA to support biosynthesis of polyketides requiring methylmalonyl CoA for their biosynthesis at levels ranging from 1 $\mu$g/L, to 1 mg/L, to 10 mg/L, to 100 mg/L, to 1 g/L, to 10 g/L.

In one embodiment, the host cells of the invention have been modified to express a heterologous methylmalonyl CoA mutase. This enzyme, which converts succinyl CoA to methylmalonyl CoA (although the reverse reaction is 20 times more favored) has been expressed in E. coli using a gene cloned from propionibacteria but was inactive due to the lack of vitamin B12. In accordance with the methods of the present invention, this enzyme can be made in an active form in E. coli and other host cells by either expressing (constitutively or otherwise) a B12 transporter gene, such as the endogenous E. coli gene and/or by utilizing a media that facilitates B12 uptake (as used herein, B12 can refer to the precursor hydroxocobalamin, which is converted to B12). While certain methylmalonyl CoA mutases make the R-isomer, including the methylmalonyl CoA mutases derived from the propionibacteria, the R-isomer can be converted to the S-isomer using an epimerase. For example, epimerase genes from propionibacteria or Streptomyces can be employed for this purpose.

In another embodiment, the host cells of the invention have been modified to express a heterologous propionyl CoA carboxylase that converts propionyl CoA to methylmalonyl CoA. In this embodiment, one can further increase the amount of methylmalonyl CoA precursor by culturing the cells in a media supplemented with propionate. In a preferred embodiment, the host cells are E. coli host cells.

Thus, in accordance with the methods of the invention, the heterologous production of certain polyketides in E. coli, yeast, and other host organisms require both the heterologous expression of a desired PKS and also the enzymes that produce at least some of the substrate molecules required by the PKS. These substrate molecules, called precursors, are not normally found as intracelluar metabolites in the host organism or are present in low abundance. The present invention provides a method to produce or modify the composition or quantities of intracellular metabolites within a host organism where such metabolites are not naturally present or are present in non-optimal amounts.

A specific embodiment of the present invention concerns the introduction and modification of biochemical pathways for methylmalonyl CoA biosynthesis. Methylmalonyl CoA, as noted above, is a substrate utilized for the synthesis of polyketides by many polyketide synthases. Some of the known biochemical pathways for the intracellular production of methylmalonyl CoA employ enzymes and their corresponding genes found in certain organisms. These enzymes and genes have not been found, or are otherwise non-optimal, in other organisms. These other organisms include those that could otherwise be very useful as heterologous hosts for the production of polyketides. The present invention provides methods to engineer a host organism so that it contains a new or modified ability to produce methylmalonyl CoA and/or to increase or decrease the levels of methylmalonyl CoA in the host.

As noted above, two biochemical pathways involving methylmalonyl CoA are particularly relevant to this aspect of the present invention. These pathways are the methylmalonyl CoA mutase pathway, hereafter referred to as the MUT pathway, and the propionyl CoA carboxylase pathway, hereafter referred to as the PCC pathway.

The MUT pathway includes the enzymes methylmalonyl CoA mutase (5.4.99.2, using the numbering system devised by the Nomenclature Committee of the International Union of biochemistry and Molecular Biology), methylmalonyl CoA epimerase (5.1.99.1), and malonyl CoA decarboxylase (4.1.1.9). The biochemical pathway includes the conversion of succinyl CoA to (R)-methylmalonyl CoA through the action of methylmalonyl CoA mutase (5.4.99.2) followed by the conversion of (R)-methylmalonyl CoA to (S)-methylmalonyl CoA through the action of methylmalonyl CoA epimerase (5.1.99.1). (S)-methylmalonyl CoA is a substrate utilized by several polyketide synthases. The enzyme malonyl CoA decarboxylase (4.1.1.9) catalyzes the decarboxylation of malonyl CoA but is also reported to catalyze the decarboxylation of (R)-methylmalonyl CoA to form propionyl CoA. Propionyl CoA is a substrate utilized by some polyketide synthases.

The PCC pathway includes the enzymes propionyl CoA carboxylase (6.4.1.3) and propionyl CoA synthetase (6.2.1.17). The biochemical pathway includes the conversion of propionate to propionyl CoA through the action of propionyl CoA synthetase (6.2.1.17) followed by the conversion of propionyl CoA to (S)-methylmalonyl CoA through the action of propionyl CoA carboxylase (6.4.1.3). (S)-methylmalonyl CoA is the substrate utilized by many polyketide synthases.

An illustrative embodiment of the present invention employs specific enzymes from these pathways. As those skilled in the art will recognize upon contemplation of this description of the invention, the invention can also be practiced using additional and/or alternative enzymes involved in the MUT and PCC pathways. Moreover, the invention can be practiced using additional and alternative pathways for methylmalonyl CoA and other intracelluar metabolites.

The methods of the invention involve the introduction of genetic material into a host strain of choice to modify or alter the cellular physiology and biochemistry of the host. Through the introduction of genetic material, the host strain acquires new properties, e.g. the ability to produce a new, or greater quantities of, an intracellular metabolite. In an illustrative embodiment of the invention, the introduction of genetic material into the host strain results in a new or modified ability to produce methylmalonyl CoA. The genetic material introduced into the host strain contains gene(s), or parts of genes, coding for one or more of the enzymes involved in the bio-synthesis/bio-degradation of methylmalonyl CoA and may also include additional elements for the expression and/or regulation of expression of these genes, e.g. promoter sequences. Specific gene sequences coding for enzymes involved in the bio-synthesis/bio-degradation of methylmalonyl CoA are listed below.

A suitable methylmalonyl CoA mutase (5.4.99.2) gene can be isolated from *Streptomyces cinnamonensis*. See Birch et al., 1993, *J. Bacteriol.* 175: 3511–3519, entitled "Cloning, sequencing, and expression of the gene encoding methylmalonyl-coenzyme A mutase from *Streptomyces cinnamonensis*." This enzyme is a two subunit enzyme; the A and B subunit coding sequences are available under Genbank accession L10064. Another suitable methylmalonyl CoA mutase gene can be isolated from *Propionibacterium shermanii*. See Marsh et al., 1989, *Biochem. J.* 260: 345–352, entitled "Cloning and structural characterization of the genes coding for adenosylcobalamin-dependent methylmalonyl CoA mutase from *Propionibacterium shermanii*." Alternatively, a suitable methylmalonyl CoA mutase gene can be isolated from *Porphyromonas gingivalis*. See Jackson et al., 1995, *Gene* 167: 127–132, entitled "Cloning, expression and sequence analysis of the genes encoding the heterodimeric methylmalonyl CoA mutase of *Porphyromonas gingivalis* W50." Alternatively, suitable methylmalonyl CoA mutase genes can be isolated from any of the sources noted in the following table of a partial BLAST search report or from additional BLAST analyses.

Results of BLAST Search of NCBI Database for Methylmalonyl CoA Mutase mutA gb|L10064|STMMUTA *Streptomyces cinnamonensis* 931 0.0 (query sequence)

gb|AD000015|MSGY175 *Mycobacterium tuberculosis* sequence 300 7e-80 emb|Z79701|MTCY277 *Mycobacterium tuberculosis* H37Rv 300 7e-80 gb|AD000001|MSGY456 *Mycobacterium tuberculosis* sequence 238 8e-76 emb|X14965|PSMUTAB *Propionibacterium shermanii* mutA 268 5e-70 gb|L30136|POYMCMAB *Porphyromonas gingivalis* 137 9e-31 gb|AE000375|AE000375 *Escherichia coli* K-12 MG1655 134 1e-29 gb|U28377|ECU28377 *Escherichia coli* K-12 genome; 134 1e-29 emb|X66836|ECSERAICI *E. coli* serA, iciA, sbm genes 133 1e-29 gb|AF080073 |SMPCAS2 *Sinorhizobium meliloti* 130 2e-28 ref|NM_000255.1|MUT|*Homo sapiens* 113 2e-23 dbj|AP000006|AP000006 *Pyrococcus horikoshii* OT3 110 2e-22 emb|AJ248285.1 |CNSPAX03 *Pyrococcus abyssi* 109 3e-22 emb|X51941|MMMMCOAM Mouse mRNA 109 3e-22 gb|AE000952|AE000952 *Archaeoglobus fulgidus* section 155 104 9e-21 emb|AJ237976.1|SCO237976 *Streptomyces coelicolor* icmA gene 103 2e-20 dbj|AP000062.1 |AP000062 *Aeropyrum pernix* genomic DNA 102 3e-20 gb|U67612|SCU67612 *Streptomyces cinnamonensis* coenzyme B12 98 7e-19 gb|AE001015|AE001015 *Archaeoglobus fulgidus* section 92 97 1e-18 emb|X59424|BFOF4 *Bacillus firmus* OF4 genes for ATP binding 82 7e-14 mutB gb|L10064|STMMUTA *Streptomyces cinnamonensis* 1379 0.0 (query sequence)

gb|AD000001|MSGY456 *Mycobacterium tuberculosis* 1018 0.0 emb|Z79701|MTCY277 *Mycobacterium tuberculosis* H37Rv 1017 0.0 gb|AD000015|MSGY175 *Mycobacterium tuberculosis* sequence 1017 0.0 emb|X14965|PSMUTAB *Propionibacterium shermanii* 996 0.0 gb|L30136|POYMCMAB *Porphyromonas gingivalis* methylmalonyl 882 0.0 ref|NM_000255.1|MUT|*Homo sapiens* methylmalonyl Coenzyme A 855 0.0 emb|X51941|MMMMCOAM Mouse mRNA 32 0.0 gb|U28377|ECU28377 *Escherichia coli* K-12 genome 798 0.0 gb|AE000375|AE000375 *Escherichia coli* K-12 MG1655 798 0.0 emb|X66836|ECSERAICI *E. coli* serA, iciA, sbm genes 797 0.0 gb|AF080073|SMPCAS2 *Sinorhizobium meliloti* 782 0.0 gb|AEO01015|AE001015 *Archaeoglobus fulgidus* 516 e-145 dbj|AP000062.1|AP000062 *Aeropyrum pernix* genomic DNA 408 e-139 emb|AJ248285.1|CNSPAX03 *Pyrococcus abyssi* complete genome 486 e-135 dbj|AP000006|AP000006 *Pyrococcus horikoshii* OT3 genomic DNA 480 e-133 gb|AE000952|AE000952 *Archaeoglobus fulgidus* section 155 467 e-130 emb|Z35604.1|CEZK1058 *Caenorhabditis elegans* cosmid ZK1058 316 e-109
emb|AJ237976.1|SCO237976 *Streptomyces coelicolor* icmA 377 e-103
gb|U67612|SCU67612 *Streptomyces cinnamonensis* coenzyme 372 e-101
emb|AL035161|SC9C7 *Streptomyces coelicolor* cosmid 9C7 359 2e-97
gb|U28335|MEU28335 *Methylobacterium extorquens* 351 4e-95
gb|AF008569|AF008569 *Streptomyces collinus* coenzyme 337 8e-91
gb|U65074|ECU65074 *Escherichia coli* chromosome 275 3e-72
gb|M37500|HUMMUT03 Human methylmalonyl CoA mutase 202 3e-50
gb|AF178673.1|AF178673 *Streptomyces cinnamonensis* 183 1e-44
emb|Z49936.1|CEF13B10 *Caenorhabditis elegans* cosmid F13B10 138 2e-41
gb|M37499|HUMMUT02 Human methylmalonyl CoA mutase 112 4e-23
dbj|AP000001.1 |AP000001 *Pyrococcus horikoshii* OT3 genomic 106 2e-21
emb|AJ248283.1|CNSPAX01 *Pyrococcus abyssi* complete genome 106 2e-21
gb|M37503|HUMMUT06 Human methylmalonyl CoA mutase 101 7e-20
gb|M37508|HUMMUT11 Human methylmalonyl CoA mutase 86 3e-15
gb|M37509|HUMMUT12 Human methylmalonyl CoA mutase 80 3e-13
gb|M37501|HUMMUT04 Human methylmalonyl CoA mutase 77 2e-12

Methylmalonyl CoA mutase requires vitamin B12 (adenosylcobalamin) as an essential cofactor for activity. One of the difficulties in expressing active methylmalonyl CoA mutase in a heterologous host is that the host organism may not provide sufficient, if any, amounts of this cofactor. Work on the expression of methionine synthase, a cobalamin-dependent enzyme, in *E. coli*, a host that does not synthesize cobalamin, has shown that it is possible to express an active cobalamin-dependent enzyme by increasing the rate of cobalamin transport. See Amaratunga et al., 1996, *Biochemistry* 35: 2453–2463, entitled "A synthetic module for the metH gene permits facile mutagenesis of the cobalamin-binding region of *Escherichia coli* methionine synthase: initial characterization of seven mutant proteins," incorporated herein by reference.

The methods of the present invention include the step of increasing the availability of cobalamin for the heterologous expression of active methylmalonyl CoA mutase in certain hosts, e.g. *E. coli*. In particular, these methods incorporate growing cells in a media that contains hydroxocobalamin and/or other nutrients, as described in Amaratunga et al., supra. Additional methods for increasing the availability of cobalamin include constitutive and/or over-expression of vitamin B12 transporter proteins and/or their regulators.

A suitable methylmalonyl CoA epimerase (5.1.99.1) gene for purposes of the present invention can be isolated from *Streptomyces coelicolor* as reported in GenBank locus SC5F2A as gene SC5F2A. 13 (referred to here as EP5) or from *S, coelicolor* as reported in GenBank locus SC6A5 as gene SC6A5.34 (referred to here as EP6). See Redenbach et al., 1996, *Mol. Microbiol.* 21 (1), 77–96, entitled "A set of ordered cosmids and a detailed genetic and physical map for the 8 Mb *Streptomyces coelicolor* A3(2) chromosome," incorporated herein by reference. To date, no biochemical characterization of the proteins encoded by the genes EP5 and EP6 has been carried out; thus, the present invention provides a method for using these genes to provide methylmalonyl CoA epimerase activity to a host. That these genes encode proteins with methylmalonyl CoA epimerase activity is supported by their homology to the sequence of a 2-arylpropionyl CoA epimerase from rat. See Reichel et al., 1997, *Mol. Pharmacol.* 51: 576–582, entitled "Molecular cloning and expression of a 2-arylpropionyl-coenzyme A epimerase: a key enzyme in the inversion metabolism of ibuprofen," and Shieh & Chen, 1993, *J. Biol. Chem.* 268: 3487–3493, entitled "Purification and characterization of novel '2-arylpropionyl CoA epimerases' from rat liver cytosol and mitochondria." Both rat 2-arylpropionyl CoA epimerase and methylmalonyl CoA epimerase catalyze the same stereoisomeric inversion, but with different chemical groups attached.

Biochemical characterization of a methylmalonyl CoA epimerase enzyme purified from *Propionibacterium shermanii* has been completed. See Leadlay, 1981, *Biochem. J.* 197: 413–419, entitled "Purification and characterization of methylmalonyl CoA epimerase from *Propionibacterium shermanii*," Leadlay & Fuller, 1983, *Biochem. J.* 213: 635–642, entitled "Proton transfer in methylmalonyl CoA epimerase from *Propionibacterium shermanii*: Studies with specifically tritiated (2R)-methylmalonyl CoA as substrate; Fuller & Leadlay, 1983, *Biochem. J.* 213: 643–650, entitled "Proton transfer in methylmalonyl CoA epimerase from *Propionibacterium shermanii*: The reaction of (2R)-methylmalonyl CoA in tritiated water." The DNA sequence of the gene coding for this enzyme from *Propionibacterium shermanii* is provided by the present invention as SEQ ID No: 1 in isolated and recombinant form and is incorporated into expression vectors and host cells of the invention. Suitable methylmalonyl CoA epimerase genes can be isolated from a BLAST search using the *P. shermanii* sequence provided in Example 1, below. Preferred epimerases in addition to the *P. shermanii* epimerase include gene identified by homology with the *P. shermanii* sequence located on cosmid 8F4 from the *S. coelicolor* genome sequencing project and the *B. subtilis* epimerase described by Haller et al., 2000, *Biochemistry* 39 (16): 4622–4629, incorporated herein by reference.

One can also make S-methylmalonyl CoA from R-methylmalonyl CoA utilizing an activity of malonyl CoA decarboxylase A, which converts R-methylmalonyl CoA to propionyl CoA. As described above, propionyl CoA can then be converted to S-methylmalonyl CoA by propionyl CoA carboxylase. A suitable malonyl CoA decarboxylase (4.1.1.9) gene for purposes of the present invention can be isolated from *Saccharopolyspora erythraea* as reported in Hsieh & Kolattukudy, 1994, *J. Bacteriol.* 176: 714–724, entitled "Inhibition of erythromycin synthesis by disruption of malonyl-coenzyme A decarboxylase gene eryM in *Saccharopolyspora erythraea*." Alternatively, suitable malonyl CoA decarboxylase genes can be isolated from any of the sources noted in the following table of BLAST search reports or by additional BLAST searches.

Results of BLAST Search of NCBI Database for Malonyl CoA Decarboxylase Malonyl CoA decarboxylase (DC)
gb|L05192|SERMALCOAD *S. erythraea* malonyl 664 0.0 (query sequence)
emb|AL022268|SC4H2 *Streptomyces coelicolor* cosmid 4H2 128 3e-28
emb|Z75555|MTCY02B10 *Mycobacterium tuberculosis* H37Rv 109 1e-22 gb|AD000018|MSGY151 *Mycobacterium tuberculosis* sequence 109 1e-22
gb|AF141323.1|AF141323 *Shigella flexneri* SHI-2 95 5e-18
emb|X76100|ECIUC *E. coli* plasmid iucA, iucB and iucC genes 92 3e-17
emb|AL116808.1|CNS01DGW *Botrytis cinerea* strain T4 cDNA 88 5e-16
gb|AF110737.1|AF110737 *Sinorhizobium meliloti* strain 2011 84 9e-15
emb|AL109846.1|SPBC17G9 *S. pombe* chromosome II cosmid c17G9 71 7e-11
gb|L06163|PSEAAC *Pseudomonas fluorescens* aminoglycoside 70 1e-10

A suitable propionyl CoA carboxylase (6.4.1.3) gene for purposes of the present invention can be isolated from *Streptomyces coelicolor* as reported in GenBank locus AF113605 (pccB), AF113604 (accA2) and AF113603 (accA1) by H. C. Gramajo and colleagues. The propionyl CoA carboxylase gene product requires biotin for activity. If the host cell does not make biotin, then the genes for biotin tranport can be transferred to the host cell. Even if the host cell makes or transports biotin, the endogenous biotin transferase enzyme may not have sufficient activity (whether due to specificity constraints or other reasons) to biotinylate the propionyl CoA carboxylase at the rate required for high level precursor synthesis. In this event, one can simply provide the host cell with a sufficiently active biotin transferase enzyme gene, or if there is an endogenous transferase gene, such as the birA gene in *E. coli*, one can simply overexpress that gene by recombinant methods. Many additional genes coding for propionyl CoA carboxylases, or acetyl CoA carboxylases with relaxed substrate specificity that includes propionate, have been reported and can be used as sources for this gene, as shown in the following table.

Results of BLAST Search of NCBI Database for Propionyl CoA Carboxylase Propionyl CoA Carboxylase (pccB)
gb|AF113605.1|AF113605 *S. coelicolor* propionyl 1035 0.0 (query sequence)
emb|X92557|SEPCCBBCP *S. erythraea* pccB, bcpA2, and orfX 800 0.0
emb|Z92771|MTCY71 *Mycobacterium tuberculosis* H37Rv 691 0.0
dbj|AB018531|AB018531 *Corynebacterium glutamicum* dtsR1 686 0.0
gb|U00012|U00012 *Mycobacterium leprae* cosmid B1308 686 0.0
dbj|AB018530|AB018530 *Corynebacterium glutamicum* dtsR gene 612 e-174
gb|AE001742.1|AE001742 *Thermotoga maritima* section 54 610 e-173
emb|AJ002015|PMAJ2015 *Propionigenium modestum* mmdD 589 e-167
dbj|AB007000|AB007000 *Myxococcus xanthus* MxppcB gene 588 e-166
gb|L48340|MTBKATA *Methylobacterium extorquens* catalase 588 e-166
gb|AE000952|AE000952 *Archaeoglobus fulgidus* section 155 572 e-162
dbj|AP000005|AP000005 *Pyrococcus horikoshii* OT3 genomic 570 e-161
emb|AJ248285.1CNSPAX03 *Pyrococcus abyssi* complete genome 570 e-161
emb|AL031124|SC1C2 *Streptomyces coelicolor* cosmid 1C2 563 e-159
gb|L22208|VEIMCDC *Veillonella parvula* methylmalonyl CoA 558 e-157
gb|AF080235AF080235 *Streptomyces cyanogenus* landomycin 552 e-155
emb|AJ235272|RPXX03 *Rickettsia prowazekii* strain Madrid E 545 e-153
dbj|AB000886|AB000886 *Sus scrofa* mRNA for Propionyl CoA 539 e-152
ref|NM_000532.1|PCCB|*Homo sapiens* propionyl Coenzyme A 538 e-151
emb|X73424|HSPCCBA *Homo sapiens* gene for propionyl CoA 538 e-151
gb|M14634|RATPCCB Rat mitochondrial propionyl CoA 535 e-150
gb|S67325|S67325 propionyl CoA carboxylase beta subunit 531 e-149
gb|U56964|CELF52E4 *Caenorhabditis elegans* cosmid F52E4 367 e-143
emb|Z99116|BSUB0013 *Bacillus subtilis* complete genome 494 e-138
dbj|D84432|BACJH642 *Bacillus subtilis* DNA, 283 Kb region 494 e-138
gb|AF042099|AF042099 *Sulfolobus metallicus* putative 486 e-136
emb|AL022076.1|MTV026 *Mycobacterium tuberculosis* H37Rv 483 e-135
gb|L04196|PRSTRANSC *Propionibacterium shermanii* 383 e-104
emb|AL023635.1|MLCB1243 *Mycobacterium leprae* cosmid B1243 356 1e-96
emb|Z70692.1|MTCY427 *Mycobacterium tuberculosis* H37Rv 353 1e-95
gb|L78825|MSGB1723CS *Mycobacterium leprae* cosmid B1723 DNA 319 4e-93
gb|M95713|RERCOABETA *Rhodococcus erythropolis* 340 5e-92
emb|Z99113|BSUB0010 *Bacillus subtilis* complete genome 325 2e-87
gb|U94697|CCU94697 *Caulobacter crescentus* DNA topoisomerase 270 6e-71
emb|Z95556|MTCY07A7 *Mycobacterium tuberculosis* H37Rv 253 9e-66
emb|Y07660|MTACCBC *M. tuberculosis* accBC gene 231 6e-59
emb|Z79700|MTCY10D7 *Mycobacterium tuberculosis* H37Rv 229 2e-58
dbj|AB018557.1|AB018557 *Streptomyces griseus* cyaA gene 228 5e-58
gb|U46844|MSU46844 *Mycobacterium smegmatis* catalase 209 2e-52
emb|Z19555.1|CEF02A9 *Caenorhabditis elegans* cosmidF02A9 105 9e-51
gb|M13573|HUMPCCB Human propionyl CoA carboxylase beta 194 5e-48
gb|AF030576|AF030576 *Acidaminococcus fermentans* 170 9e-41
emb|Y13917|BSY13917 *Bacillus subtilis* ppsE, yngL, yngK 149 2e-34
emb|X69435|AFGCDA *A. fermentans* GCDA gene for 107 1e-21
emb|Z82368|RPZ82368 *R. prowazekii* genomic DNA fragment 93 2e-17
gb|AF025469|CELW09B6 *Caenorhabditis elegans* cosmid WO9B6 78 5e-13
gb|U87980|MRU87980 *Malonomonas rubra* putative IS-element 78 7e-13
gb|AE001518|AE001518 *Helicobacter pylori*, strain J99 75 6e-12 gb|AE000604.1|AE000604 *Helicobacter pylori* 26695 section 82 75 8e-12
gb|U89347|ACU89347 *Acinetobacter calcoaceticus* malonate 74 1e-11
emb|AL021961|ATF28A23 *Arabidopsis thaliana* DNA 61 2e-11
gb|AE001591|AE001591 *Chlamydia pneumoniae* section 7 73 2e-11
emb|Z46886|UMACCGEN *U. maydis* ACC gene for acetyl coA 71 1e-10
gb|U86128|SSPCCB1 Sus scrofa propionyl CoA carboxylase B 70 2e-10
emb|AJ006497|HSA006497 *Homo sapiens* PCCB gene, exons 11 70 2e-10
gb|AE001301|AE001301 *Chlamydia trachomatis* section 28 69 5e-10
gb|U32724|U32724 *Haemophilus influenzae* Rd section 39 68 8e-10
gb|U04358|PSU04358 *Pseudomonas syringae* pv. syringae Y30 68 8e-10

Propionyl CoA carboxylase (accA2)
gb|AF113604.1|AF113604 *S. coelicolor* putative 1101 0.0 (query sequence)
gb|AF113603.1|AF113603 *Streptomyces coelicolor* putative 1090 0.0
gb|AF126429.1|AF126429 *Streptomyces venezuelae* JadJ 967 0.0
emb|Z92771|MTCY71 *Mycobacterium tuberculosis* H37Rv 758 0.0
emb|X92557|SEPCCBBCP *S. erythraea* pccB, bcpA2, and orfX genes 753 0.0
emb|X92556|SEHGTABCP *S. erythraea* hgtA, bcpA1, and orf122 753 0.0
gb|U00012|U00012 *Mycobacterium leprae* cosmid B1308 746 0.0
emb|X63470|MLBCCPG *M. leprae* gene for biotin carboxyl 743 0.0
gb|U35023|CGU35023 *Corynebacterium glutamicum* thiosulfate 695 0.0
gb|U24659|SVU24659 *Streptomyces venezuelae* glucose 599 e-170
gb|AE000742|AE000742 *Aquifex aeolicus* section 74 413 e-113
gb|U67563|U67563 *Methanococcus jannaschii* section 105 405 e-111
gb|L36530|MQSPYRCARB *Aedes aegypti* pyruvate carboxylase 400 e-110
gb|AF132152.1|AF132152 *Drosophila melanogaster* clone 396 e-108
gb|L09192|MUSMPYR *Mus musculus* pyruvate carboxylase 393 e-107
gb|U36585|RNU36585 *Rattus norvegicus* pyruvate carboxylase 391 e-107
gb|U32314|RNU32314 *Rattus norvegicus* pyruvate carboxylase 391 e-107
gb|L14862|ANAACCC *Anabaena* sp.(PCC7120) 49.1 kDa biotin 388 e-106
gb|U59234|SPU59234 *Synechococcus* PCC7942 biotin 387 e-106
gb|U04641|HSU04641 Human pyruvate carboxylase (PC) mRNA 387 e-106
ref|NM_000920.1|PC|*Homo sapiens* pyruvate carboxylase (PC) 386 e-105
gb|AE00190|AE001090*Archaeoglobus fulgidus* section 17 383 e-104 dbj|D84432|BACJH642 *Bacillus subtilis* DNA, 283 Kb region 382 e-104
emb|Z99116|BSUB0013 *Bacillus subtilis* complete genome 382 e-104
gb|AE000942|AE000942 *Methanobacterium thermoautotrophicum* 382 e-104
gb|S72370|S72370 pyruvate carboxylase human, kidney 380 e-104
dbj|D64001|SYCCPNC *Synechocystis* sp. PCC6803 complete 379 e-103
gb|L14612|PSEACCBC *Pseudomonas aeruginosa* biotin carboxyl 376 e-103
gb|U32778|U32778 *Haemophilus influenzae* Rd section 93 375 e-102
emb|Z36087|SCYBR218C *S. cerevisiae* chromosome II 374 e-102
gb|U35647|SCU35647 *Saccharomyces cerevisiae* pyruvate 374 e-102
gb|J03889|YSCPCB Yeast (*S. cerevisiae*) pyruvate carboxylase 374 e-102
gb|U90879|ATU90879 *Arabidopsis thaliana* biotin carboxylase 374 e-102
emb|Z72584|SCYGL062W *S. cerevisiae* chromosome VII 374 e-102
emb|X59890|SCPYC2G *S. cerivisiae* PYC2 gene for pyruvate 373 e-102
gb|AE000749|AE000749 *Aquifex aeolicus* section 81 371 e-101
gb|AE001286|AE001286 *Chlamydia trachomatis* section 13 370 e-101
gb|AE001604|AE001604 *Chlamydia pneumoniae* section 20 369 e-100
gb|AF007100|AF007100*Glycine max* biotin carboxylase 368 e-100
emb|Z95556|MTCY07A7 *Mycobacterium tuberculosis* H37Rv 367 e-100
emb|Z19549|MTBCARBCP *M. tuberculosis* gene for biotin 367 e-100
gb|AF068249|AF068249 *Glycine max* biotin carboxylase 366 1e-99
gb|L38260|TOBBCSO *Nicotiana tabacum* acetyl CoA 363 7e-99
gb|U36245|BSU36245 *Bacillus subtilis* biotin carboxyl 362 2e-98
gb|AF097728|AF097728 *Aspergillus terreus* pyruvate 361 3e-98
emb|AJ235272|RPXX03 *Rickettsia prowazekii* strain Madrid E 360 1e-97
dbj|D83706|D83706 *Bacillus stearothermophilus* DNA 360 1e-97
gb|AE000744|AE000744 *Aquifex aeolicus* section 76 358 3e-97
emb|AL109846.1|SPBC17G9 *S. pombe* chromosome II 356 1e-96
dbj|D78170|D78170 Yeast DNA for pyruvate carboxylase 353 1e-95
gb|M79446|ECOFABG *Escherichia coli* biotin carboxylase gene 352 2e-95
gb|M83198|ECOFABEGF *Escherichia coli* biotin carboxyl 352 2e-95
gb|AE000404|AE000404 *Escherichia coli* K-12 MG1655 352 2e-95
gb|U18997.1|ECOUW67 *Escherichia coli* K-12 chromosomal 352 2e-95
gb|M80458|ECOACOAC *E. coli* biotin carboxylase and biotin 352 2e-95 gb|U51439|REU51439 *Rhizobium etli* pyruvate carboxylase 351 5e-95 emb|Y03917|BSY13917 *Bacillus subtilis* ppsE, yngL, yngK 348 3e-94 emb|Z99113|BSUB0010*Bacillus subtilis* complete genome 348 3e-94 gb|AE001274.1 |AE 001274 *Leishmania major* chromosome 1 347 6e-94 gb|AF042099|AF042099 *Sulfolobus metallicus* putative 346 1e-93 emb|Z81052.1|CED2023 *Caenorhabditis elegans* cosmid D2023 162 3e-92 emb|Z79700|MTCY10D7 *Mycobacterium tuberculosis* H37Rv 341 4e-92 emb|Z99111 |BSUB0008 *Bacillus subtilis* complete genome 340 1e-91 gb|U12536|ATU12536 *Arabidopsis thaliana* 3-methylcrotonyl 338 4e-91 emb|Y 11106|PPPYC1 *P. pastoris* PYC1 gene 338 4e-91 gb|AE001529|AE001529 *Helicobacter pylori*,strain J99 334 5e-90 gb|AEO00553.1|AEO00553 *Helicobacter pylori* 26695333 7e-90 emb|Y09548|CGPYC *Corynebacterium glutamicum* pyc gene 333 1e-89 gb|AF038548|AF038548 *Corynebacterium glutamicum* pyruvate 333 1e-89 ref|NM_000282.1|PCCA|*Homo sapiens* Propionyl Coenzyme 333 1e-89 gb|M22631|RATPCOA Rat alpha-propionyl CoA carboxylase 332 2e-89 gb|U08469|GMU08469 *Glycine max* 3-methylcrotonyl CoA 328 3e-88 emb|Z83018|MTCY349 *Mycobacterium tuberculosis* H37Rv 318 4e-85 emb|AJ243652.1|PFL243652 *Pseudomonas fluorescens* uahA gene 316 1e-84 emb|Z36077|SCYBR208C *S. cerevisiae* chromosome II 312 2e-83 gb|M64926|YSCUAMD Yeast urea amidolyase (DUR1.2) gene 311 5e-83 emb|Z97025|BSZ97025 *Bacillus subtilis* nprE, yla[A,B,C,D, E,F 300 1e-79 emb|Z81074.1|CEF32B6 *Caenorhabditis elegans* cosmid F32B6 131 7e-78 gb|U00024|MTUO0024 *Mycobacterium tuberculosis* cosmid tbc2 284 7e-75 gb|AD000009|MSGY2 *Mycobacterium tuberculosis* sequence 284 7e-75 gb|U34393|GMU34393 *Glycine max* acetyl CoA carboxylase 259 2e-67 gb|U49829|CELF27D9 *Caenorhabditis elegans* cosmid F27D9 186 4e-59 emb|AJ010111.1|BCE010111 *Bacillus cereus* pycA, ctaA, ctaB 208 5e-52 gb|U19183|ZMU19183 *Zea mays* acetyl-coenzyme A carboxylase 208 5e-52 gb|U10187|TAU10187 *Triticum aestivum* Tam 107 206 2e-51 gb|AF029895|AF029895 *Triticum aestivum* acetyl-coenzyme A 205 5e-51 gb|J03808|RATACACA Rat acetyl-coenzyme A carboxylase mRNA 204 8e-51 emb|X80045|OAACOAC *O. aries* mRNA for acetyl CoA carboxylase 203 1e-50 emb|X68968|HSACOAC *H. sapiens* mRNA for acetyl CoA 203 2e-50 emb|AJ132890.1|BTA132890 *Bos taurus* mRNA for acetyl 202 2e-50 gb|J03541|CHKCOACA Chicken acetyl CoA carboxylase mRNA 202 3e-50 dbj|D34630|ATHACCRNA *Arabidopsis thaliana* mRNA 199 2e-49 gb|L25042|ALFACCASE *Medicago sativa* acetyl CoA carboxylase 198 5e-49 emb|Z71631|SCYNR016C *S. cerevisiae* chromosome XIV 193 2e-47 gb|M92156|YSCFAS3A *Saccharomyces cerevisiae* acetyl CoA 193 2e-47 emb|Z49809|SC8261X *S. cerevisiae* chromosome XIII cosmid 8261 192 3e-47 emb|Z22558|SCHFA1GN *S. cerevisiae* HFA1 gene 192 3e-47 dbj|D78165|D78165 *Saccharomyces cerevisiae* DNA 192 3e-47 emb|Z46886|UMACCGEN *U. maydis* ACC gene for acetyl coa 190 1e-46 ref|NM_001093.1|ACACB|*Homo sapiens* acetyl Coenzyme A 181 5e-44

Propionyl CoA carboxylase (accA1)

gb|AF113603.1|AF113603 *S. coelicolor* putative 1101 0.0 (query sequence)

gb|AF 113604.1|AF113604 *Streptomyces coelicolor* putative 1090 0.0 gb|AF126429.1|AF126429 *Streptomyces venezuelae* JadJ (jadJ) 967 0.0 emb|Z92771|MTCY71 *Mycobacterium tuberculosis* H37Rv 758 0.0 emb|X92557|SEPCCBBCP *S. erythraea* pccB, bcpA2, and orfX genes 753 0.0 emb|X92556|SEHGTABCP *S. erythraea* hgtA, bcpA1, and orf122 753 0.0 gb|U0012|U00012 *Mycobacterium leprae* cosmid B1308 745 0.0 emb|X63470|MLBCCPG *M. leprae* gene for biotin carboxyl 742 0.0 gb|U35023|CGU35023 *Corynebacterium glutamicum* thiosulfate 694 0.0 gb|U24659|SVU24659 *Streptomyces venezuelae* glucose 596 e-169 gb|AE000742|AE000742 *Aquifex aeolicus* section 74 417 e-1 15 gb|U67563|U67563 *Methanococcus jannaschii* section 105 413 e-1 14 gb|L36530|MQSPYRCARB *Aedes aegypti* pyruvate carboxylase 404 e-111 gb|AF132152.1|AF132152 *Drosophila melanogaster* clone 400 e-110 gb|L09192|MUSMPYR *Mus musculus* pyruvate carboxylase 397 e-109 gb|U36585|RNU36585 *Rattus norvegicus* pyruvate carboxylase 395 e-108 gb|U32314|RNU32314 *Rattus norvegicus* pyruvate carboxylase 395 e-108 gb|L14862|ANAACCC *Anabaena* sp. (PCC 7120) 49.1 kDa-biotin 394 e-108 gb|U04641|HSU04641 Human pyruvate carboxylase (PC) mRNA 391 e-107 gb|U59234|SPU59234 *Synechococcus* PCC7942 biotin carboxylase 391 e-107 ref|NM_000920.1|PC|*Homo sapiens* pyruvate carboxylase (PC) 390 e-107 gb|AE001090|AE001090*Archaeoglobus fulgidus* section 17 389 e-106 gb|AE000942|AE000942 *Methanobacterium thermoautotrophicum* 386 e-105
gb|S72370|S72370 pyruvate carboxylase human, kidney 384 e-105
dbj|D84432|BACJH642 *Bacillus subtilis* DNA, 283 Kb region 383 e-105
emb|Z99116|BSUB0013 *Bacillus subtilis* complete genome 383 e-105
dbj|D64001|SYCCPNC *Synechocystis* sp. PCC6803 383 e-104
gb|U35647|SCU35647 *Saccharomyces cerevisiae* pyruvate 382 e-104
emb|Z36087|SCYBR218C *S. cerevisiae* chromosome II 382 e-104
emb|Z72584|SCYGL062W *S. cerevisiae* chromosome VII 381 e-104
gb|J03889|YSCPCB Yeast (*S. cerevisiae*) pyruvate carboxylase 381 e-104
gb|L14612|PSEACCBC *Pseudomonas aeruginosa* biotin carboxyl 381 e-104
emb|X59890|SCPYC2G *S. cerivisiae* PYC2 gene for pyruvate 381 e-104
gb|U32778|U32778 *Haemophilus influenzae* Rd section 93 380 e-104
gb|U90879|ATU90879 *Arabidopsis thaliana* biotin carboxylase 377 e-103
gb|AE000749|AE000749 *Aquifex aeolicus* section 81 of 109 377 e-103
gb|AE001286|AE001286 *Chlamydia trachomatis* section 13 375 e-102
gb|AE001604|AE001604 *Chlamydia pneumoniae* section 20 374 e-102
gb|AF007100|AF07100 *Glycine max* biotin carboxylase 372 e-101
emb|Z95556|MTCY07A7 *Mycobacterium tuberculosis* H37Rv 369 e-100
emb|Z19549|MTBCARBCP *M. tuberculosis* gene for biotin 369 e-100
gb|AF068249|AF068249 *Glycine max* biotin carboxylase 369 e-100
gb|L38260|TOBBCSO *Nicotiana tabacum* acetyl CoA 367 e-100
gb|AF097728|AF097728 *Aspergillus terreus* pyruvate 366 1e-99
gb|AE000744|AE000744 *Aquifex aeolicus* section 76 of 109 364 4e-99
dbj|D83706|D83706 *Bacillus stearothermophilus* DNA 363 7e-99
gb|U36245|BSU36245 *Bacillus subtilis* biotin carboxyl 363 7e-99
emb|AL109846.1|SPBC17G9 *S. pombe* chromosome II 362 2e-98
emb|AJ235272|RPXX03 *Rickettsia prowazekii* strain Madrid E 361 3e-98
dbj|D78170|D78170 Yeast DNA for pyruvate carboxylase 359 2e-97
gb|M80458|ECOACOAC *E. coli* biotin carboxylase and biotin 358 3e-97
gb|M79446|ECOFABG *Escherichia coli* biotin carboxylase gene 358 3e-97
gb|M83198|ECOFABEGF *Escherichia coli* biotin carboxyl 358 3e-97
gb|AE000404|AE000404 *Escherichia coli* K-12 MG1655 358 3e-97
gb|U18997.1|ECOUW67 *Escherichia coli* K-12 chromosomal 358 3e-97
gb|U51439|REU51439 *Rhizobium etli* pyruvate carboxylase 355 3e-96
emb|Y13917|BSY13917 *Bacillus subtilis* ppsE, yngL, yngK, 354 4e-96
emb|Z99113|BSUB0010*Bacillus subtilis* complete genome 354 4e-96
gb|AE001274.1|AE001274 *Leishmania major* chromosome 1 351 3e-95
gb|AF042099|AF042099 *Sulfolobus metallicus* putative 350 9e-95
emb|Z79700|MTCY10D7 *Mycobacterium tuberculosis* H37Rv 347 6e-94
emb|Z81052.1 |CED2023 *Caenorhabditis elegans* cosmid D2023 168 1 e-93
emb|Y 11106|PPPYC1 *P. pastoris* PYC1 gene 345 2e-93
emb|Z99111BSUB0008 *Bacillus subtilis* complete genome 343 8e-93
ref|NM_000282.1|PCCA|*Homo sapiens* Propionyl Coenzyme 340 6e-92
gb|M22631|RATPCOA Rat alpha-propionyl CoA carboxylase 340 1e-91
gb|U12536|ATU12536 *Arabidopsis thaliana* 3-methylcrotonyl 339 2e-91
emb|Y09548|CGPYC *Corynebacterium glutamicum* pyc gene 338 4e-91
gb|AF038548|AF038548 *Corynebacterium glutamicum* pyruvate 338 4e-91
gb|AE001529|AE001529 *Helicobacter pylori*, strain J99 337 8e-91
gb|AE000553.1|AE000553 *Helicobacter pylori* 26695 336 1e-90
gb|U08469|GMU08469 *Glycine max* 3-methylcrotonyl CoA 329 2e-88
emb|AJ243652.1 |PFL243652 *Pseudomonas fluorescens* uahA gene 323 1e-86
emb|Z83018|MTCY349 *Mycobacterium tuberculosis* H37Rv 321 3e-86
emb|Z36077|SCYBR208C *S. cerevisiae* chromosome II 314 5e-84
gb|M64926|YSCUAMD Yeast urea amidolyase (DUR1.2) gene 312 2e-83
emb|Z97025|BSZ97025 *Bacillus subtilis* nprE, yla[A,B,C,D, E, 303 1e-80
emb|Z81074.1 |CEF32B6 *Caenorhabditis elegans* cosmid F32B6 130 1 e-78
gb|U00024|MTU00024 *Mycobacterium tuberculosis* cosmid tbc2 287 6e-76
gb|AD000009|MSGY2 *Mycobacterium tuberculosis* sequence 287 6e-76
gb|U34393|GMU34393 *Glycine max* acetyl CoA carboxylase 262 3e-68
gb|U49829|CELF27D9 *Caenorhabditis elegans* cosmid F27D9 190 2e-61
gb|U10187|TAU10187 *Triticum aestivum* Tam 107 213 2e-53
gb|U19183|ZMU19183 *Zea mays* acetyl-coenzyme A carboxylase 212 3e-53
emb|AJ0101.1|BCE010111 *Bacillus cereus* pycA, ctaA, ctaB 212 4e-53
gb|AF029895|AF029895 *Triticum aestivum* acetyl-coenzyme 209 2e-52
gb|J03808|RATACACA Rat acetyl-coenzyme A carboxylase 205 4e-51
emb|X80045|OAACOAC *O. aries* mRNA for acetyl CoA 205 5e-51
emb|X68968|HSACOAC *H. sapiens* mRNA for acetyl CoA 204 8e-51 dbj|D34630|ATHACCRNA *Arabidopsis thaliana* mRNA 203 1e-50 emb|AJ132890.1|BTA132890 *Bos taurus* mRNA for acetyl CoA 203 1e-50 gb|J03541|CHKCOACA Chicken acetyl CoA carboxylase mRNA 203 1e-50 gb|L25042|ALFACCASE *Medicago sativa* acetyl CoA carboxylase 202 2e-50 emb|Z71631|SCYNR016C *S. cerevisiae* chromosome XIV 196 1e-48 gb|M92156|YSCFAS3A *Saccharomyces cerevisiae* acetyl CoA 196 1e-48 emb|Z49809|SC8261X *S. cerevisiae* chromosome XIII cosmid 8261 195 4e-48 emb|Z22558|SCHFA1GN *S. cerevisiae* HFA1 gene 195 4e-48 dbj|D78165|D78165 *Saccharomyces cerevisiae* DNA 195 4e-48 emb|Z46886|UMACCGEN *U. maydis* ACC gene for acetyl coa 188 5e-46 gb|L20784|CCXACOAC *Cyclotella cryptica* acetyl CoA 182 2e-44

Those of skill in the art will recognize that, due to the degenerate nature of the genetic code, a variety of DNA compounds differing in their nucleotide sequences can be used to encode a given amino acid sequence of the invention. The native DNA sequence encoding the biosynthetic enzymes in the tables above are referenced herein merely to illustrate a preferred embodiment of the invention, and the invention includes DNA compounds of any sequence that encode the amino acid sequences of the polypeptides and proteins of the enzymes utilized in the methods of the invention. In similar fashion, a polypeptide can typically tolerate one or more amino acid substitutions, deletions, and insertions in its amino acid sequence without loss or significant loss of a desired activity. The present invention includes such polypeptides with alternate amino acid sequences, and the amino acid sequences encoded by the DNA sequences shown herein merely illustrate preferred embodiments of the invention.

Thus, in an especially preferred embodiment, the present invention provides DNA molecules in the form of recombinant DNA expression vectors or plasmids, as described in more detail below, that encode one or more precursor biosynthetic enzymes. Generally, such vectors can either replicate in the cytoplasm of the host cell or integrate into the chromosomal DNA of the host cell. In either case, the vector can be a stable vector (i.e., the vector remains present over many cell divisions, even if only with selective pressure) or a transient vector (i.e., the vector is gradually lost by host cells with increasing numbers of cell divisions). The invention provides DNA molecules in isolated (i.e., not pure, but existing in a preparation in an abundance and/or concentration not found in nature) and purified (i.e., substantially free of contaminating materials or substantially free of materials with which the corresponding DNA would be found in nature) form.

In one important embodiment, the invention provides methods for the heterologous expression of one or more of the biosynthetic genes involved in S-methylmalonyl CoA biosynthesis and recombinant DNA expression vectors useful in the method. Thus, included within the scope of the invention are recombinant expression vectors that include such nucleic acids. The term expression vector refers to a nucleic acid that can be introduced into a host cell or cell-free transcription and translation system. An expression vector can be maintained permanently or transiently in a cell, whether as part of the chromosomal or other DNA in the cell or in any cellular compartment, such as a replicating vector in the cytoplasm. An expression vector also comprises a promoter that drives expression of an RNA, which typically is translated into a polypeptide in the cell or cell extract. For efficient translation of RNA into protein, the expression vector also typically contains a ribosome-binding site sequence positioned upstream of the start codon of the coding sequence of the gene to be expressed. Other elements, such as enhancers, secretion signal sequences, transcription termination sequences, and one or more marker genes by which host cells containing the vector can be identified and/or selected, may also be present in an expression vector. Selectable markers, i.e., genes that confer antibiotic resistance or sensitivity, are preferred and confer a selectable phenotype on transformed cells when the cells are grown in an appropriate selective medium.

The various components of an expression vector can vary widely, depending on the intended use of the vector and the host cell(s) in which the vector is intended to replicate or drive expression. Expression vector components suitable for the expression of genes and maintenance of vectors in *E. coli*, yeast, *Streptomyces*, and other commonly used cells are widely known and commercially available. For example, suitable promoters for inclusion in the expression vectors of the invention include those that function in eucaryotic or procaryotic host cells. Promoters can comprise regulatory sequences that allow for regulation of expression relative to the growth of the host cell or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (b/a), bacteriophage lambda PL, and T5 promoters. In addition, synthetic promoters, such as the tac promoter (U.S. Pat. No. 4,551,433), can also be used. For *E. coli* expression vectors, it is useful to include an *E. coli* origin of replication, such as from pUC, p1P, p1I, and pBR.

Thus, recombinant expression vectors contain at least one expression system, which, in turn, is composed of at least a portion of PKS and/or other biosynthetic gene coding sequences operably linked to a promoter and optionally termination sequences that operate to effect expression of the coding sequence in compatible host cells. The host cells are modified by transformation with the recombinant DNA expression vectors of the invention to contain the expression system sequences either as extrachromosomal elements or integrated into the chromosome. The resulting host cells of the invention are useful in methods to produce PKS enzymes as well as polyketides and antibiotics and other useful compounds derived therefrom.

Preferred host cells for purposes of selecting vector components for expression vectors of the present invention include fungal host cells such as yeast and procaryotic host cells such as *E. coli*, but mammalian host cells can also be used. In hosts such as yeasts, plants, or mammalian cells that ordinarily do not produce polyketides, it may be necessary to provide, also typically by recombinant means, suitable holo-ACP synthases to convert the recombinantly produced PKS to functionality. Provision of such enzymes is described, for example, in PCT publication Nos. WO 97/13845 and 98/27203, each of which is incorporated herein by reference.

The recombinant host cells of the invention can express all of the polyketide biosynthetic genes or only a subset of the same. For example, if only the genes for a PKS are expressed in a host cell that otherwise does not produce polyketide modifying enzymes (such as hydroxylation, epoxidation, or glycosylation enzymes) that can act on the polyketide produced, then the host cell produces unmodified polyketides, called macrolide aglycones. Such macrolide aglycones can be hydroxylated and glycosylated by adding them to the fermentation of a strain such as, for example, *Streptomyces antibioticus* or *Saccharopolyspora erythraea*, that contains the requisite modification enzymes.

There are a wide variety of diverse organisms that can modify macrolide aglycones to provide compounds with, or that can be readily modified to have, useful activities. For example, *Saccharopolyspora erythraea* can convert 6-dEB to a variety of useful compounds. The erythronolide 6-dEB is converted by the eryF gene product to erythronolide B, which is, in turn, glycosylated by the eryB gene product to obtain 3-O-mycarosylerythronolide B, which contains L-mycarose at C-3. The enzyme eryC gene product then converts this compound to erythromycin D by glycosylation with D-desosamine at C-5. Erythromycin D, therefore, differs from 6-dEB through glycosylation and by the addition of a hydroxyl group at C-6. Erythromycin D can be converted to erythromycin B in a reaction catalyzed by the eryG gene product by methylating the L-mycarose residue at C-3. Erythromycin D is converted to erythromycin C by the addition of a hydroxyl group at C-12 in a reaction catalyzed by the eryK gene product. Erythromycin A is obtained from erythromycin C by methylation of the mycarose residue in a reaction catalyzed by the eryG gene product. The unmodified polyketides provided by the present invention, such as, for example, 6-dEB produced in *E. coli*, can be provided to cultures of *S. erythraea* and converted to the corresponding derivatives of erythromycins A, B, C, and D in accordance with the procedure provided in the examples below. To ensure that only the desired compound is produced, one can use an *S. erythraea* eryA mutant that is unable to produce 6-dEB but can still carry out the desired conversions (Weber et al., 1985, *J. Bacteriol.* 164(1): 425–433). Also, one can employ other mutant strains, such as eryB, eryC, eryG, and/or eryK mutants, or mutant strains having mutations in multiple genes, to accumulate a preferred compound. The conversion can also be carried out in large fermentors for commercial production.

Moreover, there are other useful organisms that can be employed to hydroxylate and/or glycosylate the compounds of the invention. As described above, the organisms can be mutants unable to produce the polyketide normally produced in that organism, the fermentation can be carried out on plates or in large fermentors, and the compounds produced can be chemically altered after fermentation. Thus, *Streptomyces venezuelae*, which produces picromycin, contains enzymes that can transfer a desosaminyl group to the C-5 hydroxyl and a hydroxyl group to the C-12 position. In addition, *S. venezuelae* contains a glucosylation activity that glucosylates the 2'-hydroxyl group of the desosamine sugar. This latter modification reduces antibiotic activity, but the glucosyl residue is removed by enzymatic action prior to release of the polyketide from the cell. Another organism, *S. narbonensis*, contains the same modification enzymes as *S. venezuelae*, except the C-12 hydroxylase. Thus, the present invention provides the compounds produced by hydroxylation and glycosylation of the macrolide aglycones of the invention by action of the enzymes endogenous to *S. narbonensis* and *S. venezuelae*.

Other organisms suitable for making compounds of the invention include *Micromonospora megalomicea, Streptomyces antibioticus, S. fradiae*, and *S. thermotolerans*. *M. megalomicea* glycosylates the C-3 hydroxyl with mycarose, the C-5 hydroxyl with desosamine, and the C-6 hydroxyl with megosamine, and hydroxylates the C-6 position. *S. antibioticus* produces oleandomycin and contains enzymes that hydroxylate the C-6 and C-12 positions, glycosylate the C-3 hydroxyl with oleandrose and the C-5 hydroxyl with desosamine, and form an epoxide at C-8-C-8a. *S. fradiae* contains enzymes that glycosylate the C-5 hydroxyl with mycaminose and then the 4'-hydroxyl of mycaminose with mycarose, forming a disaccharide. *S. thermotolerans* contains the same activities as *S. fradiae*, as well as acylation activities. Thus, the present invention provides the compounds produced by hydroxylation and glycosylation of the macrolide aglycones of the invention by action of the enzymes endogenous to *M. megalomicea, S. antibioticus, S. fradiae*, and *S. thermotolerans*.

The present invention also provides methods and genetic constructs for producing the glycosylated and/or hydroxylated compounds of the invention directly in the host cell of interest. Thus, the genes that encode polyketide modification enzymes can be included in the host cells of the invention. Lack of adequate resistance to a polyketide can be overcome by providing the host cell with an MLS resistance gene (ermE and mgt/lrm, for example), which confer resistance to several 14-membered macrolides (see Cundliffe, 1989, *Annu. Rev. Microbiol.* 43:207–33; Jenkins and Cundliffe, 1991, *Gene* 108:55–62; and Cundliffe, 1992, *Gene*, 115: 75–84, each of which is incorporated herein by reference).

The recombinant host cells of the invention can be used to produce polyketides (both macrolide aglycones and their modified derivatives) that are naturally occurring or produced by recombinant DNA technology. In one important embodiment, the recombinant host cells of the invention are used to produce hybrid PKS enzymes. For purposes of the invention, a hybrid PKS is a recombinant PKS that comprises all or part of one or more extender modules, loading module, and/or thioesterase/cyclase domain of a first PKS and all or part of one or more extender modules, loading module, and/or thioesterase/cyclase domain of a second PKS.

Those of skill in the art will recognize that all or part of either the first or second PKS in a hybrid PKS of the invention need not be isolated from a naturally occurring source. For example, only a small portion of an AT domain determines its specificity. See PCT patent application No. WO US99/15047 (PCT publication No. WO 00/08138), and Lau et al., infra, incorporated herein by reference. The state of the art in DNA synthesis allows the artisan to construct de novo DNA compounds of size sufficient to construct a useful portion of a PKS module or domain. Thus, the desired derivative coding sequences can be synthesized using standard solid phase synthesis methods such as those described by Jaye et al., 1984, *J. Biol. Chem.* 259: 6331, and instruments for automated synthesis are available commercially from, for example, Applied Biosystems, Inc. For purposes of the invention, such synthetic DNA compounds are deemed to be a portion of a PKS.

A hybrid PKS for purposes of the present invention can result not only:
 (i) from fusions of heterologous domain (where heterologous means the domains in a module are derived from at least two different naturally occurring modules) coding sequences to produce a hybrid module coding sequence contained in a PKS gene whose product is incorporated into a PKS, but also:

(ii) from fusions of heterologous module (where heterologous module means two modules are adjacent to one another that are not adjacent to one another in naturally occurring PKS enzymes) coding sequences to produce a hybrid coding sequence contained in a PKS gene whose product is incorporated into a PKS, (iii) from expression of one or more PKS genes from a first PKS gene cluster with one or more PKS genes from a second PKS gene cluster, and (iv) from combinations of the foregoing.

Various hybrid PKSs of the invention illustrating these various alternatives are described herein.

Recombinant methods for manipulating modular PKS genes to make hybrid PKS enzymes are described in U.S. Pat. Nos. 5,672,491; 5,843,718; 5,830,750; and 5,712,146; and in PCT publication Nos. 98/49315 and 97/02358, each of which is incorporated herein by reference. A number of genetic engineering strategies have been used with DEBS to demonstrate that the structures of polyketides can be manipulated to produce novel natural products, primarily analogs of the erythromycins (see the patent publications referenced supra and Hutchinson, 1998, *Curr Opin Microbiol.* 1:319–329, and Baltz, 1998, *Trends Microbiol.* 6:76–83, incorporated herein by reference).

These techniques include: (i) deletion or insertion of modules to control chain length, (ii) inactivation of reduction/dehydration domains to bypass beta-carbon processing steps, (iii) substitution of AT domains to alter starter and extender units, (iv) addition of reduction/dehydration domains to introduce catalytic activities, and (v) substitution of ketoreductase KR domains to control hydroxyl stereochemistry. In addition, engineered blocked mutants of DEBS have been used for precursor directed biosynthesis of analogs that incorporate synthetically derived starter units. For example, more than 100 novel polyketides were produced by engineering single and combinatorial changes in multiple modules of DEBS. Hybrid PKS enzymes based on DEBS with up to three catalytic domain substitutions were constructed by cassette mutagenesis, in which various DEBS domains were replaced with domains from the rapamycin PKS (see Schweke et al., 1995, *Proc. Nat. Acad. Sci. USA* 92, 7839–7843, incorporated herein by reference) or one more of the DEBS KR domains was deleted. Functional single domain replacements or deletions were combined to generate DEBS enzymes with double and triple catalytic domain substitutions (see McDaniel et al., 1999, *Proc. Nat. Acad. Sci. USA* 96, 1846–1851, incorporated herein by reference).

Methods for generating libraries of polyketides have been greatly improved by cloning PKS genes as a set of three or more mutually selectable plasmids, each carrying a different wild-type or mutant PKS gene, then introducing all possible combinations of the plasmids with wild-type, mutant, and hybrid PKS coding sequences into the same host (see U.S. patent application Ser. No. 60/129,731, filed 16 Apr. 1999, and PCT Pub. No. WO 98/27203, each of which is incorporated herein by reference). This method can also incorporate the use of a KS1° mutant, which by mutational biosynthesis can produce polyketides made from diketide starter units (see Jacobsen et al., 1997, *Science* 277, 367–369, incorporated herein by reference), as well as the use of a truncated gene that leads to 12-membered macrolides or an elongated gene that leads to 16-membered ketolides. Moreover, by utilizing in addition one or more vectors that encode glycosyl biosynthesis and transfer genes, such as those of the present invention for megosamine, desosamine, oleandrose, cladinose, and/or mycarose (in any combination), a large collection of glycosylated polyketides can be prepared.

The following table lists references describing illustrative PKS genes and corresponding enzymes that can be utilized in the construction of the recombinant hybrid PKSs and the corresponding DNA compounds that encode them. Also presented are various references describing tailoring enzymes and corresponding genes that can be employed in accordance with the methods of the invention.

Avermectin
U.S. Pat. No. 5,252,474 to Merck.
MacNeil et al., 1993, *Industrial Microorganisms: Basic and Applied Molecular Genetics*, Baltz, Hegeman, & Skatrud, eds. (ASM), pp. 245–256, A Comparison of the Genes Encoding the Polyketide Synthases for Avermectin, Erythromycin, and Nemadectin.
MacNeil et al., 1992, *Gene* 115: 119–125, Complex Organization of the *Streptomyces avermitilis* genes encoding the avermectin polyketide synthase.

Candicidin (FR008)
Hu et al., 1994, *Mol. Microbiol.* 14: 163–172.

Epothilone
PCT Pat. Pub. No. WO 00/031247 to Kosan.

Erythromcin
PCT Pub. No. 93/13663 to Abbott.
U.S. Pat. No. 5,824,513 to Abbott.
Donadio et al., 1991, *Science* 252:675–9.
Cortes et al., 8 Nov. 1990, *Nature* 348:176–8, An unusually large multifunctional polypeptide in the erythromycin producing polyketide synthase of *Saccharopolyspora erythraea*.

Glycosylation Enzymes
PCT Pat. App. Pub. No. 97/23630 to Abbott.

FK-506
Motamedi et al., 1998, The biosynthetic gene cluster for the macrolactone ring of the immunosuppressant FK506, *Eur. J. biochem.* 256: 528–534.
Motamedi et al., 1997, Structural organization of a multifunctional polyketide synthase involved in the biosynthesis of the macrolide immunosuppressant FK506, *Eur. J. Biochem.* 244: 74–80.

Methyltransferase
U.S. Pat. No. 5,264,355, issued 23 Nov. 1993, Methylating enzyme from *Streptomyces* MA6858. 31-O-desmethyl-FK506 methyltransferase.
Motamedi et. al., 1996, Characterization of methyltransferase and hydroxylase genes involved in the biosynthesis of the immunosuppressants FK506 and FK520, *J. Bacteriol.* 178: 5243–5248.

FK-520
PCT Pat. Pub. No. WO 00/020601 to Kosan.
See also Nielsen et al., 1991, *Biochem.* 30:5789–96 (enzymology of pipecolate incorporation).

Lovastatin
U.S. Pat. No. 5,744,350 to Merck.

Narbomycin (and Picromycin)
PCT Pat. Pub. No. WO 99/61599 to Kosan.

Nemadectin
MacNeil et al., 1993, supra.

Niddamycin

Kakavas et al., 1997, Identification and characterization of the niddamycin polyketide synthase genes from *Streptomyces caelestis*, *J. Bacteriol.* 179: 7515–7522.

Oleandomycin

Swan et al., 1994, Characterisation of a *Streptomyces antibioticus* gene encoding a type I polyketide synthase which has an unusual coding sequence, *Mol. Gen. Genet.* 242: 358–362.

PCT Pat. Pub. No. WO 00/026349 to Kosan.

Olano et al., 1998, Analysis of a *Streptomyces antibioticus* chromosomal region involved in oleandomycin biosynthesis, which encodes two glycosyltransferases responsible for glycosylation of the macrolactone ring, *Mol. Gen. Genet.* 259(3): 299–308.

Platenolide

EP Pat. App. Pub. No. 791,656 to Lilly.

Rapamycin

Schwecke et al., August 1995, The biosynthetic gene cluster for the polyketide rapamycin, *Proc. Natl. Acad. Sci. USA* 92:7839–7843.

Aparicio et al., 1996, Organization of the biosynthetic gene cluster for rapamycin in *Streptomyces hygroscopicus*: analysis of the enzymatic domains in the modular polyketide synthase, *Gene* 169: 9–16.

Rifamycin

August et al., 13 Feb. 1998, Biosynthesis of the ansamycin antibiotic rifamycin: deductions from the molecular analysis of the rifbiosynthetic gene cluster of *Amycolatopsis mediterranei* S669, *Chemistry & Biology*, 5(2): 69–79.

Soraphen

U.S. Pat. No. 5,716,849 to Novartis.

Schupp et al., 1995, *J. Bacteriology* 177: 3673–3679. A *Sorangium cellulosum* (Myxobacterium) Gene Cluster for the Biosynthesis of the Macrolide Antibiotic Soraphen A: Cloning, Characterization, and Homology to Polyketide Synthase Genes from Actinomycetes.

Spiramycin

U.S. Pat. No. 5,098,837 to Lilly.

Activator Gene

U.S. Pat. No. 5,514,544 to Lilly.

Tylosin

EP Pub. No. 791,655 to Lilly.

Kuhstoss et al., 1996, *Gene* 183:231–6., Production of a novel polyketide through the construction of a hybrid polyketide synthase.

U.S. Pat. No. 5,876,991 to Lilly.

Tailoring Enzymes

Merson-Davies and Cundliffe, 1994, *Mol. Microbiol.* 13: 349–355. Analysis of five tylosin biosynthetic genes from the tylBA region of the *Streptomyces fradiae* genome.

As the above Table illustrates, there are a wide variety of PKS genes that serve as readily available sources of DNA and sequence information for use in constructing the hybrid PKS-encoding DNA compounds of the invention.

In constructing hybrid PKSs, certain general methods may be helpful. For example, it is often beneficial to retain the framework of the module to be altered to make the hybrid PKS. Thus, if one desires to add DH and ER functionalities to a module, it is often preferred to replace the KR domain of the original module with a KR, DH, and ER domain-containing segment from another module, instead of merely inserting DH and ER domains. One can alter the stereochemical specificity of a module by replacement of the KS domain with a KS domain from a module that specifies a different stereochemistry. See Lau et al., 1999, "Dissecting the role of acyltransferase domains of modular polyketide synthases in the choice and stereochemical fate of extender units" *Biochemistry* 38(5):1643–1651, incorporated herein by reference. One can alter the specificity of an AT domain by changing only a small segment of the domain. See Lau et al., supra. One can also take advantage of known linker regions in PKS proteins to link modules from two different PKSs to create a hybrid PKS. See Gokhale et al., 16 Apr. 1999, Dissecting and Exploiting Intermodular Communication in Polyketide Synthases", *Science* 284: 482–485, incorporated herein by reference.

The hybrid PKS-encoding DNA compounds can be and often are hybrids of more than two PKS genes. Even where only two genes are used, there are often two or more modules in the hybrid gene in which all or part of the module is derived from a second (or third) PKS gene.

The invention also provides libraries of PKS genes, PKS proteins, and ultimately, of polyketides, that are constructed by generating modifications in a PKS so that the protein complexes produced have altered activities in one or more respects and thus produce polyketides other than the natural product of the PKS. Novel polyketides may thus be prepared, or polyketides in general prepared more readily, using this method. By providing a large number of different genes or gene clusters derived from a naturally occurring PKS gene cluster, each of which has been modified in a different way from the native cluster, an effectively combinatorial library of polyketides can be produced as a result of the multiple variations in these activities. As will be further described below, the metes and bounds of this embodiment of the invention can be described on the polyketide, protein, and the encoding nucleotide sequence levels.

There are at least five degrees of freedom for constructing a hybrid PKS in terms of the polyketide that will be produced. First, the polyketide chain length is determined by the number of extender modules in the PKS, and the present invention includes hybrid PKSs that contain 6, as wells as fewer or more than 6, extender modules. Second, the nature of the carbon skeleton of the PKS is determined by the specificities of the acyl transferases that determine the nature of the extender units at each position, e.g., malonyl, methylmalonyl, ethylmalonyl, or other substituted malonyl. Third, the loading module specificity also has an effect on the resulting carbon skeleton of the polyketide. The loading module may use a different starter unit, such as acetyl, butyryl, and the like. As noted above, another method for varying loading module specificity involves inactivating the KS activity in extender module 1 (KS 1) and providing alternative substrates, called diketides, that are chemically synthesized analogs of extender module 1 diketide products, for extender module 2. This approach was illustrated in PCT publication Nos. 97/02358 and 99/03986, incorporated herein by reference, wherein the KS1 activity was inactivated through mutation. Fourth, the oxidation state at various positions of the polyketide will be determined by the dehydratase and reductase portions of the modules. This will determine the presence and location of ketone and alcohol moieties and C—C double bonds or C—C single bonds in the polyketide. Finally, the stereochemistry of the resulting polyketide is a function of three aspects of the synthase. The first aspect is related to the AT/KS specificity associated with substituted malonyls as extender units, which affects stereochemistry only when the reductive cycle is missing or when it contains only a ketoreductase, as the dehydratase would abolish chirality. Second, the specificity of the ketoreductase may determine the chirality of any beta-OH. Finally, the enoylreductase specificity for substituted malonyls as extender units may influence the stereochemistry when there is a complete KR/DH/ER available.

Thus, the modular PKS systems generally permit a wide range of polyketides to be synthesized. As compared to the aromatic PKS systems, the modular PKS systems accept a wider range of starter units, including aliphatic monomers (acetyl, propionyl, butyryl, isovaleryl, etc.), aromatics (aminohydroxybenzoyl), alicyclics (cyclohexanoyl), and heterocyclics (thiazolyl). Certain modular PKSs have relaxed specificity for their starter units (Kao et al., 1994, Science, supra). Modular PKSs also exhibit considerable variety with regard to the choice of extender units in each condensation cycle. The degree of beta-ketoreduction following a condensation reaction can be altered by genetic manipulation (Donadio et al., 1991, Science, supra; Donadio et al., 1993, Proc. Natl. Acad. Sci. USA 90: 7119–7123). Likewise, the size of the polyketide product can be varied by designing mutants with the appropriate number of modules (Kao et al., 1994, J. Am. Chem. Soc. 116:11612–11613). Lastly, modular PKS enzymes are particularly well known for generating an impressive range of asymmetric centers in their products in a highly controlled manner. The polyketides, antibiotics, and other compounds produced by the methods of the invention are typically single stereoisomeric forms. Although the compounds of the invention can occur as mixtures of stereoisomers, it may be beneficial in some instances to generate individual stereoisomers. Thus, the combinatorial potential within modular PKS pathways based on any naturally occurring modular PKS scaffold is virtually unlimited.

While hybrid PKSs are most often produced by "mixing and matching" portions of PKS coding sequences, mutations in DNA encoding a PKS can also be used to introduce, alter, or delete an activity in the encoded polypeptide. Mutations can be made to the native sequences using conventional techniques. The substrates for mutation can be an entire cluster of genes or only one or two of them; the substrate for mutation may also be portions of one or more of these genes. Techniques for mutation include preparing synthetic oligonucleotides including the mutations and inserting the mutated sequence into the gene encoding a PKS subunit using restriction endonuclease digestion. See, e.g., Kunkel, 1985, Proc. Natl. Acad. Sci. USA 82: 448; Geisselsoder et al., 1987, BioTechniques 5:786. Alternatively, the mutations can be effected using a mismatched primer (generally 10–20 nucleotides in length) that hybridizes to the native nucleotide sequence, at a temperature below the melting temperature of the mismatched duplex. The primer can be made specific by keeping primer length and base composition within relatively narrow limits and by keeping the mutant base centrally located. See Zoller and Smith, 1983, Methods Enzymol. 100:468. Primer extension is effected using DNA polymerase, the product cloned, and clones containing the mutated DNA, derived by segregation of the primer extended strand, selected. Identification can be accomplished using the mutant primer as a hybridization probe. The technique is also applicable for generating multiple point mutations. See, e.g., Dalbie-McFarland et al., 1982, Proc. Natl. Acad. Sci. USA 79: 6409. PCR mutagenesis can also be used to effect the desired mutations.

Random mutagenesis of selected portions of the nucleotide sequences encoding enzymatic activities can also be accomplished by several different techniques known in the art, e.g., by inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants, or by damaging plasmid DNA in vitro with chemicals. Chemical mutagens include, for example, sodium bisulfite, nitrous acid, nitrosoguanidine, hydroxylamine, agents which damage or remove bases thereby preventing normal base-pairing such as hydrazine or formic acid, analogues of nucleotide precursors such as 5-bromouracil, 2-aminopurine, or acridine intercalating agents such as proflavine, acriflavine, quinacrine, and the like. Generally, plasmid DNA or DNA fragments are treated with chemical mutagens, transformed into E. coli and propagated as a pool or library of mutant plasmids.

In constructing a hybrid PKS of the invention, regions encoding enzymatic activity, i.e., regions encoding corresponding activities from different PKS synthases or from different locations in the same PKS, can be recovered, for example, using PCR techniques with appropriate primers. By "corresponding" activity encoding regions is meant those regions encoding the same general type of activity. For example, a KR activity encoded at one location of a gene cluster "corresponds" to a KR encoding activity in another location in the gene cluster or in a different gene cluster. Similarly, a complete reductase cycle could be considered corresponding. For example, KR/DH/ER can correspond to a KR alone.

If replacement of a particular target region in a host PKS is to be made, this replacement can be conducted in vitro using suitable restriction enzymes. The replacement can also be effected in vivo using recombinant techniques involving homologous sequences framing the replacement gene in a donor plasmid and a receptor region in a recipient plasmid. Such systems, advantageously involving plasmids of differing temperature sensitivities are described, for example, in PCT publication No. WO 96/40968, incorporated herein by reference. The vectors used to perform the various operations to replace the enzymatic activity in the host PKS genes or to support mutations in these regions of the host PKS genes can be chosen to contain control sequences operably linked to the resulting coding sequences in a manner such that expression of the coding sequences can be effected in an appropriate host.

However, simple cloning vectors may be used as well. If the cloning vectors employed to obtain PKS genes encoding derived PKS lack control sequences for expression operably linked to the encoding nucleotide sequences, the nucleotide sequences are inserted into appropriate expression vectors. This need not be done individually, but a pool of isolated encoding nucleotide sequences can be inserted into expression vectors, the resulting vectors transformed or transfected into host cells, and the resulting cells plated out into individual colonies. The invention provides a variety of recombinant DNA compounds in which the various coding sequences for the domains and modules of the PKS are flanked by non-naturally occurring restriction enzyme recognition sites.

The various PKS nucleotide sequences can be cloned into one or more recombinant vectors as individual cassettes, with separate control elements, or under the control of, e.g., a single promoter. The PKS subunit encoding regions can include flanking restriction sites to allow for the easy deletion and insertion of other PKS subunit encoding sequences so that hybrid PKSs can be generated. The design of such unique restriction sites is known to those of skill in the art and can be accomplished using the techniques described above, such as site-directed mutagenesis and PCR.

The expression vectors containing nucleotide sequences encoding a variety of PKS enzymes for the production of different polyketides are then transformed into the appropriate host cells to construct the library. In one straightforward approach, a mixture of such vectors is transformed into the selected host cells and the resulting cells plated into individual colonies and selected to identify successful transformants. Each individual colony has the ability to produce a particular PKS synthase and ultimately a particular polyketide. Typically, there will be duplications in some, most, or all of the colonies; the subset of the transformed colonies that contains a different PKS in each member colony can be considered the library. Alternatively, the expression vectors can be used individually to transform hosts, which transformed hosts are then assembled into a library. A variety of strategies are available to obtain a multiplicity of colonies each containing a PKS gene cluster derived from the naturally occurring host gene cluster so that each colony in the library produces a different PKS and ultimately a different polyketide. The number of different polyketides that are produced by the library is typically at least four, more typically at least ten, and preferably at least 20, and more preferably at least 50, reflecting similar numbers of different altered PKS gene clusters and PKS gene products. The number of members in the library is arbitrarily chosen; however, the degrees of freedom outlined above with respect to the variation of starter, extender units, stereochemistry, oxidation state, and chain length enables the production of quite large libraries.

Methods for introducing the recombinant vectors of the invention into suitable hosts are known to those of skill in the art and typically include the use of $CaCl_2$ or agents such as other divalent cations, lipofection, DMSO, protoplast transformation, infection, transfection, and electroporation. The polyketide producing colonies can be identified and isolated using known techniques and the produced polyketides further characterized. The polyketides produced by these colonies can be used collectively in a panel to represent a library or may be assessed individually for activity.

The libraries of the invention can thus be considered at four levels: (1) a multiplicity of colonies each with a different PKS encoding sequence; (2) the proteins produced from the coding sequences; (3) the polyketides produced from the proteins assembled into a function PKS; and (4) antibiotics or compounds with other desired activities derived from the polyketides.

Colonies in the library are induced to produce the relevant synthases and thus to produce the relevant polyketides to obtain a library of polyketides. The polyketides secreted into the media can be screened for binding to desired targets, such as receptors, signaling proteins, and the like. The supernatants per se can be used for screening, or partial or complete purification of the polyketides can first be effected. Typically, such screening methods involve detecting the binding of each member of the library to receptor or other target ligand. Binding can be detected either directly or through a competition assay. Means to screen such libraries for binding are well known in the art. Alternatively, individual polyketide members of the library can be tested against a desired target. In this event, screens wherein the biological response of the target is measured can more readily be included. Antibiotic activity can be verified using typical screening assays such as those set forth in Lehrer et al., 1991, *J. Immunol. Meth.* 13 7:167–173, incorporated herein by reference, and in the Examples below.

The invention provides methods for the preparation of a large number of polyketides. These polyketides are useful intermediates in formation of compounds with antibiotic or other activity through hydroxylation, epoxidation, and glycosylation reactions as described above. In general, the polyketide products of the PKS must be further modified, typically by hydroxylation and glycosylation, to exhibit antibiotic activity. Hydroxylation results in the novel polyketides of the invention that contain hydroxyl groups at C-6, which can be accomplished using the hydroxylase encoded by the eryF gene, and/or C-12, which can be accomplished using the hydroxylase encoded by the picK or eryK gene. Also, the oleP gene is available in recombinant form, which can be used to express the oleP gene product in any host cell. A host cell, such as a *Streptomyces* host cell or a *Saccharopolyspora erythraea* host cell, modified to express the oleP gene thus can be used to produce polyketides comprising the C-8-C-8a epoxide present in oleandomycin. Thus the invention provides such modified polyketides. The presence of hydroxyl groups at these positions can enhance the antibiotic activity of the resulting compound relative to its unhydroxylated counterpart.

Methods for glycosylating the polyketides are generally known in the art; the glycosylation may be effected intracellularly by providing the appropriate glycosylation enzymes or may be effected in vitro using chemical synthetic means as described herein and in PCT publication No. WO 98/49315, incorporated herein by reference. Preferably, glycosylation with desosamine, mycarose, and/or megosamine is effected in accordance with the methods of the invention in recombinant host cells provided by the invention. In general, the approaches to effecting glycosylation mirror those described above with respect to hydroxylation. The purified enzymes, isolated from native sources or recombinantly produced may be used in vitro. Alternatively and as noted, glycosylation may be effected intracellularly using endogenous or recombinantly produced intracellular glycosylases. In addition, synthetic chemical methods may be employed.

The antibiotic modular polyketides may contain any of a number of different sugars, although D-desosamine, or a close analog thereof, is most common. Erythromycin, picromycin, megalomicin, narbomycin, and methymycin contain desosamine. Erythromycin also contains L-cladinose (3-O-methyl mycarose). Tylosin contains mycaminose (4-hydroxy desosamine), mycarose and 6-deoxy-D-allose. 2-acetyl-1-bromodesosamine has been used as a donor to glycosylate polyketides by Masamune et al., 1975, *J. Am. Chem. Soc.* 97: 3512–3513. Other, apparently more stable donors include glycosyl fluorides, thioglycosides, and trichloroacetimidates; see Woodward et al., 1981, *J. Am. Chem. Soc.* 103: 3215; Martin et al., 1997, *J. Am. Chem. Soc.* 119: 3193; Toshima et al., 1995, *J. Am. Chem. Soc.* 117: 3717; Matsumoto et al., 1988, *Tetrahedron Lett.* 29: 3575. Glycosylation can also be effected using the polyketide aglycones as starting materials and using *Saccharopolyspora erythraea* or *Streptomyces venezuelae* or other host cell to make the conversion, preferably using mutants unable to synthesize macrolides, as discussed above.

Thus, a wide variety of polyketides can be produced by the hybrid PKS enzymes of the invention. These polyketides are useful as antibiotics and as intermediates in the synthesis of other useful compounds. In one important aspect, the invention provides methods for making antibiotic compounds related in structure to erythromycin, a potent antibiotic compound. The invention also provides novel ketolide compounds, polyketide compounds with potent antibiotic activity of significant interest due to activity against antibiotic resistant strains of bacteria. See Griesgraber et al., 1996, *J. Antibiot.* 49: 465–477, incorporated herein by reference. Most if not all of the ketolides prepared to date are synthesized using erythromycin A, a derivative of 6-dEB, as an intermediate. See Griesgraber et al., supra; Agouridas et al., 1998, *J. Med. Chem.* 41: 4080–4100, U.S. Pat. Nos. 5,770, 579; 5,760,233; 5,750,510; 5,747,467; 5,747,466; 5,656, 607; 5,635,485; 5,614,614; 5,556,118; 5,543,400; 5,527, 780; 5,444,051; 5,439,890; 5,439,889; and PCT publication Nos. WO 98/09978 and 98/28316, each of which is incorporated herein by reference.

As noted above, the hybrid PKS genes of the invention can be expressed in a host cell that contains the desosamine, megosamine, and/or mycarose biosynthetic genes and corresponding transferase genes as well as the required hydroxylase gene(s), which may be either picK, megK, or eryK (for the C-12 position) and/or megF or eryF (for the C-6 position). The resulting compounds have antibiotic activity but can be further modified, as described in the patent publications referenced above, to yield a desired compound with improved or otherwise desired properties. Alternatively, the aglycone compounds can be produced in the recombinant host cell, and the desired glycosylation and hydroxylation steps carried out in vitro or in vivo, in the latter case by supplying the converting cell with the aglycone, as described above.

As described above, there are a wide variety of diverse organisms that can modify compounds such as those described herein to provide compounds with or that can be readily modified to have useful activities. For example, *Saccharopolyspora erythraea* can convert 6-dEB to a variety of useful compounds. The compounds provided by the present invention can be provided to cultures of *Saccharopolyspora erythraea* and converted to the corresponding derivatives of erythromycins A, B, C, and D in accordance with the procedure provided in the Examples, below. To ensure that only the desired compound is produced, one can use an *S. erythraea* eryA mutant that is unable to produce 6-dEB but can still carry out the desired conversions (Weber et al., 1985, *J. Bacteriol.* 164(1): 425–433). Also, one can employ other mutant strains, such as eryB, eryC, eryG, and/or eryK mutants, or mutant strains having mutations in multiple genes, to accumulate a preferred compound. The conversion can also be carried out in large fermentors for commercial production. Each of the erythromycins A, B, C, and D has antibiotic activity, although erythromycin A has the highest antibiotic activity. Moreover, each of these compounds can form, under treatment with mild acid, a C-6 to C-9 hemiketal with motilide activity. For formation of hemiketals with motilide activity, erythromycins B, C, and D, are preferred, as the presence of a C-12 hydroxyl allows the formation of an inactive compound that has a hemiketal formed between C-9 and C-12.

Thus, the present invention provides the compounds produced by hydroxylation and glycosylation of the compounds of the invention by action of the enzymes endogenous to *Saccharopolyspora erythraea* and mutant strains of *S. erythraea*. Such compounds are useful as antibiotics or as motilides directly or after chemical modification. For use as antibiotics, the compounds of the invention can be used directly without further chemical modification. Erythromycins A, B, C, and D all have antibiotic activity, and the corresponding compounds of the invention that result from the compounds being modified by *Saccharopolyspora erythraea* also have antibiotic activity. These compounds can be chemically modified, however, to provide other compounds of the invention with potent antibiotic activity. For example, alkylation of erythromycin at the C-6 hydroxyl can be used to produce potent antibiotics (clarithromycin is C-6-O-methyl), and other useful modifications are described in, for example, Griesgraber et al., 1996, *J. Antibiot.* 49: 465–477, Agouridas et al., 1998, *J. Med. Chem.* 41: 4080–4100, U.S. Pat. Nos. 5,770,579; 5,760,233; 5,750,510; 5,747,467; 5,747,466; 5,656,607; 5,635,485; 5,614,614; 5,556,118; 5,543,400; 5,527,780; 5,444,051; 5,439,890; and 5,439,889; and PCT publication Nos. WO 98/09978 and 98/28316, each of which is incorporated herein by reference.

For use as motilides, the compounds of the invention can be used directly without further chemical modification. Erythromycin and certain erythromycin analogs are potent agonists of the motilin receptor that can be used clinically as prokinetic agents to induce phase III of migrating motor complexes, to increase esophageal peristalsis and LES pressure in patients with GERD, to accelerate gastric emptying in patients with gastric paresis, and to stimulate gall bladder contractions in patients after gallstone removal and in diabetics with autonomic neuropathy. See Omura et al., 1987, Macrolides with gastrointestinal motor stimulating activity, *J. Med. Chem.* 30: 1941–3). The corresponding compounds of the invention that result from the compounds of the invention being modified by *Saccharopolyspora erythraea* also have motilide activity, particularly after conversion, which can also occur in vivo, to the C-6 to C-9 hemiketal by treatment with mild acid. Compounds lacking the C-12 hydroxyl are especially preferred for use as motilin agonists. These compounds can also be further chemically modified, however, to provide other compounds of the invention with potent motilide activity.

Moreover, and also as noted above, there are other useful organisms that can be employed to hydroxylate and/or glycosylate the compounds of the invention. As described above, the organisms can be mutants unable to produce the polyketide normally produced in that organism, the fermentation can be carried out on plates or in large fermentors, and the compounds produced can be chemically altered after fermentation. In addition to *Saccharopolyspora erythraea, Streptomyces venezuelae, S. narbonensis, S. antibioticus, Micromonospora megalomicea, S. fradiae*, and *S. thermotolerans* can also be used. In addition to antibiotic activity, compounds of the invention produced by treatment with *M. megalomicea* enzymes can have antiparasitic activity as well. Thus, the present invention provides the compounds produced by hydroxylation and glycosylation by action of the enzymes endogenous to *S. erythraea, S. venezuelae, S. narbonensis, S. antibioticus, M. megalomicea, S. fradiae*, and *S. thermotolerans*.

The compounds of the invention can be isolated from the fermentation broths of these cultured cells and purified by standard procedures. The compounds can be readily formulated to provide the pharmaceutical compositions of the invention. The pharmaceutical compositions of the invention can be used in the form of a pharmaceutical preparation, for example, in solid, semisolid, or liquid form. This preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, solutions, emulsions, suspensions, and any other form suitable for use.

The carriers which can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used. For example, the compounds of the invention may be utilized with hydroxypropyl methylcellulose essentially as described in U.S. Pat. No. 4,916,138, incorporated herein by reference, or with a surfactant essentially as described in EPO patent publication No. 428,169, incorporated herein by reference.

Oral dosage forms may be prepared essentially as described by Hondo et al., 1987, *Transplantation Proceedings XIX*, Supp. 6: 17–22, incorporated herein by reference. Dosage forms for external application may be prepared essentially as described in EPO patent publication No. 423,714, incorporated herein by reference. The active compound is included in the pharmaceutical composition in an amount sufficient to produce the desired effect upon the disease process or condition.

For the treatment of conditions and diseases caused by infection, a compound of the invention may be administered orally, topically, parenterally, by inhalation spray, or rectally in dosage unit formulations containing conventional non-toxic pharmaceutically acceptable carriers, adjuvant, and vehicles. The term parenteral, as used herein, includes subcutaneous injections, and intravenous, intramuscular, and intrasternal injection or infusion techniques.

Dosage levels of the compounds of the invention are of the order from about 0.01 mg to about 50 mg per kilogram of body weight per day, preferably from about 0.1 mg to about 10 mg per kilogram of body weight per day. The dosage levels are useful in the treatment of the above-indicated conditions (from about 0.7 mg to about 3.5 mg per patient per day, assuming a 70 kg patient). In addition, the compounds of the invention may be administered on an intermittent basis, i.e., at semi-weekly, weekly, semi-monthly, or monthly intervals.

The amount of active ingredient that may be combined with the carrier materials to produce a single dosage form will vary depending upon the host treated and the particular mode of administration. For example, a formulation intended for oral administration to humans may contain from 0.5 mg to 5 gm of active agent compounded with an appropriate and convenient amount of carrier material, which may vary from about 5 percent to about 95 percent of the total composition. Dosage unit forms will generally contain from about 0.5 mg to about 500 mg of active ingredient. For external administration, the compounds of the invention may be formulated within the range of, for example, 0.00001% to 60% by weight, preferably from 0.001% to 10% by weight, and most preferably from about 0.005% to 0.8% by weight.

It will be understood, however, that the specific dose level for any particlular patient will depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

A detailed description of the invention having been provided above, the following examples are given for the purpose of illustrating the invention and shall not be construed as being a limitation on the scope of the invention or claims.

EXAMPLE 1

Production of Methylmalonyl-CoA in *E. Coli*

This example describes, in part A, the cloning and expression of methylmalonyl-CoA mutase, and in part B, the cloning and expression of methylmalonyl-CoA epimerase, in *E. coli*.

A. Cloning and Expression of Methylmalonyl-CoA Mutase

Methylmalonyl-CoA mutase was cloned from *Propionibacterium shermanii* and expressed in *E. coli*. The holoenzyme mm-CoA mutase was obtained by growing cells in the presence of hydroxocobalamin and was shown to be active without addition of vitamin B12. Methylmalonyl-CoA was produced in vivo, as seen by CoA analysis using a panD strain of BL21 (DE3).

To support modular polyketide production in *E. coli*, the invention provides methods and reagents to produce (S)-methylmalonyl-CoA, which is not naturally present in *E. coli*, by overexpressing mm-CoA mutase and mm-CoA epimerase in *E. coli*. An active, FLAG-tagged version of the mm-CoA mutase from *S. cinnamonensis* was expressed in XL1Blue cells, which were grown in the presence of hydroxocobalamin in a synthetic, vitamin-free media to produce active holoenzyme. The CoA levels in the cells were analyzed by feeding labeled β-alanine; for this purpose it is beneficial to have a panD strain, which is a β-alanine auxotroph. The mutase DNA rearranged in the panD strain of SJ16, a recA$^+$ strain, such that the CoA analysis had to be carried out without the panD. This resulted in a lower signal to noise ratio, but elevated mm-CoA levels could still be detected. As an alternative to the *S. cinnamonensis* genes, the invention provides a mm-CoA mutase from *P. shermanii* cloned into an *E. coli* expression vector, which is active without addition of vitamin B12, and which elevates mm-CoA levels in *E. coli* in a panD strain compatible with the mutase DNA.

*Propionibacterium freudenreichii* subsp. *shermanii* was obtained as a stab in tomato juice agar from derived from a freeze-dried specimen from NCIMB, Scotland (NCIMB # 9885). *E. coli* strain gg3, a panD version of BL21 (DE3) was used for the CoA analysis. *E. coli* strains gg1 and gg2, recA$^-$ versions of the SJ16 panD strain, were also used. The vector pKK** is a version of pKK223-3 in which the cloning region is altered to range from Nde1 to EcoR1 and an extra Nde1 site is deleted. Growth of *P. shermanii* and preparation of genomic DNA was conducted as described in the literature.

Subcloning of methylmalonyl-CoA mutase from *P. shermanii* into *E. coli* was conducted as follows. The gene for mm-CoA mutase consists of two subunits, mutA and mutB, which were amplified by PCR from *P. shermanii* genomic DNA in a total of four fragments. Naturally occurring restriction sites were used to piece the gene together. Unique restriction sites were introduced at both ends of the gene for cloning purposes, and the start codon for the mutB gene was changed from GTG to ATG. As illustrated below, these four fragments were cloned into a Bluescript™ (Stratagene) vector, sequenced, and then pieced together to form the complete mutase gene. The gene was then cloned into expression vectors pET22b and pKK between the restriction sites Nde1 and HindIII, to form pET-MUT and pKK-MUT.

The pET-MUT was transformed into competent cells BL21(DE3) and later into cells gg3, which are apanD version of BL21(DE3). The pKK**-MUT was transformed into SJ16 panD and into XL1Blue. The DNA was tested by screening several colonies with Nde1 and HindIII, to determine if the mutase gene was still present or if it had rearranged.

For SDS-PAGE analysis, cells of strain BL21(DE3) containing pET-MUT (and pET alone, as a control) were grown aerobically at 27° C. in MUT media with 100 μg/ml carbenicillin (carb) (MUT media is M9 salts, glucose, thiamine, trace elements and amino acids, as previously described for the expression of methionine synthase (Amaratunga, M., et al., *A synthetic module for the metHgene permits facile mutagenesis of the cobalamin-binding region of Escherichia coli methionine synthase: initial characterization of seven mutant proteins.* Biochemistry, 1996. 35(7): p. 2453–63). Overnight cultures (250 μl) were used to inoculate 25 mL of MUT media (carb), which were grown at 27° C. to an $OD_{600}$ of approximately 0.5. The cultures were then induced with IPTG to 1 mM final concentration. Two cultures were left at 27° C. for three hours while duplicate cultures were grown at 37° C. for two hours. The cells were collected by centrifugation and the pellets were stored at −80° C. prior to analysis. The cells were lysed by sonication and both the soluble and insoluble phases were examined by SDS/PAGE. This procedure was repeated for cells of strain XL1Blue containing pKK**-MUT.

For expression of active mm-CoA mutase (with hydroxocobalamin), cells of strain gg3 containing pET-MUT (and pET alone, as a control) were grown in MUT media (carb) and 5 μM beta-alanine for approximately 20 hours at 27° C. The following operations were performed in a dark room with a red safelight: 125-mL flasks, each containing 25 mL of MUT media with carb and 5 μM β-alanine and wrapped in aluminum foil, were inoculated with 5 μM hydroxocobalamin and then with 250 μL from the respective starter cultures. After shaking overnight at 27° C., the cultures were induced with IPTG to 1 mM final concentration and grown for an additional 4–45 hours, at which point they were collected (in Falcon tubes wrapped in aluminum foil) by centrifugation at 4000 rpm for 10 minutes. The pellets were stored in the dark at −80° C. prior to assaying.

The mutase assay was performed as follows. All operations were performed in the dark or under a red safelight. The pellet from 25 mL of culture was thawed, washed in buffer C (50 mM potassium phosphate pH 7.4, 5 mM EDTA, 10% glycerol), and resuspended in 0.5 mL of buffer C containing protease inhibitors (1 tablet per 10 mL of buffer). Following sonication on ice, the extract was clarified by centrifugation at 4° C. for 10 minutes at maximum speed in an Eppendorf microfuge; the supernatent was assayed. Enzyme assays contained, in a final volume of 100 μL, 0.2 mM (2R,2S)-methylmalonyl-CoA, mutase extract, and buffer C containing protease inhibitors. Reactions for assays with vitamin B12 were as above but contained 0.01 mM vitamin B12, in which case the mutase extract was incubated with the vitamin B12 in a total volume of 75 μL for 5 minutes at 30° C. prior to initiation of reaction with methylmalonyl-CoA. After the desired length of incubation at 30° C., the reaction was stopped by the addition of 50 μL of 10% trichloroacetic acid (TCA) and placed on ice for approximately 10 minutes. Cellular debris and precipitated protein were removed by centrifugation for 5 minutes in an Eppendorf microfuge at 4° C. An aliquot (100 μL) of the supernatant was injected onto the HPLC to quantify conversion of methylmalonyl-CoA to succinyl-CoA. One time point was taken after 20 minutes of incubation at 30° C., and the sample was assayed for conversion of mm-CoA to succinyl-CoA. All operations were performed exclusively under a red safelight until the reaction was stopped by addition of TCA.

The CoA analysis was performed as described in the literature, except that 5 μM of hydroxocobalamin were added at the time of IPTG induction, and the tubes were wrapped in aluminum foil and grown at 27° C. instead of 30° C. The CoA peaks, which eluted in approximately one minute each, were collected manually, as well as approximately one minute of sample both before and after each peak. In some tests, fractions were collected every 30 seconds. All samples were counted in the scintillation counter.

The two subunits of the gene encoding methylmalonyl-CoA mutase are translationally coupled—the GTG start codon of the downstream subunit mutB overlaps with the ATG codon of mutA. The GTG valine start was mutated to an ATG methionine start (which does not alter any other amino acids), because *E. coli* utilizes the methionine start more efficiently. Sequencing the mm-CoA mutase gene revealed a discrepancy between the sequence observed and the published sequence. A "GC" instead of a "CG" changed two amino acids from Asp, Val to Glu, Leu. The crystal structure of mm-CoA mutase from *P. shermanii* showed that the two amino acids are indeed Glu, Leu, so the published sequence is in error. The mm-CoA mutase gene was subcloned into two different *E. coli* expression systems: pET, which is under control of the strong T7 promoter, and pKK, which uses the leaky tac promoter. First it was necessary to find strains in which the mutase DNA did not rearrange. It was previously observed that a FLAG-tagged version of the mutase from *S. cinnamonensis* rearranged in SJ 16 panD and in BL21(DE3), which are both recA⁺ strains, but not in XL1Blue, which is recA⁻. This mutase DNA (*P. shermanii*) also rearranged in the SJ16 cells but not in the BL21(DE3) cells. Thus a panD version of BL21 (DE3) was created (gg3) for use with the pET vector. A recA⁻ version of SJ16 was also created (gg1, gg2) for use with the pKK system; however, the mutase DNA rearranged in this strain as well.

Different growth conditions were tested to find conditions in which the two subunits of the mutase were expressed in the soluble phase in approximately equal molar ratios. In general, it seemed that the higher temperature of 37° C. caused the mutase to appear predominantly in the insoluble form. Growth exclusively at 27° C. resulted in soluble protein with an approximately equal subunit ratio.

Figure 3:
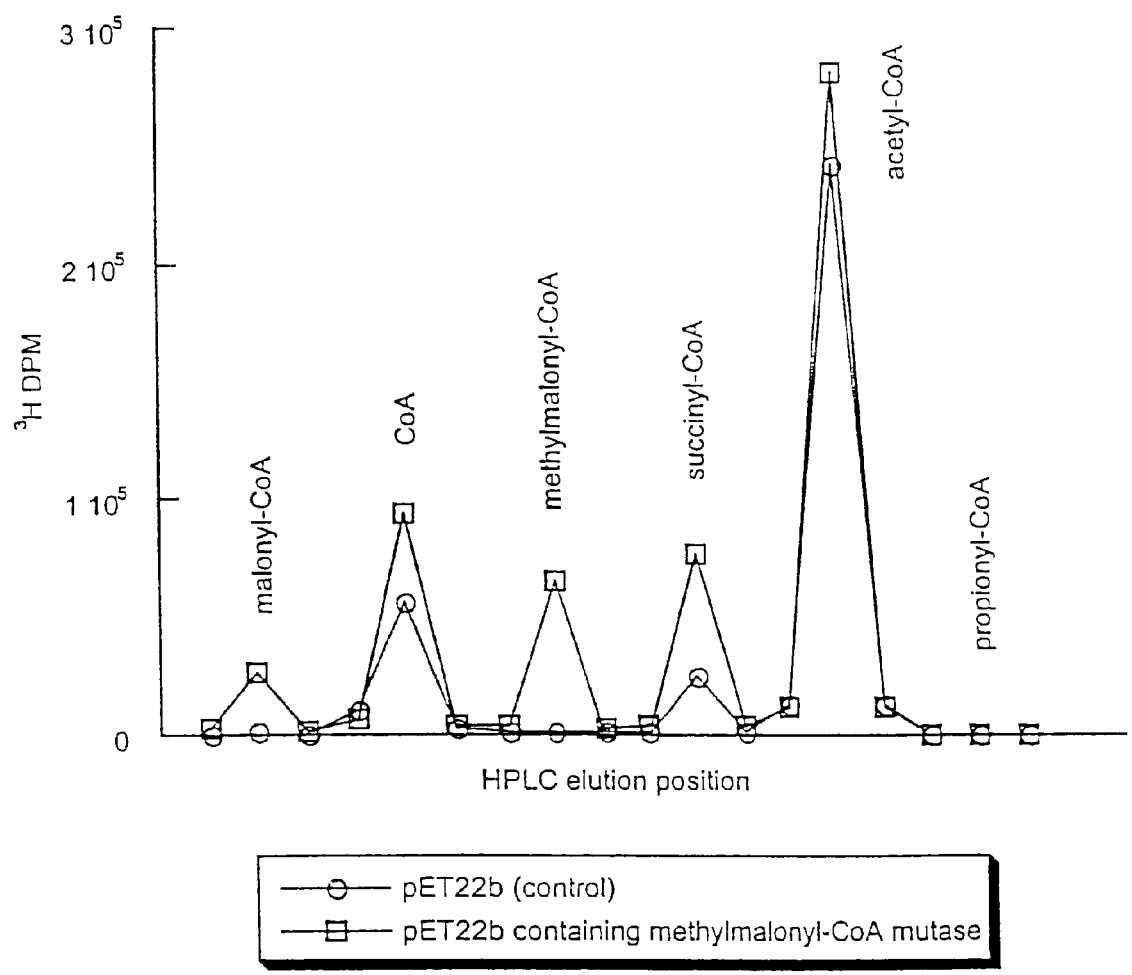
FIG. 3 shows the acyl-CoA analysis in BL21(DE3) panD strains in vivo.

FIG. 3 shows the comparison of in vivo acyl-CoA levels in BL21(DE3) panDstrains with and without mm-CoA mutase. For each CoA, the ratio of the amount in the strain containing the mutase to the amount in the control strain was determined. Interestingly, malonyl-CoA was increased about 25-fold and succinyl-CoA about 3-fold. Acetyl-CoA and CoA were increased just slightly, and propionyl-CoA was not detected in either case.

To express active mutase in vivo, it was necessary to grow cells in a defined media (MUT media) that allows uptake of the vitamin B12 precursor hydroxocobalamin; this is similar to an established protocol for expression of active methionine synthase, which also requires B12. Cell extracts overexpressing the mutase were shown to convert mm-CoA to succinyl CoA without the addition of vitamin B12. Only one time point (at 20 minutes) was assayed to confirm activity; the specific activity of the mutase was not determined.

Thus, methylmalonyl-CoA mutase was expressed as the active holoenzyme in *E. coli*, and methylmalonyl-CoA was produced in vivo. Because a slow, spontaneous chemical epimerization between (R)- and (S)-mm-CoA does exist (approximately 3% in 15 minutes), it may be helpful to determine the relative amounts of these diastereomers in cells overexpressing the mutase. Enough (S)-mm-CoA may be present to support polyketide production in some cells without addition of an epimerase. To facilitate the eventual production of polyketides in E. coli, the mutase gene can be incorporated into the chromosome of the BL21 panD cell or other host cell.

Figure 2:
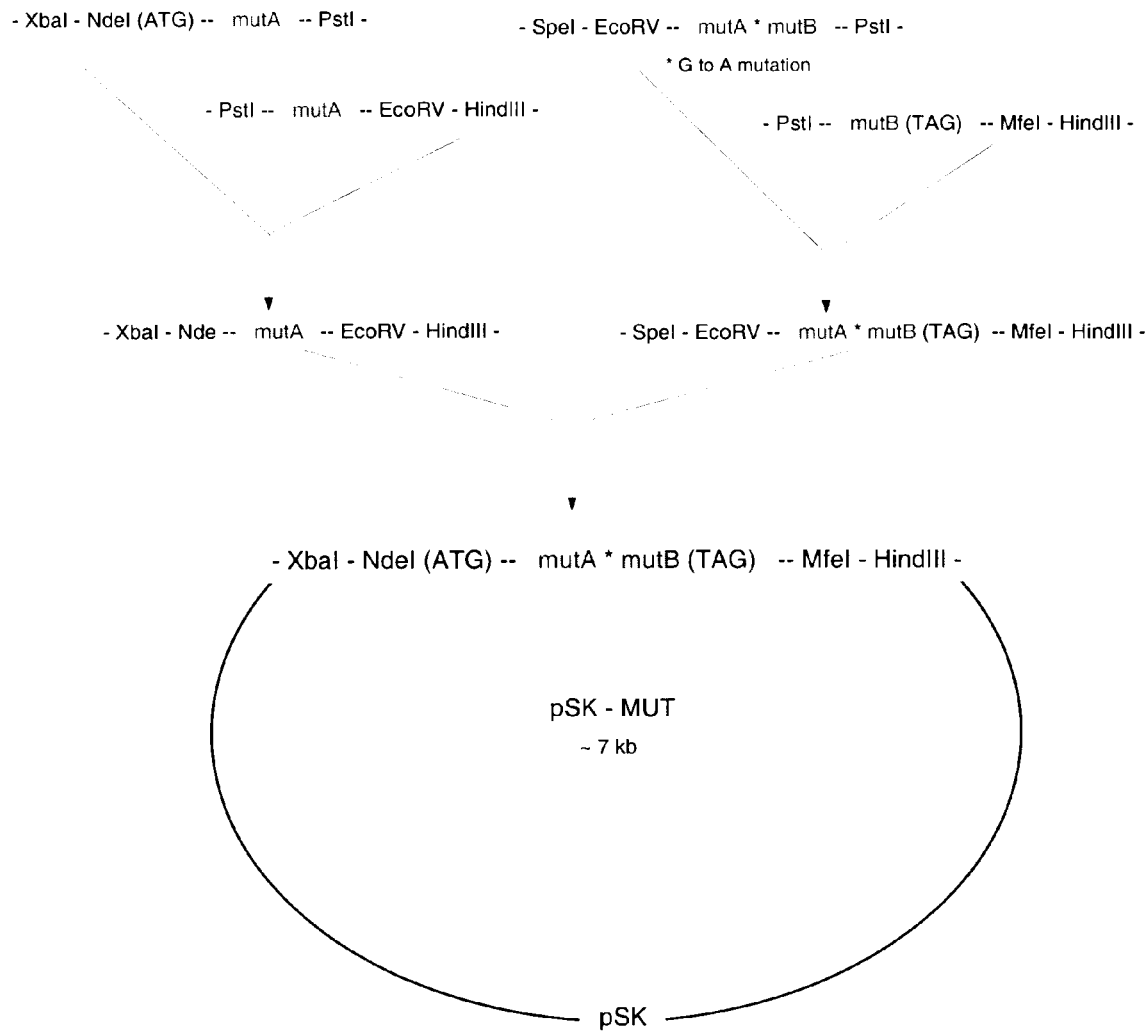
FIG. 2 shows the construction of pSK-MUT, in which four PCR fragments were sequenced and pieced together to form the complete mutase gene in pSK-bluescript.

FIG. 2 shows the construction of pSK-MUT, in which four PCR fragments were sequenced and pieced together to form the complete mutase gene in pSK-bluescript.

In follow-up experiments, the specific activity of the mutase was determined and an in-depth CoA analysis was completed. As shown in FIG. 3, the CoA levels in the cells were again analyzed using a panD strain, which is a β-alanine auxotroph. $^3$H-β-alanine was fed to the cells and incorporated into the acyl-CoAs, which were separated via HPLC and counted. The CoA pools for cell extracts with and without the mutase, as well as with and without hydroxocobalamin, were examined.

To test whether acyl-CoAs degrade in TCA, the following tests were conducted. The CoA mix consisted of 1.6 mM each of malonyl-, methylmalonyl-, succinyl-, acetyl-, and propionyl-CoA, plus 0.5 mM CoA. An aliquot (10 μL) of this mix was added to 100 μL 10% TCA, 50 μL were immediately injected to the HPLC for CoA analysis, and the remainder was promptly frozen on dry ice. The frozen portion was then thawed and loaded immediately to the HPLC. Again, 10 μL of the CoA mix were added to 100 μL 10% TCA, 50 μL were left on ice for 15 minutes and then injected to the HPLC, the remainder was left at 4° C. overnight and injected to the HPLC the next morning. The area under each CoA peak was noted. This same procedure was followed but using a mixture of TCA and buffer A from the mutase assay.

The CoA analysis described here is carried out on cells which are lysed in 10% TCA. Thus, determining whether the CoAs degrade significantly in TCA and in a mixture of TCA and buffer A from the mutase assay is important. The tests showed that the percent of each CoA relative to the total CoA pool, as well as the overall amount of CoA, remained constant after freeze/thawing, after leaving on ice for 15 minutes, and after leaving the sample overnight at 4° C. Thus, the CoAs are stable in TCA and in the mutase assay buffer after the cells are lysed or after the assays are completed, and prior to HPLC analysis.

Although the CoAs are stable in TCA and buffer at 4° C., they degraded at 30° C., the temperature at which the mutase assay was performed. In five minutes under the assay conditions, about 4% of the methylmalonyl-CoA hydrolyzed to CoA. The succinyl-CoA hydrolyzed at a comparable rate. Thus, the mutase assay is suboptimal for extremely quantitative results.

When 0.2 mM methylmalonyl-CoA was incubated with a crude lysate from cell extracts overexpressing the mutase, succinyl-CoA was produced. No succinyl-CoA was observed when methylmalonyl-CoA was incubated with lysates from the control strain (containing the plasmid vector but lacking the mutase genes). Under these expression and assay conditions, a specific activity of approximately 0.04 U/mg was observed in the crude extracts. When cells overexpressing the mutase were grown in MUT media without hydroxocobalamin, no mutase activity was observed; however, mutase activity could be detected by addition of vitamin B12 in vitro. Adding vitamin B12 to extracts that were grown in the presence of hydroxocobalamin resulted in increased mutase activity, suggesting that a significant amount of expressed mutase is present as the apo-enzyme. This might have occurred because the enzyme was expressed faster than the hydroxocobalamin could be transported into the cell, or because the vitamin B12 cofactor was lost during preparation of the extract.

Figure 4:
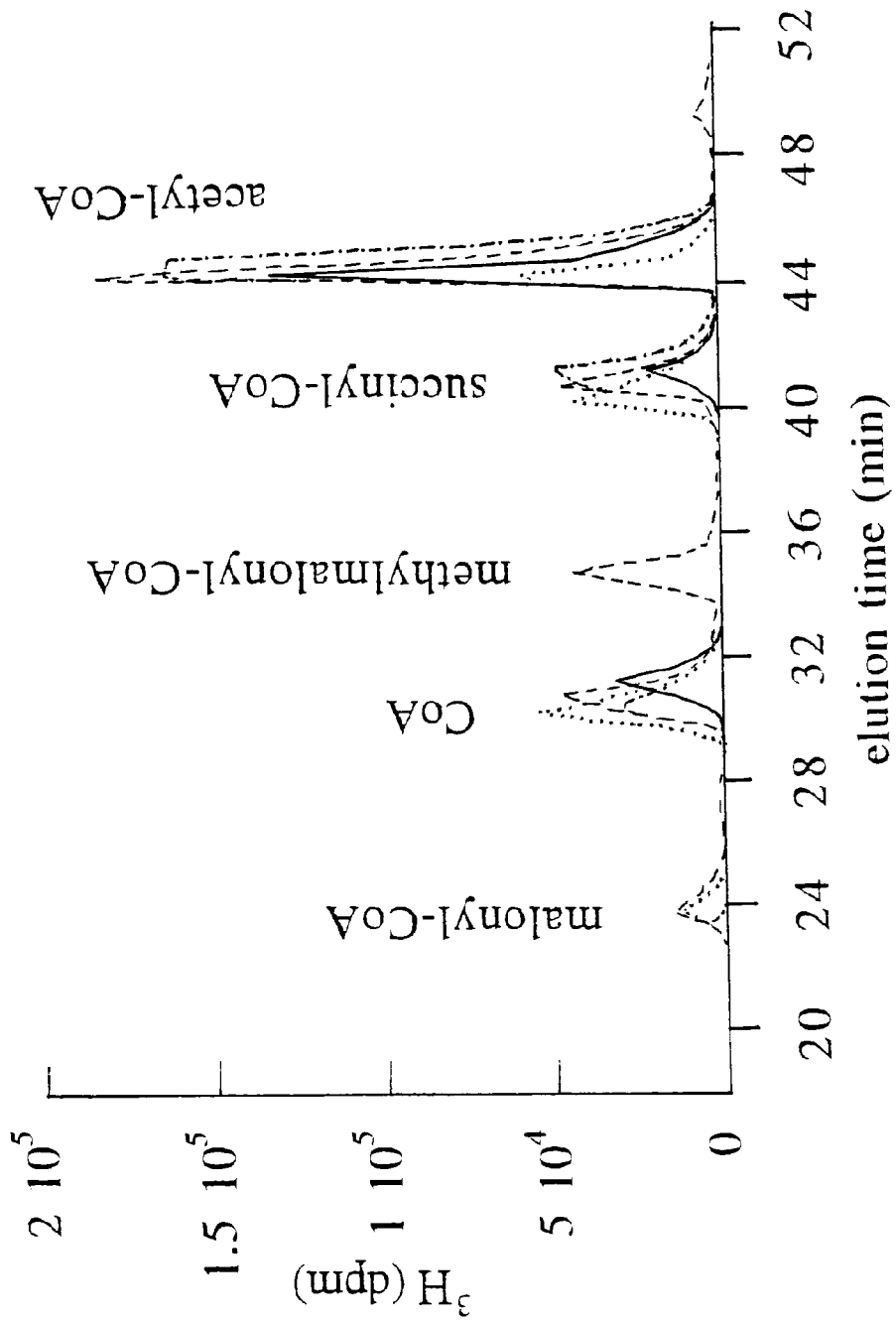
FIG. 4 shows the results of CoA analysis of *E. coli* overexpressing methylmalonyl-CoA mutase. The levels of $^3$H detected in fractions collected from HPLC of cell-free extracts from $^3$H_-alanine-fed *E. coli* harboring either the pET control vector grown without hydroxocobalamin (solid trace), pET grown with hydroxocobalamin (dash-dotted trace), pET overexpressing the mutase and grown without hydroxocobalamin (dotted trace), or pET overexpressing the mutase and grown with hydroxocobalamin (dashed trace) are shown.

FIG. 4 shows the comparison of in vivo acyl-CoA levels with and without the mutase and with and without hydroxocobalamin. In the cells overexpressing the mutase and grown with hydroxocobalamin, methylmalonyl-CoA comprised 13% of the overall CoA pool, whereas in the other cells no methylmalonyl-CoA was detectable. The background level of counts is about 0.25% of the overall number of counts in the CoAs, suggesting that any methymalonyl-CoA present in E. coli strains not overexpressing the mutase would comprise at most 0.25% of the overall CoA pool, or 2% of the amount of methylmalonyl-CoA observed in the strain overexpressing the mutase. The composition of the CoA pool observed for the E. coli panD strain is consistent with that observed previously for E. coli panD mutants grown on glucose.

Thus, the methylmalonyl-CoA mutase from P. shermanii has been overexpressed as the active holoenzyme in E. coli and shown to produce (2R)-methylmalonyl-CoA in vivo. Conversion of (2R)- to (2S)-methylmalonyl-CoA via methylmalonyl-CoA epimerase should provide an adequate supply of the correct isomer of methylmalonyl-CoA to support heterologous production of complex polyketides E. coli.

FIG. 4 shows the results of CoA analysis of E. coli overexpressing methylmalonyl-CoA mutase. The levels of $^3$H detected in fractions collected from HPLC of cell-free extracts from $^3$β-alanine-fed E. coli harboring either the pET control vector grown without hydroxocobalamin (solid line), pET grown with hydroxocobalamin (dash-dotted), pET overexpressing the mutase and grown without hydroxocobalamin (dotted), or pET overexpressing the mutase and grown with hydroxocobalamin (dashed) are shown.

B. Cloning and Expression of Methylmalonyl-CoA Epimerase

The mm-CoA epimerase from Propionibacterium shermanii was purified and used to obtain N-terminal protein sequence as well as internal peptide sequence from LysC-generated peptides. The epimerase gene was cloned using hybridization probes designed from the peptide sequences.

Propionibacterium freudenreichii subsp. shermanii was obtained and cultured as described in part A. Purification of mm-CoA epimerase from P. shermanii was based on a modification of the published procedure. The procedure utilized a 10 L culture, which was lysed by sonication followed by column chromatography in the order: DE-52, Hydroxyapatite, Phenylsepharose, MonoQ anion exchange, and C-8 RP HPLC.

All operations were performed at 4° C., except the C-8 RP HPLC, which was performed at room temperature, and all buffers contained 0.1 mM PMSF, unless otherwise stated. The epimerase assay was performed essentially as described in the literature. Protein concentration was determined using the method of Bradford. The overall yield of epimerase activity was not determined.

More specifically, cell paste (75 g) was resuspended in 50 mL buffer (50 mM Tris-HCl pH 7.5, 0.1M KCl, 0.2 mM PMSF, 1 mM EDTA) and sonicated using a macrotip with a diameter of 1.2 cm. With pulses of 0.5 seconds ON and 0.3 seconds OFF, the cells were sonicated twice for 30 seconds each at a power setting of 4, followed by five times for 30 seconds each at a power setting of 6. A clear, amber-colored supernatant (53.5 ml) was obtained after spinning for 35 minutes at 12,000 rpm.

The crude extract from above was applied to a column (diameter 2.5 cm, height 15 cm) of 73 mL of DE-52 resin equilibrated with 50 mM Tris-HCl pH 7.5, 0.1M KCl. The column was washed at 1 ml/min with three column volumes of the above buffer, followed by a linear gradient to 50 mM Tris-HCl pH 7.5, 0.5 M KCl over seven column volumes. Six mL fractions were collected and assayed for epimerase activity. The epimerase was found predominantly in the flow-through and in several early fractions. The flow-through and active fractions were combined (325 mL) and dialyzed against 4 liters of 50 mM Tris-HCl pH 7.5, 10% glycerol, followed by 4 liters of 10 mM sodium phosphate pH 6.5, 10% glycerol (final volume 250 mL).

A 7.5 mL hydroxyapatite biogel HTP gel column (diameter 1.5 cm, height 16 cm) was equilibrated with 10 mM sodium phosphate pH 6.5, 5% glycerol. After loading of the enzyme solution (using repeated injections) and washing with three column volumes of the above buffer, a gradient to 200 mM sodium phosphate pH 6.5, 5% glycerol was effected over 20 column volumes at a flow rate of 1 ml/min. The 2 mL fractions were assayed for epimerase activity, and fractions containing epimerase activity were pooled for a total of 99 ml.

To the 99 mL sample from above, solid ammonium sulfate to 1.5 M final concentration was added slowly and with stirring at 4° C. over 30 minutes. This suspension (100 mL) was loaded, by repeated injection, onto a 6.6 mL column (1 cm×height 8.5 cm) of phenyl-sepharose resin equilibrated in 20 mM sodium phosphate buffer pH 6.5, 1.5 M ammonium sulfate. The column was washed at 1 m/min with three column volumes of this buffer, followed by a linear gradient to 20 mM sodium phosphate buffer pH 6.5, 10% glycerol, over 24 column volumes. After assaying the 3 mL fractions for epimerase activity, the fractions containing epimerase activity were pooled and dialyzed against 50 mM Tris-HCl pH 7.5.

A mono Q 5/5 prepacked column was equilibrated with 25 mM Tris-HCl pH 7.5 at 0.5 mL/min. The sample from the previous step was loaded onto the column, which was then washed with 5 column volumes of the above buffer, followed by a linear gradient to 50 mM Tris-HCl pH 7.5, 1 M NaCl, 5% glycerol, over 50 column volumes. The 1 mL fractions were assayed for epimerase activity. Several fractions containing epimerase activity were stored separately; the fraction with the most activity was used for the next purification step.

A reverse-phase column was equilibrated with water containing 0.1% trifluoroacetic acid; 120 µL (concentrated from 0.5 mL of the active fraction from above, using an Amicon microconcentrator) was injected onto the column at a flow rate of 0.2 mL/min and washed for five minutes with the above solvent system. Then a linear gradient over 50 minutes to acetonitrile containing 0.1% trifluoroacetic acid was implemented. The peaks were collected manually and the peak corresponding to the epimerase (as determined by SDS/PAGE) was dried to completeness, resuspended in water and stored at −80° C.

For Lys C mediated digestion of the HPLC-purified epimerase, the epimerase fraction (11751 rp2-B, 200 µL) collected from reverse phase HPLC was dried to completeness and resuspended in 40 µL water. To 30 µL of the sample was added 5 µL of 1 M Tris/HCl, pH 8, 1.5 µL of 0.1 M DTT, 2 µL of Lys C protease (0.2 µg). A control reaction contained all of the above components except the epimerase. The reactions were incubated overnight at 37° C. An aliquot of the reaction (5 µL) was diluted to 60 µL with water and loaded to the HPLC, using the same HPLC program that was used to purify the epimerase. The analytical HPLC showed that the Lys C digestion was not complete. An additional aliquot of Lys C (0.2 µg) was added to the reactions and incubation was continued overnight at 37° C. Following overnight incubation, an aliquot of the reaction (5 µL) was diluted to 60 µL with water and subjected to the HPLC. The HPLC showed that the digestion was complete. The remainder of the reaction was loaded to the HPLC and individual peaks were collected manually. HPLC of the control reaction showed no significant peptide fragments arising from self-digestion of the LysC.

An aliquot of the pure epimerase, as well as a peptide collected from the procedure described above, were submitted for N-terminal amino acid sequencing. Based on the amino acid sequences from above, several degenerate primers were designed as described below that introduced unique restriction sites to either end of the eventual PCR product. These primers were used in PCR with P. shermanii genomic DNA to obtain a 200 base-pair product, which was cloned into a Bluescript™ (Stratagene) vector and submitted for sequencing.

A cosmid library of P. shermanii was prepared, essentially as described in the Stratagene cosmid manual. The titer of this cosmid library was approximately 11 cfu (colony forming units) per µL, for a total yield of 5556 cfu. A plasmid library of P. shermanii was prepared by digesting P. shermanii genomic DNA with SacI and ligating the resulting mixture into a Bluescript™ vector also cut with SacI. To determine the average insert size (2 kb), ten random clones were digested with SacI. The ligation mixture was re-transformed 5 times, pooled and plated on one large LB (carb) plate, resulting in a lawn of colonies that were scraped together and resuspended in LB as the plasmid library. The titer of this plasmid library was approximately 64,000 cfu per µL.

Several degenerate primers based on the amino acid sequences were prepared and used in PCR with P. shermanii genomic DNA to obtain a 180 base-pair product, which was cloned into a Bluescript™ vector and sequenced. Several different probes were made. The first probe was made using the random priming method to incorporate either $^{32}p$ or digoxigenin into the epimerase fragment. A probe was made from the cloned fragment by amplification of the fragment via PCR, using the digoxigenin labeling method. The PCR product was gel isolated, quantified, and used to probe the cosmid library. Colonies that hybridized to the probe were restreaked from master plates, and five colonies from the re-streaked plates were picked, cosmids were isolated, and the insert sequences screened for the epimerase gene by PCR. Several cosmids that were scored positive for epimerase DNA sequence by PCR were subjected to DNA sequencing using epimerase-specific primers. The cosmid designated 117-167-A7 contained the full epimerase sequence.

The sequence of the putative epimerase gene contained in cosmid 117-167-A7 was aligned to the N-terminal epimerase sequence already known. The several hundred base pairs downstream of this sequence were translated in all three frames and a stop codon in one of the frames was found that yielded a protein of the expected size. The entire sequence, was used to search the protein database via BLAST analysis, and the sequence showed high homology to the sequence of a putative epimerase from S. coelicolor identified in accordance with the methods of the invention. PCR primers were designed based on the DNA sequence of the cloned P. shermanii epimerase and the gene was amplified from P. shermanii genomic DNA with NdeI and BamHI sites at the 5'-end, an internal NdeI site was destroyed near the 5' end, and NheI and AvrII sites were introduced at the 3'-end. Following PCR, the 447 bp product was cloned into a Bluescript vector (143-6-11) and sequenced. Also, four additional sequencing primers were designed to provide several-fold coverage of the epimerase gene. The full epimerase gene sequence provided in isolated and recombinant form by the present invention is provided below as SEQ ID No: 1, and the protein sequence of the epimerase is provided below as SEQ ID No: 2. The epimerase gene was then cloned into a pET expression vector; the construct was named pET-epsherm.

For the cloning of epimerase genes from *B. subtilis* (described by Haller et al, supra) and *S. coelicolor* (from cosmid 8F4 in the *S. coelicolor*, genome sequencing project), primers were designed to PCR these genes from their respective genomic DNAs and to incorporate either a PacI or NdeI site at the 5' end, and an NsiI site at the 3' end. The PCR products were cloned into a Bluescript™ vector and sequenced. Mutation-free clones were obtained for the *S. coelicolor* epimerase, but the *B. subtilis* epimerase contained two point mutations in all three clones tested: C to T at base pair 37, and G to A at base pair 158. When the PCR for this epimerase gene was repeated and the product cloned and sequenced, the same mutations were present, implying that the original sequence was in error. The cloned epimerases from *B. subtilis* and *S. coelicolor* were cloned as NdeI/NsiI fragments into an intermediate vector 116–172a, a Bluescript™ pET plasmid containing the T-7 promoter and terminator sequences. The cloned epimerases from *B. subtilis* and *S. coelicolor* are pET-epsub and pET-epcoel, respectively. The epimerase genes were also excised along with the T7 promoter as PacI/NsiI fragments, as shown schematically below.

---PacI---T7 promoter------epimerase gene--------NsiI--- and cloned into the PacI/NsiI restricted vector 133-9b, to form a single operon with the epimerase gene located downstream of the two mutase genes. The epimerase gene from *P. shermanii* was cloned as above except that it was cloned into 116–172a as an NdeI/AvrII fragment, excised along with the T7 promoter as a PacI/NheI fragment, and cloned into 133–9b between PacI and NheI sites. The constructs are pET-mutAB-T7-epsherm, pET-mutAB-T7-epsub, and pET-mutAB-T7-epcoel.

As an alternative to the mutase from *P. shermanii, S. coelicolor*, and *B. subtilis*, one can clone by PCR from *E. coli* genomic DNA the single gene for Sbm (sleeping beauty mutase). Genomic DNA of *E. coli* BL21 (DE3)/PanD was prepared using a kit purchased from Qiagen. The gene for Sbm (Sleeping beauty mutase, a methylmalonyl-CoA mutase) was amplified by PCR from *E. coli* BL21(DE3)/PanD genomic DNA. The PCR fragment was gel isolated, cloned into PCRscript and sequenced to yield the mutation-free clone 143-11-54. Excised as an NdeI/SacI fragment, sbm was cloned into pET22b, thence as a NdeI/XhoI fragment into pET 1 6b to introduce an N-terminal His-Tag (143-49-2). Sbm was also cloned between NdeI and SpeI into 116-95B.43, a pET22b vector that allows subsequent cloning of the epimerase genes downstream of the sbm. That construct was named 143-40-39.

Cells of strain BL21(DE3) containing pET-epshemm, pET-epcoel, pET-epsub, or a control pET vector were grown overnight at 37° C. in 2 mL LB containing 100 µg/ml carbenicillin. The starter culture (250 µL) was used to inoculate 25 mL LB containing 100 µg/ml carbenicillin. The cultures were grown at 37° C. to an OD of approximately 0.4, then induced with IPTG to 1 mM final concentration and grown for an additional 3 hours at 30° C. The cells were collected by centrifugation at 4000 rpm for 10 minutes, and the pellets were stored at −80° C. prior to assay. The epimerase from *P. shermanii* expressed well in *E. coli*; SDS gel analysis revealed an overexpressed protein at approximately 22 kDa. The *S. coelicolor* epimerase also expressed well, at a molecular weight of approximately 19 kDa, and the *B. subtilis* epimerase was expressed, but mostly in inclusion bodies (a faint band is present at approximately 19 kDa), which can be overcome by use of alternate expression systems.

Epimerase activity was measured in crude extracts of *E. coli* harboring either pET-epshemm, pET-epcoel, pET-epsub, or a control pET vector. The epimerase assay couples transcarboxylase, which converts (S)-methylmalonyl-CoA into propionyl-CoA, to malate dehydrogenase, which converts NADH into NAD+, producing a decrease in absorbance at 340 nm. The assay is initiated with a racemic mixture of (R,S)-methylmalonyl-CoA; when the (S)-isomer is consumed as described below, a steady background rate is observed at about one-tenth of the initial rate. When an extract containing epimerase is added to the assay, the (R)-isomer is converted to (S)-, resulting in a further decrease in absorbance. In crude *E. coli* extracts, however, a significant background rate is observed, probably due to an endogenous NADH oxidase. Thus the epimerase must be expressed at a sufficiently high level to conclude that it is active. The assay was conducted as follows.

The pellet from approximately 20 mL of culture was thawed and resuspended in 2 mL 1× assay buffer containing a protease inhibitor cocktail tablet. The cells were disrupted by sonication (two sonication cycles for 30 seconds each at a power setting of 2 [pulse ON 0.5 sec/pulse OFF 0.5 sec]). After spinning for 10 minutes at 13,000 rpm in an Eppendorf centrifuge, the supernatents were saved for assay. Methylmalonyl-CoA epimerase activity was assayed using a modification of the method of Leadlay et al., *Biochem. J.* 197: 413–419, "Purification and characterization of methylmalonyl CoA epimerase from *Propionibacterium shermanii*" (1981). The assays were performed at 30° C. with a 1 cm path length plastic cuvette, in a final volume of 1.5 mL. The reaction mixtures contained 0.2 M potassium phosphate buffer pH 6.9, 0.1 M ammonium sulfate, 5 mM sodium pyruvate, 0.08 mM (2R,2S)-methylmalonyl-CoA, 0.05 units of partially purified transcarboxylase, 0.16 mM NADH, and 2.5 units malate dehydrogenase. The reaction was initiated with (2R,2S)-methylmalonyl-CoA and the decrease in absorbance at 340 nm was monitored, reflecting the disappearance of the 2S isomer. When the decrease in absorbance at 340 nm reached the basal level (usually around 10% of the initial transcarboxylase rate), an extract containing epimerase was added and a further decrease in absorbance was observed. The chemicals and enzymes used in the epimerase assay were purchased from Sigma, except for transcarboxylase, which was obtained as a crude preparation from Case Western Reserve.

The crude extracts harboring both the *P. shermanii* and *S. coelicolor* epimerases had specific activities (approximately 30 units/mg) at least 10 times higher than that of the control. However, no activity above the background level was observed in the extract harboring the *B. subtilis* epimerase, possibly because it was not expressed at a high enough level, or as noted above, was expressed as insoluble inclusion bodies. The pET-mutAB-T7-epsherm construct was also expressed in *E. coli*. The resulting crude extract contained epimerase activity that was significantly above the background level; thus, the epimerase is functional in this construct. The mutase did not interfere in the epimerase assay, because these cells were grown without addition of hydroxocobalamin, the cofactor for mutase activity. These results show that one can express both active mutase and active epimerase in an *E. coli* cell. These results also show that the methylmalonyl-CoA epimerase from *P. shermanii* was cloned, expressed in *E. coli*, and active, and that the putative epimerase from *S. coelicolor* is a methylmalonyl-CoA epimerase. These genes can be integrated into the chromosome of an *E. coli* PanD strain or other strain and used for the production of polyketides built in whole or in part from methylmalonyl CoA.

EXAMPLE 2

Production of Methylmalonyl CoA in Yeast

This example describes the construction of strains of *Saccharomyces cerevisiae* optimized for polyketide overproduction. In particular, this example describes the construction of yeast host strains that (i) produce substrates and post-translational modification enzymes necessary to express polyketides made by modular polyketide synthases; (ii) have necessary nutritional deficiencies to allow positive selection of at least three compatible plasmids; and/or (iii) are suitable to permit radioactive labeling of acyl-CoA pools and polyketide synthases and demonstrates that such strains can express a modular PKS and produce a complex polyketide at levels suitable for commercial development. References are cited in this example by a number corresponding to the numbered list of references below, each of which is incorporated herein by reference.

With appropriate strain modifications, *S. cerevisiae* is an ideal host for polyketide production. *S. cerevisiae* is capable of producing very high levels of polyketides. Introduction of the gene for the iterative PKS, 6-MSAS, along with the gene for Sfp, a P-pant transferase from *B. subtilis*, led to the production of an impressive 2 g/L 6-MSA in shake-flasks without optimization Kealey, J. T., et al., *Production of a polyketide natural product in nonpolyketide-producing prokaryotic and eukaryotic hosts*. Proc Natl Acad Sci USA, 1998. 95(2): p. 505–9, incorporated herein by reference. The genetics of yeast is very well understood. Genes can readily be inserted into the chromosome, and the complete genome sequence provides relevant knowledge regarding metabolic pathways and neutral insertion sites. In addition, several strong, controllable promoters are available. Proteins have less tendency to form inclusion bodies in yeast, compared to *E. coli*. Yeast has a relatively short doubling time in comparison to native polyketide producing organisms. *S. cerevisiae* has a doubling time of 1 to 2 hr compared to 4 to 24 hr for a typical polyketide producer, which has obvious benefits in genetic development, process development, and large-scale production.

The fact that yeast grow as single cells provides an additional benefit over filamentous organisms (typical polyketide producers). Mycelial fermentations are viscous and frequently behave as non-Newtonian fluids. This fluid rheology provides a significant obstacle to the process scientist both in terms of uniform nutrient transport to the cells and in handling the fermentation broth. Employing yeast as a host, even at high cell densities, avoids such impediments. Because of the extensive history of yeast in single cell protein production and the expression of recombinant proteins, scalable fermentation protocols for yeast have been developed. Yeast can be grown in fed-batch fermentations to very high cell densities (>100 g/L biomass) as compared to typical polyketide producers (10–20 g/L biomass). Thus, comparing organisms with the same specific productivity (g polyketide/g biomass/day), yeast would provide a higher volumetric productivity (g polyketide/L/day). Finally, *S. cerevisiae* is classified by the FDA as a "Generally Regarded As Safe" (GRAS) organism. GRAS classification will facilitate approval of drugs produced in yeast as compared to other host cells.

*S. cerevisiae* also has disadvantages as a host for polyketide biosynthesis, most of which are related to the fact that yeast did not evolve to produce polyketides. Yeast does not contain methylmalonyl-CoA, a necessary precursor for biosynthesis of many polyketides. Yeast does not have a suitable P-pant transferase capable of the necessary post translational modification of ACP domains of a PKS. Yeast codons are biased towards A+T, whereas most polyketide producers have high G+C codons; thus, yeast may have low amounts of some tRNAs needed for PKS gene expression. The correction of these deficiencies is described in this example, and the invention also provides modified yeast host cells useful to facilitate analysis of success.

Other case-by-case potential issues with yeast include the possibility that some polyketide products may be toxic or may require additional modifications for maturation (e.g. glycosylation, P450 hydroxylation). Several methods provided by the invention may be taken to circumvent these issues should they arise. For toxicity, production may be controlled to occur in stationary phase growth (as with 6-MSA production); resistance factors from the wild type host may be introduced into the yeast host (e.g. methylation of ribosomes for some antibiotics); a non-toxic-precursor to the polyketide may be produced and converted ex vivo (e.g. produce 6-dEB in one strain and convert it to erythromycin in another), and others. Additional modifications to the polyketide may be accomplished by cloning and expressing modification enzymes into the host strain, chemical or enzymic transformation, and/or biosynthetic transformation in a second strain (e.g. convert 6-dEB analogs to erythromycin analogs by feeding 6-dEB to a *Streptomyces* or *Saccharopolyspora* strain capable of glycosylation and P450 hydroxylation).

Most modular PKSs require either or both malonyl-CoA or (2S)-methylmalonyl-CoA as a source of 2-carbon units for polyketide biosynthesis. The malonyl-CoA pools in yeast are quite sufficient for polyketide synthesis, as illustrated by the production of large amounts of 6-MSA in yeast. However, *S. cerevisiae* does not produce (2S)-methylmalonyl-CoA and does not possess biosynthetic pathways for methylmalonyl-CoA biosynthesis. Hence, a heterologous biosynthetic pathway must be introduced into *S. cerevisiae* to support biosynthesis of polyketides that use (2S)-methylmalonyl-CoA as a precursor.

Figure 5:
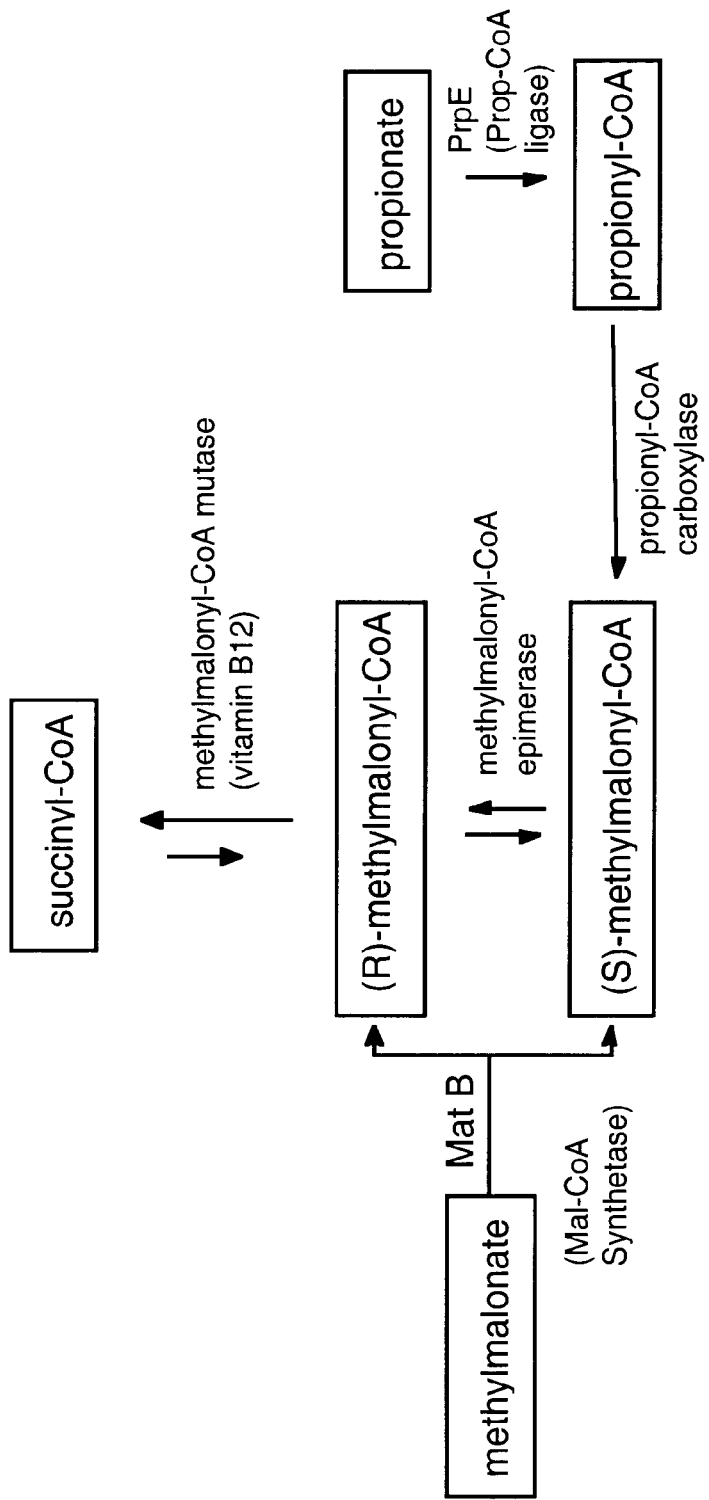
FIG. 5 shows the three routes or biosynthetic pathways for the synthesis of methylmalonyl-CoA that can be engineered into yeast.

There are three routes or biosynthetic pathways for the synthesis of methylmalonyl-CoA that can be engineered into yeast, as shown in FIG. 5. These pathways have been shown to produce methylmalonyl-CoA in *E. coli* and can be used to produce methylmalonyl-CoA in yeast. This example describes the identification of a system for methylmalonyl-CoA production in yeast, and a method for introducing it into the yeast chromosome.

The vitamin B12-dependent methylmalonyl-CoA mutase pathway produces (2R)-methylmalonyl-CoA from succinyl-CoA. The (2R)-methylmalonyl-CoA is converted to the (2S)-diastereomer via methylmalonyl-CoA epimerase, as shown above. These enzymes are present in a variety of organisms, but not yeast; BLAST searches of the available genomic databases reveals at least 10 methylmalonyl-CoA mutases and 10 methylmalonyl-CoA epimerases in various organisms. The *Propionibacterium shermanii* methylmalonyl-CoA mutase has been expressed in *E. coli* as the apo-enzyme, which requires addition of vitamin B12 for in vitro activity (McKie, N., et al., *Adenosylcobalamin-dependent methylmalonyl-CoA mutase from Propionibacterium shermanii. Active holoenzyme produced from Escherichia coli*. Biochem J, 1990. 269(2): p. 293–8; incorporated herein by reference). By use of a medium that enables uptake of the vitamin B12 precursor hydroxocobalamin (Amaratunga, M., et al., *A synthetic module for the metH gene permits facile mutagenesis of the cobalamin-binding region of Escherichia coli methionine synthase: initial characterization ofseven mutant proteins*. Biochemistry, 1996. 35(7): p. 2453–63; incorporated herein by reference), and in accordance with the methods of the invention, one can express active *P. shermanii* methylmalonyl-CoA mutase holoenzyme in *E. coli* and produce (2R)-methylmalonyl-CoA in such cells. In addition, one can employ the single subunit methylmalonyl-CoA mutase from *E. coli*. The present invention also provides the genes encoding methylmalonyl-CoA epimerase from *B. subtilis, P. shermanii* and *S. coelicolor* and methods for using them in converting (2R)-methylmalonyl-CoA to the needed (2S)-diastereomer. A preferred method is to express in yeast the methylmalonyl-CoA mutase from *E. coli*, because it is a single ORF, and necessary codons are plentiful in yeast. Alternatively, the *P. shermanii* enzyme can be used.

PCC catalyzes the biotin-dependent carboxylation of propionyl-CoA to produce (2S)-methylmalonyl-CoA, as shown above; the pathway also includes a biotin carrier protein/biotin carboxylase. In *S. coelicolor*, Rodriguez and Gramajo identified genes for PCC (pccB) and a biotin carrier protein/biotin carboxylase (accA1) (Rodriguez, E. and H. Gramajo, *Genetic and biochemical characterization of the alpha and beta components of a propionyl-CoA carboxylase complex of Streptomyces coelicolor A3(2)*. Microbiology, 1999. 145 (Pt 11)): p. 3109–19; incorporated herein by reference). Introduction into *E. coli* of *S. coelicolor* pccB and accA1 along with propionyl-CoA ligase (as a supply of propionyl-CoA), results in the production of methylmalonyl-CoA in that organism. A search of the genomic database reveals *B. subtilis* as an additional source of the enzymes involved in the PCC pathway.

In one embodiment of the invention, one can express the *S. coelicolor* pccB and accA1 in yeast, because these are expressed and the proteins are functional in *E. coli*. Should codon usage prove suboptimal when expressing the *S. coelicolor* genes in yeast, homologs from *B. subtilis* can be employed. Should the levels of propionyl-CoA be suboptimal for PCC, one can co-express a propionyl-CoA ligase in the yeast host. Intracellular propionyl-CoA can be greatly increased in *E. coli* by expressing the *Salmonella* propionyl-CoA ligase, PrpE, and supplementing the growth media with propionate, as described below.

An additional method for the production of (2S)-methylmalonyl-CoA provided by the present invention utilizes the matB and matC genes from *Rhizobium* (An, J. H. and Y. S. Kim, *A gene cluster encoding malonyl-CoA decarboxylase (MatA), malonyl-CoA synthetase (MatB) and a putative dicarboxylate carrier protein (MatC) in Rhizobium trifolii—cloning, sequencing, and expression of the enzymes in Escherichia coli*. Eur J Biochem, 1998. 257(2): p. 395–402; incorporated herein by reference) or *S. coelicolor* (see schematic above). The matABC genes code for a biosynthetic pathway that converts malonate to acetyl-CoA through formation of malonyl-CoA via MatB and subsequent decarboxylation by MatA. MatB, the malonyl-CoA ligase, also accepts methylmalonate as a substrate (An, J. H. and Y. S. Kim, *A gene cluster encoding malonyl-CoA decarboxylase (MatA), malonyl-CoA synthetase (MatB) and a putative dicarboxylate carrier protein (MatC) in Rhizobium trifolii—cloning, sequencing, and expression of the enzymes in Escherichia coli*. Eur J Biochem, 1998. 257(2): p. 395402; incorporated herein by reference) and catalyzes formation of methylmalonyl-CoA. The substrates malonate or methylmalonate enter the cell through a diacid transporter, the product of the matC gene. Khosla et al. have shown that when *E. coli* containing the *Rhizobium* matBC is fed (2R,2S)-methylmalonate, (2R,2S)-methylmalonyl-CoA is produced. Furthermore, when an *S. coelicolor* strain expressing the genes for the synthesis of the polyketide aglycone, 6-deoxyeythronolide B (6-dEB), and containing *Rhizobium* matBC, is fed methylmalonate, a 3-fold increase in production of 6-dEB is observed. In accordance with the methods of the invention, one can express the matB and matC genes from *Rhizobium* in yeast, because these are expressed and the proteins are functional in *E. coli* and *S. coelicolor*, or, alternatively the matBC genes from *S. coelicolor*.

Active PKSs require post-translational phosphopantetheinylation at each ACP of each module, but yeast does not contain a P-pant transferase with the needed specificity (Kealey, J. T., et al., *Production of a polyketide natural product in nonpolyketide-producing prokaryotic and eukaryotic hosts*. Proc Natl Acad Sci USA, 1998. 95(2): p. 505–9; incorporated herein by reference). Previous work (Kealey, J. T., et al., *Production of a polyketide natural product in nonpolyketide-producing prokaryotic and eukaryotic hosts*. Proc Natl Acad Sci USA, 1998. 95(2): p. 505–9; incorporated herein by reference) has shown that introduction of the *B. subtilis* P-pant transferase gene, sfp, into yeast results in an expressed Sfp capable of modifying an iterative PKS, 6-MSAS. Gokhale et al. demonstrated that the ACP domains in the DEBS PKS are substrates for Sfp, so Sfp is a general modifying enzyme for PKSs (Gokhale, R. S., et al., *Dissecting and exploiting intermodular communication in polyketide synthases*. Science, 1999. 284(5413): p. 482–5; incorporated herein by reference). In preferred yeast host cells of the invention, the sfp gene is inserted into a neutral site of the yeast chromosome.

In developing a system to produce polyketides and optimize fermentation procedures, the ability to measure intracellular concentrations of substrates (i.e. acyl-CoAs) and of the PKS is beneficial. In most cells, CoA esters are not present in sufficient amounts to allow direct measurement by HPLC using ultraviolet detection or other simple methods of detection. In *E. coli*, the method of choice to quantify CoA pools is to feed [$^3$H] β-alanine to a mutant deficient in aspartate decarboxylase (PanD), which cannot produce endogenous 13-alanine (Jackowski, S. and C. O. Rock, *Regulation of coenzyme A biosynthesis*. J Bacteriol, 1981. 148(3): p. 926–32; incorporated herein by reference). The PanD strain incorporates about ten-fold more radioactivity into CoA pools than does wild type *E. coli*. Because 13-alanine is a direct precursor of CoA, the radioactive label enters the CoA pool without dilution, and acyl-CoAs can be separated on HPLC and quantified by radioactivity measurement. Because there is no radioisotope dilution, the radioactivity measured reflects exact intracellular concentrations of the acyl-CoAs.

BLAST searches did not reveal an *E. coli* PanD homolog in the yeast genome; however, yeast may be a β-alanine or pantothenate auxotroph. Indeed, for CoA biosynthesis, yeast requires either exogenous pantothenate, which enters the cell via the Fen2p transporter, or exogenous β-alanine, which enters via the general amino acid permease (Gap Ip) (Stolz, J. and N. Sauer, *The fenpropimorph resistance gene FEN2 from Saccharomyces cerevisiae encodes a plasma membrane H+-pantothenate symporter*. J Biol Chem, 1999. 274(26): p. 18747–52; incorporated herein by reference). [$^3$H] β-alanine is incorporated into CoA pools of yeast (see below), but it is presently unknown whether isotope dilution occurs due to endogenous β-alanine production by some unknown pathway. Thus, to enable quantitation, one can determine the specific activity of CoA pools in yeast labeled with exogenous [$^3$H] β-alanine. Cells producing polyketides generally express low levels of high molecular weight PKSs that are barely detectable on SDS-PAGE using protein stains. The ability to label CoA with [3H] β-alanine can also be used to quantify a PKS expressed in the host cells because the phosphopantetheine moiety of CoA containing β-alanine is transferred to the ACP domain in each module of a PKS. Thus, knowing the specific activity of labeled intracellular CoAs, a PKS can be simply quantified by radioactivity after SDS-PAGE.

The G+C content of most PKS genes is in the range of 60 to 70%, while that of yeast genes is 40%. Thus, some tRNAs needed to translate PKS genes are scarce (but not absent) in yeast. However, many genes with high G+C content have been expressed in yeast. As examples, the large (1560 bp) DHFR-TS gene from *Leishmania major* (63% G+C) is expressed well in yeast, despite the fact that it contains several codons rarely used in yeast (Grumont, R., W. Sirawarapom, and D. V. Santi, *Heterologous expression of the bifunctional thymidylate synthase-dihydrofolate reductase-from Leishmania major*. Biochemistry, 1988. 27(10): p. 3776–84; incorporated herein by reference). Moreover, as mentioned below, the PKS 6-MSAS (G+C=58%) is also expressed well in yeast (Kealey, J. T., et al., *Production of a polyketide natural product in nonpolyketide-producing-prokaryotic and eukaryotic hosts*. Proc Natl Acad Sci USA, 1998. 95(2): p. 505–9; incorporated herein by reference). Thus, one can demonstrate the general applicability of a yeast expression system without initial concern for potential codon usage problems. Nevertheless, if a desired PKS does not express well in yeast, the present invention provides several methods to solve a "codon usage" problem observed with a particular polyketide.

First, one can change the codons at the 5' end of the gene to reflect those more frequently found in yeast genes. Batard et al. (Batard, Y., et al., *Increasing expression of P450 and P450-reductase proteins from monocots in heterologous systems [In Process Citation]*. Arch Biochem Biophys, 2000. 379(1): p. 161–9; incorporated herein by reference) successfully employed a similar method to express in yeast wheat genes for a P450 and P450 reductase with high G+C content (56%) and strong bias of codon usage unfavorable to yeast. Another method is to introduce yeast tRNA genes with anti-codons modified to represent codons common in PKS sequences. A similar method has been successfully used in *E. coli* to enhance expression of high G+C genes (Carstens, C. -P., et al., *New BL21-CodonPlus™ Cells Correct Codon Bias in GC-Rich Genomes*. Strategies Newsletter from Stratagene Corp., 2000. 13(1): p. 31–33; incorporated herein by reference), including PKS genes from Actinomycetes. A third method is to synthesize chemically the gene with codons optimized for expression in yeast. The cost for contract synthesis of a 30,000 bp gene (e.g. ~6-module PKS), including sequence verification, is approximately $3 per base, or about $100,000. For a valuable product (e.g. epothilone), the cost is not prohibitive.

In an illustrative embodiment of the invention, a yeast strain deficient in Ura, Trp, His and Leu biosynthesis is employed as a host to allow selection of plasmids containing these markers. This host is modified in accordance with the methods of the invention by introducing genes that produce the needed methylmalonyl-CoA substrate and P-pant transferase for post-translational modifications of PKSs. These are preferably integrated into the yeast chromosome, because they are necessary for production of any polyketide. To validate functional expression of the substrate genes, one can measure methylmalonyl-CoA pools. For validation of P-pant transferase activity, one can coexpress 6-MSAS and measure [$^3$H] phosphopantetheinylation of the enzyme as well as 6-MSA production. Should either be deficient, one can increase gene copy number.

For PKS gene expression, one can use replicating vectors based on the 2 micron replicon, because plasmids may have to be rescued for analysis should a problem arise. A typical modular PKS gene cluster (eg. 3 ORFS, ~10 kB each, as in erythromycin) can be introduced on three or more vectors; such plasmids (containing Ura, Trp and Leu markers) are available and similar to those used in the studies of 6-MSAS expression in yeast. A PKS consisting of three large proteins can be functionally reconstituted from separately expressed genes (Xue, Q., et al., *A multiplasmid approach to preparing large libraries of polyketides*. Proc Natl Acad Sci USA, 1999. 96(21): p. 11740–5; incorporated herein by reference). Once a system is established for a particular PKS of interest, one can integrate the PKS genes into stable, neutral sites of the chromosome.

Preferred promoters include the glucose repressible alcohol dehydrogenase 2 (ADH2) promoter and the galactose-inducible (GAL1) promoter. The former has been used to produce high amounts of the polyketide 6-MSA in yeast, and the latter is highly controllable by galactose in the medium.

A model modular PKS that one can use to optimize the yeast host is the well studied DEBS1. In this model system, the first ORF of the modular PKS for erythromycin biosynthesis (DEBS1) has been fused to a thioesterase domain (TE) and produces a readily detectable triketide lactone when expressed in *S. coelicolor*, and more recently *E. coli* (Kao, C. M., et al., *Engineered biosynthesis of a triketide lactone from an incomplete modular polyketide synthase*. J. Am. Chem. Soc., 1994. 116(25): p. 11612–11613; Cortes, J., et al., Repositioning of a domain in a modular polyketide synthase to promote specific chain cleavage. Science, 1995. 268(5216): p. 1487–9; both incorporated herein by reference). The gene contains 2 PKS modules, is about 12 kB, and produces a protein that is 300 kDa. This model allows one to optimize the engineered host for acyl-CoA levels and post-translational modifications, the PKS for G+C content, and to develop the needed analytical methods. Once optimized for DEBS1, one can express any given modular PKS.

Previously, it has been shown that the fungal gene encoding 6-methylsalicylic acid synthase (6-MSAS) from *Penicillium patulum* was expressed in *S. cerevisiae* and *E. coli* and the polyketide 6-methylsalicylic acid (6-MSA) was produced (Kealey, J. T., et al., *Production of a polyketide natural product in nonpolyketide-producing prokaryotic and eukaryotic hosts*. Proc Natl Acad Sci USA, 1998. 95(2): p. 505–9; incorporated herein by reference). In both bacterial and yeast hosts, polyketide production required co-expression of 6-MSAS and a heterologous phosphopantetheinyl transferase (Sfp), which was required to convert the expressed apo-PKS to the holo-enzyme. Production of 6-MSA in *E. coli* was both temperature- and glycerol-dependent and levels of production (~60 mg/L) were lower than those of the native host, *P. patulum*. In yeast, the 6-MSAS and sfp genes were co-expressed from separate replicating plasmids, and gene expression was driven by the glucose repressible alcohol dehydrogenase 2 (ADH2) promoter. In a non-optimized shake flask fermentation, the yeast system produced 6-MSA at levels of 2,000 mg/L. This was the first report of expression of an intact PKS gene in yeast or *E. coli*, and demonstrated that extraordinarily high levels of polyketides can be produced in yeast.

Previously, a two vector system was developed for heterologous expression of the three genes comprising the DEBS polyketide gene cluster (Ziermann, R., Betlach, M., *A Two-vector System for the Production of Recombinat Polyketides in Streptomyces*. J. Ind. Microbiol. Biotech., 2000, 24:46–50; incorporated herein by reference). Individual DEBS genes and pairwise combinations of two such genes were each cloned downstream of the actinorhodin (acti) promoter in two compatible *Streptomyces* vectors: the autonomously replicating vector, pKAO127'Kan', and the integrating vector, pSET152. When the resulting plasmids were either simultaneously or sequentially transformed into the heterologous host, *Streptomyces lividans* K4-114, the polyketide product, 6-dEB, was produced. This work showed that the DEBS genes could be split apart and expressed on separate plasmids, and that efficient trans-complementation of modular polyketide synthase subunit proteins occurred in the heterologous host.

A three-plasmid system for heterologous expression of DEBS has been developed to facilitate combinatorial biosynthesis of polyketides made by type I modular PKSs (Xue, Q., et al., *A multiplasmid approach to preparing large libraries ofpolyketides*. Proc Natl Acad Sci U S A, 1999. 96(21): p. 11740–5; incorporated herein by reference). The eryA PKS genes encoding the three DEBS subunits were individually cloned into three compatible *Streptomyces* vectors carrying mutually selectable antibiotic resistance markers. A strain of *Streptomyces lividans* transformed with all three plasmids produced 6-dEB at a level similar to that of a strain transformed with a single plasmid containing all three genes. The utility of this system in combinatorial biosynthesis was demonstrated through production of a large library of greater than 60 modified polyketide macrolactones, using versions of each plasmid constructed to contain defined mutations. Combinations of these vector sets were introduced into *S. lividans*, resulting in strains producing a wide range of 6-dEB analogs. This method can be extended to any modular PKS and has the potential to produce thousands of novel natural products, including ones derived from further modification of the PKS products by tailoring enzymes. Moreover, the ability to express the modular PKSs (such as DEBS) from three separate plasmids provides advantages in the commercialization of polyketide production by heterologous expression of modular PKSs in yeast and *E. coli* in accordance with the methods of the present invention.

As described in Example 1, the translationally coupled genes, mutA and mutB, encoding the β- and α-subunits of methylmalonyl-CoA mutase from *Propionibacterium shermanii*, were amplified by PCR and inserted into an *E. coli* expression vector containing a T-7 promoter. The naturally occurring GTG start codon for mutB was changed to ATG to facilitate expression (Amaratunga, M., et al., *A synthetic module for the metH gene permits facile mutagenesis of the cobalamin-binding region of Escherichia coli methionine synthase: initial characterization ofseven mutant proteins*. Biochemistry, 1996. 35(7): p. 2453–63; incorporated herein by reference). Heterologous expression of the mutase genes in media containing [$^3$H] β-alanine and the adenosylcobalamin (coenzyme $B_{12}$) precursor, hydroxocobalamin, yielded active methylmalonyl-CoA mutase. HPLC analysis of extracts from *E. coli* BL21 (DE3)/panD harboring the mutase genes indicated production of methylmalonyl-CoA, which comprised 13% of the intracellular CoA pool (shown in FIG. 6). This work demonstrates that one can introduce a biosynthetic pathway for an important PKS substrate into a heterologous host, and that one can measure the intracellular concentration of acyl-CoAs. In accordance with the present inveniton, the methylmalonyl-CoA mutase gene (sbm) from *E. coli*, which has codon usage closer to yeast and encodes a single polypeptide (Haller, T., et al., *Discovering new enzymes and metabolic pathways: conversion ofsuccinate to propionate by Escherichia coli*. Biochemistry, 2000. 39(16): p. 4622–9; incorporated herein by reference), can also be employed.

Figure 6:
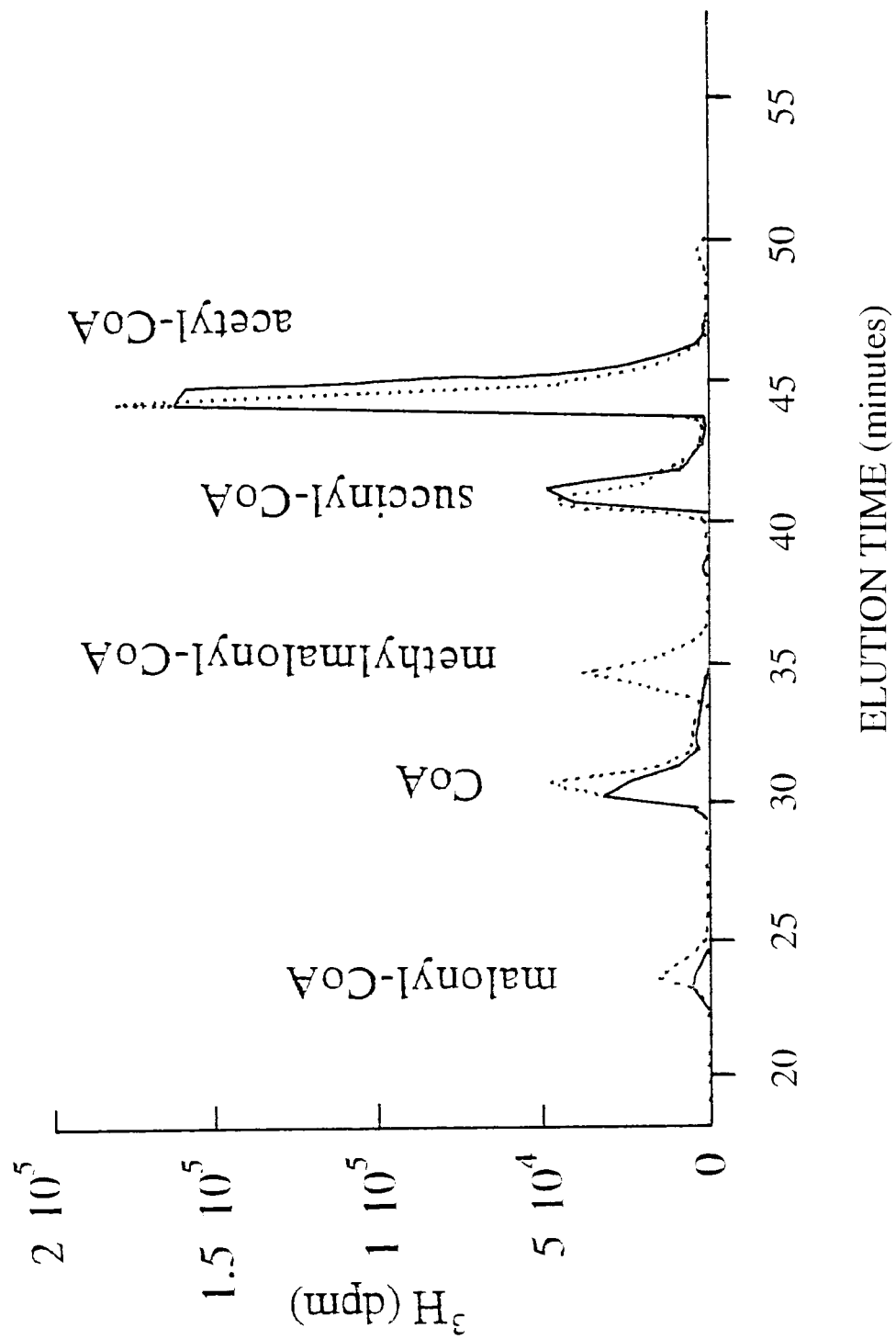
FIG. 6 shows acyl-CoA analysis of *E. coli* overexpressing methylmalonyl-CoA mutase. The levels of $^3$H detected in fractions collected from HPLC of cell-free extracts from $^3$H_-alanine-fed *E. coli* harboring either the pET control vector (solid trace) or pET overexpressing the mutase (dashed trace) is shown.

FIG. 6 shows acyl-CoA analysis of *E. coli* overexpressing methylmalonyl-CoA mutase. The level of $^3$H detected in fractions collected from HPLC of cell-free extracts from [$^3$H] 13-alanine-fed *E. coli* harboring either the pET control vector (solid trace) or pET overexpressing the mutase (dashed trace) is shown.

As described in Example 1, methylmalonyl-CoA epimerase was purified from *Propionibacterium shermanii* and N-terminal and internal protein sequence was obtained. Degenerate PCR primers based on the amino acid sequences were designed and were used to amplify a 180 bp PCR product from *P. shermanii* genomic DNA. The PCR product was labeled and used to isolate the epimerase gene from *P. shermanii*. The methylmalonyl-CoA epimerase genes from *B. subtilis* (Haller, T., et al., *Discovering new enzymes and metabolic pathways: conversion ofsuccinate to propionate by Escherichia coli*. Biochemistry, 2000. 39(16): p. 4622–9; incorporated herein by reference), and *S. coelicolor* can also be employed in the methods of the present invention.

Propionyl-CoA is not detected in *E. coli* SJ16 cells grown in the presence of [$^3$H] β-alanine with or without the addition of propionate in the growth media. When *E. coli* SJ16 cells were transformed with a pACYC-derived plasmid containing the *Salmonella typhimurium* propionyl-CoA ligase gene (prpE) under the control of the lac promoter, a small amount of propionyl-CoA was observed (~2% of total CoA pool) in cell extracts. When 5 mM sodium propionate was included in the culture medium, about 14-fold more propionyl-CoA was produced (~3% of the total CoA pool).

Figure 7:
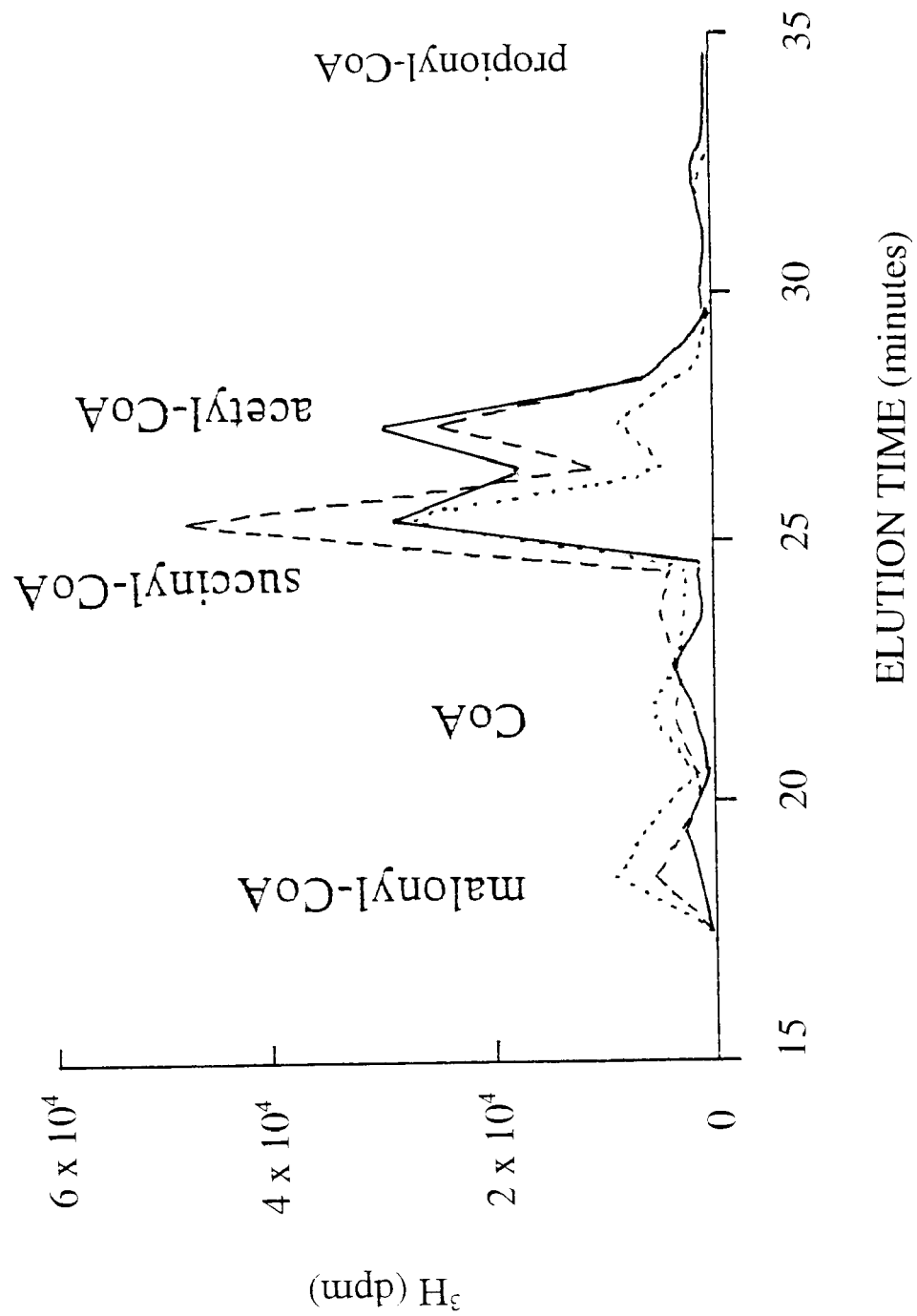
FIG. 7 shows acyl-CoA analysis in *S. cerevisiae*. The levels of $^3$H detected in fractions collected from HPLC of cell-free extracts from $^3$H_-alanine-fed *S. cerevisiae* after growth ofr 24 hours (solid trace), 48 hours (dashed trace) and 66 hours (dotted trace) is shown.

FIG. 7 shows acyl-CoA analysis in *S. cerevisiae*. The level of $^3$H detected in fractions collected from HPLC of cell-free extracts from [3H] 13-alanine-fed *S. cerevisiae* after growth for 24 hours (solid trace), 48 hours (dashed trace) and 66 hours (dotted trace) is shown. The yeast strain InvSc1 (Kealey, J. T., et al., *Production of a polyketide natural product in nonpolyketide-producingprokaryotic and eukaryotic hosts*. Proc Natl Acad Sci USA, 1998. 95(2): p. 505–9; incorporated herein by reference), grown in synthetic YNB media lacking pantothenate and β-alanine, was used for acyl-CoA analysis. Yeast cultures starved of 13-alanine were fed [$^3$H] β-alanine and the cultures were grown for 24, 48 and 66 hours at 30° C. Cells were disrupted with glass beads in the presence of 10% cold TCA and acyl-CoAs were separated by HPLC and quantified by scintillation counting. The yeast CoA pools were labeled with [$^3$H], but the extent of isotope dilution remains unclear. One can measure the specific activity of total CoA in these strains to ascertain the extent of isotope dilution.

Figure 8:
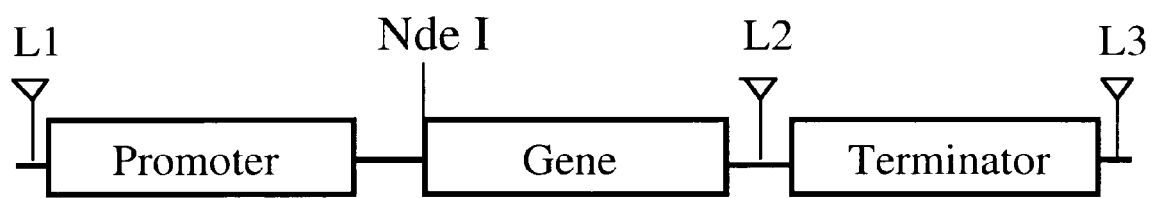
FIG. 8 shows the Common Cloning Cassette.

For PKS genes and initial studies of metabolic pathway genes, one can employ the analogous sets of bluescript cloning vectors and yeast 2 micron replicating shuttle vectors used in 6-MSA production (Kealey, J. T., et al., *Production of a polyketide natural product in nonpolyketide-producing prokaryotic and eukaryotic hosts*. Proc Natl Acad Sci USA, 1998. 95(2): p. 505–9; incorporated herein by reference). With these vectors, yeast expression is driven by the alcohol dehydrogenase 2 (ADH2) promoter, which is tightly repressed by glucose and is highly active following glucose depletion that occurs after the culture reaches high density. Both vector sets have a "common cloning cassette" that contains, from 5' to 3', a polylinker (L1), the ADH2 (or other) promoter, a Nde I restriction site, a polylinker (L2), an ADH2 (or other) terminator, and a polylinker (L3). Due to excess restriction sites in the yeast shuttle vectors, genes of interest are first introduced into intermediate bluescript cloning vectors via the Nde I site, to generate the ATG start codon, and a downstream restriction site in the L2 polylinker that is common to the bluescript and yeast shuttle vectors (shown in FIG. 8). The promoter-gene cassette is then excised as an L1-L2 fragment and transferred to the yeast expression vector containing the transcriptional terminator.

Host strains for model systems include commonly available yeast strains with nutritional deficiencies (Ura, Trp, His, Leu) that can harbor at least three replicating vectors (see below). If it is necessary to express more than three PKS genes simultaneously, one can clone multiple promoter-PKS gene-terminator cassettes into the same vector or use a fourth replicating vector with a different nutritional marker (i.e. Leu) or an antibiotic marker (i.e. G418). One can also construct an analogous set of bluescript cloning and yeast expression/shuttle vectors containing a galactose-inducible promoter. The galactose promoter-Gal4 activator system is more tightly regulated than the ADH2 promoter, and may be beneficial or necessary for expression of proteins that are toxic to yeast (Mylin, L. M., et al., *Regulated GAL4 expression cassette providing controllable and high-level output from high-copy galactose promoters in yeast*. Methods Enzymol, 1990. 185: p. 297–308; incorporated herein by reference).

Genes involved in the production of substrates (eg. methylmalonyl-CoA and/or propionyl-CoA), and the sfp gene can preferably be stably integrated into the yeast chromosome in appropriate copy number to produce adequate levels of desired acyl-CoAs and post translational PKS modifications. Genes can first be introduced into the intermediate bluescript cloning vector as described. Then, the fragment containing the promoter-gene-terminator cassette can be transferred as a L1-L3 fragment to a yeast "delta integration" vector (Lee, F. W. and N. A. Da Silva, *Improved efficiency and stability of multiple cloned gene insertions at the delta sequences of Saccharomyces cerevisiae*. Appl Microbiol Biotechnol, 1997. 48(3): p. 339–45; Lee, F. W. and N. A. Da Silva, *Sequential delta-integration for the regulated insertion of cloned genes* in *Saccharomyces cerevisiae*. Biotechnol Prog, 1997. 13(4): p. 368–73; both incorporated herein by reference) that allows chromosomal integration of the cassettes into one or more of the ca. 425 delta sequences dispersed throughout the yeast chromosome (see FIG. 9). These vectors have cloning sites compatible with those in the L1-L3 linkers to permit direct transfer of promoter-gene-terminator cassettes as L1-L3 fragments. They also contain the excisable Ura3 selection marker flanked by two bacterial hisG repeats ("URA Blaster"), enabling insertion of multiple identical or different genes into the yeast chromosome by repetitive integrations. After selection for gene integration on media lacking uracil, the Ura3 gene fragment is removed by selecting for marker loss via excisional recombination by positive selection with 5-fluoroorotic acid (FOA), which renders the Ura3 gene toxic to yeast. This enables the introduction of stable pathways needed for acyl-CoA precursors and Sfp into yeast, while conserving the Ura marker to allow its subsequent use in plasmids containing other genes.

The single-gene mutase, Sbm (Sleeping beauty mutase), from *E. coli* (Haller, T., et al., *Discovering new enzymes and metabolic pathways: conversion of succinate to propionate by Escherichia coli*. Biochemistry, 2000. 39(16): p. 4622–9; incorporated herein by reference), can be cloned as follows. Primers designed based on the DNA sequence were used to PCR amplify the sbm gene from *E. coli* genomic DNA as a NdeI-L2 fragment. The general strategy for cloning the genes into yeast expression vectors follows that of Kealey et al. (Kealey, J. T., et al., *Production of a polyketide natural product in nonpolyketide-producing prokaryotic and eukaryotic hosts*. Proc Natl Acad Sci USA, 1998. 95(2): p. 505–9; incorporated herein by reference) (see FIG. 9). One can first clone the genes as NdeI-L2 fragments into the intermediate bluescript cloning vector. The promoter-gene-terminator cassette can then be excised as an L1-L3 fragment, transferred to the yeast integrating vector, restricted with L1/L3, and introduced into the yeast chromosome as described above. As an alternative to Sbm, one can use the two-gene mutase from *P. shermanii*; the translationally coupled genes have each been amplified by PCR as NdeI-L2 fragments and can be integrated into yeast as described above.

The genes encoding matABC have been cloned into a bluescript vector (An, J. H. and Y. S. Kim, *A gene cluster encoding malonyl-CoA decarboxylase (MatA), malonyl-CoA synthetase (MatB) and a putative dicarboxylate carrier protein (MatC) in Rhizobium trifolii—cloning, sequencing, and expression of the enzymes in Escherichia coli*. Eur J Biochem, 1998. 257(2): p. 395–402; incorporated herein by reference). One can isolate the matB (methylmalonyl-CoA ligase) and matC (dicarboxylic acid transporter) genes by PCR, each as a NdeI-L2 fragment, and integrate them into the yeast chromosome as described above and shown in the schematic below. Yeast transformed with matBC will be treated with methylmalonic acid, and cells extracts can be analyzed for methylmalonyl-CoA.

Figure 9:
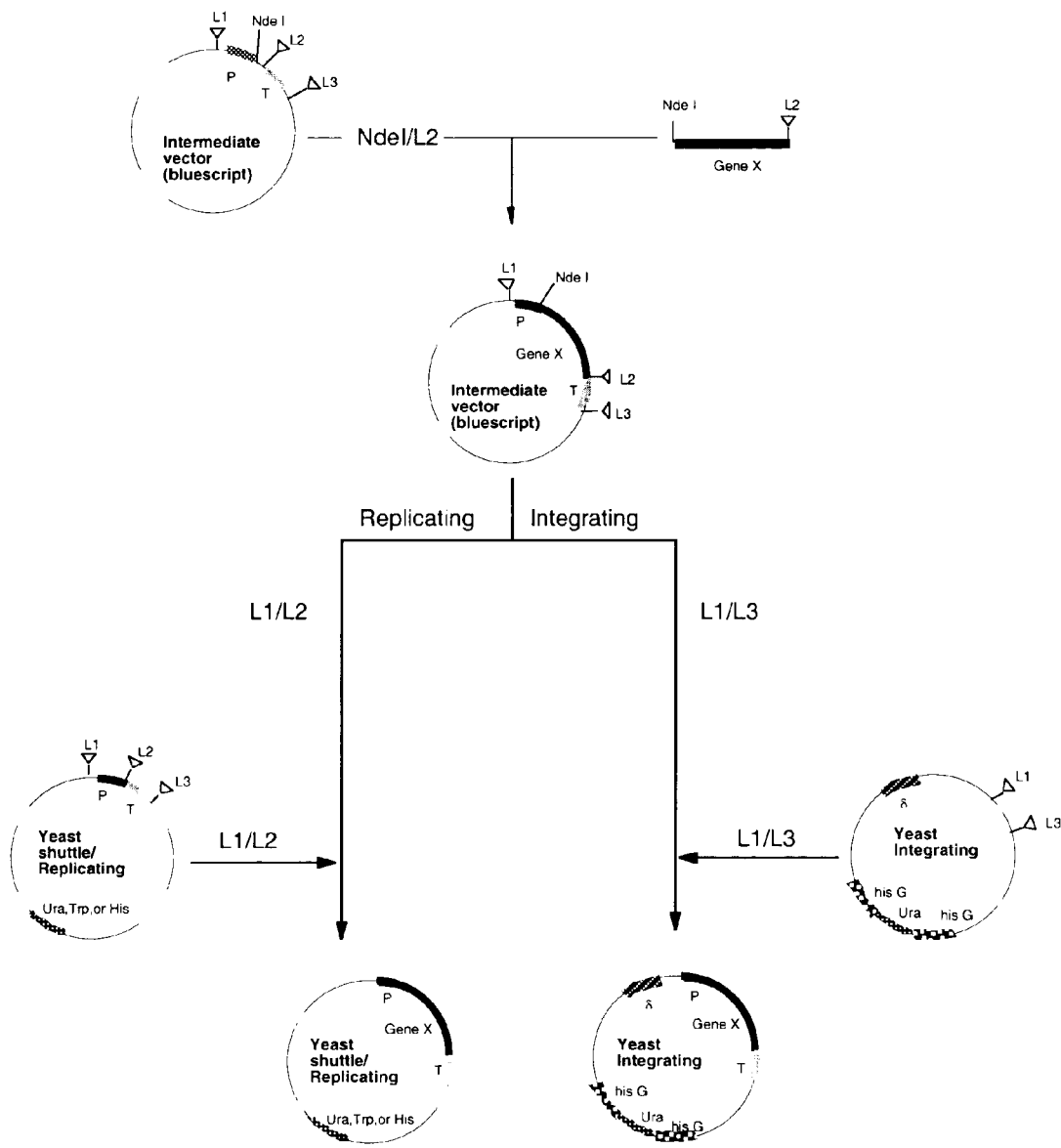
FIG. 9 shows a general method for cloning genes into yeast expression vectors.

The pccB and accA1 genes involved in the propionyl-CoA carboxylation pathway in *S. coelicolor* can be amplified by PCR from genomic DNA. As shown in FIG. 9, the genes can be cloned into the intermediate bluescript vector between Nde I and L2, then transferred to the yeast integrating vector via L1/L3. One can express the *S. coelicolor* genes shown to be effective in *E. coli*; should codon usage be suboptimal, one can employ the *B. subtilis* orthologs (discussed above).

FIG. 9 shows a general method for cloning genes into yeast expression vectors.

In one embodiment, the recombinant yeast host cells of the invention co-express the *B. subtilis* P-pant transferase, Sfp, with a PKS to convert the apo PKS to its holo form. The sfp gene is available on Bluescript™ (Stratagene) cloning and yeast shuttle/expression vectors and is functional in yeast (Kealey, J. T., et al., *Production of a polyketide natural product in nonpolyketide-producing prokaryotic and eukaryotic hosts*. Proc Natl Acad Sci USA, 1998. 95(2): p. 505–9; incorporated herein by reference), so one can simply construct stable strains expressing this gene. One to several copies (as determined optimal) of the sfp gene can be introduced into delta sequences in the yeast chromosome as described above. One can test the activity of the integrated sfp gene by co-expressing 6-MSAS on a replicating vector, by measuring the Sfp-dependent 6-MSA production (Kealey, J. T., et al., *Production of a polyketide natural product in nonpolyketide-producing prokaryotic and eukaryotic hosts*. Proc Natl Acad Sci USA, 1998. 95(2): p. 505–9; incorporated herein by reference), and by quantifying the incorporation of [3H] β-alanine into the ACP domain of the PKS (see below). This allows one to determine the optimal number of copies of the sfp gene needed for maximal polyketide production.

The gene for the modular PKS, DEBS1+TE, is available as a NdeI-EcoRI fragment, which can be readily introduced into a yeast shuttle/expression vector as indicated in FIG. 9. Yeast strains expressing DEBS1+TE are analyzed for the [$^3$H]-phosphopantetheinylation of the PKS, and for production of triketide lactone by liquid chromatography/mass spectrometry.

3H labeling of intracellular Acyl-CoAs is carried out as follows. Cells are treated with [$^3$H] β-alanine (available at 50 Ci/mmol) in defined media lacking pantothenate, enabling the radioactive precursor of pantothenate to enter the CoA pool. Cells are then disrupted, CoA esters are separated by HPLC, and the radioactivity quantified by liquid scintillation counting, as described above.

*Saccharomyces cerevisiae* host cells are grown, and extracts prepared as follows. Defined minimal YNB media (1 mL) lacking pantothenate but containing 1 μM β-alanine are inoculated with a single colony of *S. cerevisiae* (InvSc1, or Fen2b deletion strain) from a YPD plate. The culture is grown to stationary phase and 10 μl of the stationary culture are used to inoculate the above media lacking β-alanine and pantothenate. The culture is incubated for 4 hours and 10 μl of the "starved" culture is used to inoculate media (1 mL) containing 10 μCi [$^3$H] β-alanine (50 Ci/mmol; 0.2 μM final β-alanine). After culture growth for appropriate times, the cells from a 1 mL culture are collected by centrifugation and washed with water. The cells are suspended in 200 μl of 10% cold trichloroacetic acid (TCA), containing standard unlabeled acyl-CoAs as chromatography markers (malonyl-, methylmalonyl-, succinyl-, acetyl-, propionyl-CoA, and CoA). The cells are disrupted by vortexing with glass beads, and the supernatent analyzed by HPLC.

HPLC is performed using a 150×4.6 mm 5μ ODS-3 INERTSIL HPLC column purchased from Metachem technology. HPLC buffer A is 100 mM sodium phosphate monobasic, 75 mM sodium acetate, pH 4.6 and buffer B is 70% buffer A, 30% methanol. The HPLC column is equilibrated at 10% buffer B at a flow rate of 1 mL/min. Following injection, a linear gradient to 40% buffer B is implemented over 35 minutes, followed by a linear gradient to 90% buffer B over 20 minutes. The gradient affords base-line separation of the standard acyl-CoAs. The eluant is monitored at 260 nm and fractions are collected and counted in a scintillation counter.

Determination of the specific activity of the total CoA pool is carried out as follows. *S. cerevisiae* cultures are labeled with 100 μCi of [$^3$H] β-alanine as described above. The yeast cells are disrupted and the extract is treated with 100 μM hydoxylamine, pH 8.5, to convert all acyl-CoAs to CoA. The labeled CoA is isolated by HPLC as described above and converted to acetyl-CoA with *E. coli* acetyl-CoA synthase (Sigma), using [$^{14}$C]-acetate as a substrate. The [$^3$H, $^{14}$C]-acetyl-CoA is separated by HPLC and the dual labels quantified by scintillation counting. The mmol CoA is determined by $^{14}$C, and specific activity of CoA determined from the 3H dpm per mmol CoA. The isotope dilution, reflecting endogenous production of β-alanine, is calculated by the specific activity of [$^3$H] CoA/specific activity [$^3$H] β-alanine used in the test.

Analysis of PKS expression levels is carried out as follows. Each ACP domain of each module of an active PKS is post-translationally modified with phosphopantetheine derived from CoA. Using yeast cells treated with [$^3$H] β-alanine (described above), one can label the PKS with high specific activity tritium. The protein will be separated on SDS-PAGE, eluted and radioactivity determined by liquid scintillation counting.

EXAMPLE 3

Conversion of Erythronolides to Erythromycins

A sample of a polyketide (~50 to 100 mg) is dissolved in 0.6 mL of ethanol and diluted to 3 mL with sterile water. This solution is used to overlay a three day old culture of *Saccharopolyspora erythraea* WHM34 (an eryA mutant) grown on a 100 mm R2YE agar plate at 30° C. After drying, the plate is incubated at 30° C. for four days. The agar is chopped and then extracted three times with 100 mL portions of 1% triethylamine in ethyl acetate. The extracts are combined and evaporated. The crude product is purified by preparative HPLC (C-18 reversed phase, water-acetonitrile gradient containing 1% acetic acid). Fractions are analyzed by mass spectrometry, and those containing pure compound are pooled, neutralized with triethylamine, and evaporated to a syrup. The syrup is dissolved in water and extracted three times with equal volumes of ethyl acetate. The organic extracts are combined, washed once with saturated aqueous NaHCO$_3$, dried over Na$_2$SO$_4$, filtered, and evaporated to yield ~0.15 mg of product. The product is a glycosylated and hydroxylated compound corresponding to erythromycin A, B, C, and D but differing therefrom as the compound provided differed from 6-dEB.

EXAMPLE 4

Measurement of Antibacterial Activity

Antibacterial activity is determined using either disk diffusion assays with *Bacillus cereus* as the test organism or by measurement of minimum inhibitory concentrations (MIC) in liquid culture against sensitive and resistant strains of *Staphylococcus pneumoniae*.

EXAMPLE 5

Evaluation of Antiparasitic Activity

Compounds can initially screened in vitro using cultures of *P. falciparum* FCR-3 and KI strains, then in vivo using mice infected with *P. berghei*. Mammalian cell toxicity can be determined in FM3A or KB cells. Compounds can also be screened for activity against *P. berhei*. Compounds are also tested in animal studies and clinical trials to test the antiparasitic activity broadly (antimalarial, trypanosomiasis and Leishmaniasis).

The invention having now been described by way of written description and example, those of skill in the art will recognize that the invention can be practiced in a variety of embodiments and that the foregoing description and examples are for purposes of illustration and not limitation of the following claims.

The invention claimed is:

1. An *E. coli* host cell that expresses
a) methylmalonyl CoA mutase genes mutA and mutB from either *Propionibacterium shermanii* or *Streptomyces cinnamonensis*,
b) the epimerase gene from *Propionibacterium shermanii* having the nucleotide sequence given in SEQ ID NO: 1, and
c) at least one modular polyketide synthase (PKS) gene, wherein said PKS gene or genes are contained in a vector that replicates extrachromosomally or is integrated into chromosomal DNA.

2. The host cell of claim 1, wherein said methylmalonyl CoA mutase genes are the *Propionibacterium shermanii* methylmalonyl CoA mutase genes mutA and mutB.

3. The host cell of claim 1, wherein said methylmalonyl CoA mutase genes are the *Streptomyces cinnamonensis* methylmalonyl CoA mutase genes mutA and mutB.

4. The host cell of claim 1, wherein one or more of said genes is under control of a promoter from an *E. coli* gene.

5. The host cell of claim 1, wherein said PKS is 6-deoxyerythronolide B synthase.

6. A recombinant *E. coli* host cell comprising one or more expression vectors, said expression vectors comprising alone or in combination:
a) methylmalonyl CoA mutase genes mutA and mutB from either *Propionibacterium shermanii* or *Streptomyces cinnamonensis*,
b) the epimerase gene from *Propionibacterium shermanii* having the nucleotide sequence given in SEQ ID NO: 1, and
c) at least one modular polyketide synthase (PKS) gene, wherein the proteins encoded by said methylmalonyl CoA mutase and epimerase genes are effective to produce S-methylmalonyl CoA, which is a substrate required for biosynthesis of a polyketide produced by said modular PKS produced,
said PKS gene being contained in a vector that replicates extrachromosomally or is integrated into chromosomal DNA of such host cell, wherein said host cell, in the absence of said expression vectors, is unable to make said polyketide.

7. The host cell of claim 6, wherein said methylmalonyl CoA mutase genes are the *Propionibacterium shermanii* methylmalonyl CoA mutase genes mutA and mutB.

8. The host cell of claim 6, wherein said methylmalonyl CoA mutase genes are the *Streptomyces cinnamonensis* methylmalonyl CoA mutase genes mutA and mutB.

9. The host cell of claim 6, wherein one or more of said genes is under control of a promoter from an *E. coli* gene.

10. The host cell of claim 6, wherein said PKS is 6-deoxyerythronolide B synthase.

11. The host cell of claim 6 that comprises two expression vectors, one of which is integrated into chromosomal DNA of said cell.

12. The host cell of claim 6 that comprises two expression vectors, one of which is a plasmid.

13. The host cell of claim 6 in media that contains hydroxocobalamin.

14. The host cell of claim 13, wherein said methylmalonyl CoA mutase genes are the *Propionibacterium shermanii* methylmalonyl CoA mutase genes mutA and mutB.

15. The host cell of claim 13, wherein said methylmalonyl CoA mutase genes are the *Streptomyces cinnamonensis* methylmalonyl CoA mutase genes mutA and mutB.

16. The host cell of claim 13, wherein one or more of said genes is under control of a promoter from an *E. coli* gene or a gene.

17. The host cell of claim 13, wherein said PKS is 6-deoxyerythronolide B synthase.

18. A method for producing a polyketide, which method comprises culturing the host cell of claim 1 or 6 under conditions such that
said PKS gene is expressed to produce a functional PKS,
said methylmalonyl CoA is produced and
said functional PKS synthesizes a polyketide that incorporates said S-methylmalonyl CoA.

19. The method of claim 18, wherein the host cell is cultured in a medium that contains hydroxocobalamin.

* * * * *

SEQUENCE LISTING

<160> NUMBER OF SEQ ID NOS: 2

<210> SEQ ID NO 1
<211> LENGTH: 447
<212> TYPE: DNA
<213> ORGANISM: Artificial Sequence
<220> FEATURE:
<223> OTHER INFORMATION: Isolated and recombinant form of the full
      epimerase gene sequence
<220> FEATURE:
<221> NAME/KEY: CDS
<222> LOCATION: (1)...(444)

<400> SEQUENCE: 1

```
atg agt aat gag gat ctt ttc atc tgt atc gat cac gtg gca tat gcg      48
Met Ser Asn Glu Asp Leu Phe Ile Cys Ile Asp His Val Ala Tyr Ala
 1               5                  10                  15 tgc ccc gac gcc gac gag gct tcc aag tac tac cag gag acc ttc ggc      96
Cys Pro Asp Ala Asp Glu Ala Ser Lys Tyr Tyr Gln Glu Thr Phe Gly
                 20                  25                  30 tgg cat gag ctc cac cgc gag gag aac ccg gag cag gga gtc gtc gag     144
Trp His Glu Leu His Arg Glu Glu Asn Pro Glu Gln Gly Val Val Glu
             35                  40                  45 atc atg atg gcc ccg gct gcg aag ctg acc gag cac atg acc cag gtt     192
Ile Met Met Ala Pro Ala Ala Lys Leu Thr Glu His Met Thr Gln Val
         50                  55                  60 cag gtc atg gcc ccg ctc aac gac gag tcg acc gtt gcc aag tgg ctt     240
Gln Val Met Ala Pro Leu Asn Asp Glu Ser Thr Val Ala Lys Trp Leu
 65                  70                  75                  80 gcc aag cac aat ggt cgc gcc gga ctg cac cac atg gca tgg cgt gtc     288
Ala Lys His Asn Gly Arg Ala Gly Leu His His Met Ala Trp Arg Val
                 85                  90                  95 gat gac atc gac gcc gtc agc gcc acc ctg cgc gag cgc ggc gtg cag     336
Asp Asp Ile Asp Ala Val Ser Ala Thr Leu Arg Glu Arg Gly Val Gln
                100                 105                 110 ctg ctg tat gac gag ccc aag ctc ggc acc ggc ggc aac cgc atc aac     384
Leu Leu Tyr Asp Glu Pro Lys Leu Gly Thr Gly Gly Asn Arg Ile Asn
             115                 120                 125 ttc atg cat ccc aag tcg ggc aag ggc gtg ctc atc gag ctc acc cag     432
Phe Met His Pro Lys Ser Gly Lys Gly Val Leu Ile Glu Leu Thr Gln
         130                 135                 140 tac ccg aag aac tga                                                 447
Tyr Pro Lys Asn
145
```

<210> SEQ ID NO 2
<211> LENGTH: 148
<212> TYPE: PRT
<213> ORGANISM: Artificial Sequence
<220> FEATURE:
<223> OTHER INFORMATION: Deduced amino acid sequence of the epimerase
      gene sequence

<400> SEQUENCE: 2

```
Met Ser Asn Glu Asp Leu Phe Ile Cys Ile Asp His Val Ala Tyr Ala
 1               5                  10                  15

Cys Pro Asp Ala Asp Glu Ala Ser Lys Tyr Tyr Gln Glu Thr Phe Gly
                 20                  25                  30

Trp His Glu Leu His Arg Glu Glu Asn Pro Glu Gln Gly Val Val Glu
             35                  40                  45

Ile Met Met Ala Pro Ala Ala Lys Leu Thr Glu His Met Thr Gln Val
```

-continued

```
                50                    55                    60

Gln Val Met Ala Pro Leu Asn Asp Glu Ser Thr Val Ala Lys Trp Leu
 65              70                   75                    80

Ala Lys His Asn Gly Arg Ala Gly Leu His His Met Ala Trp Arg Val
                 85                  90                95

Asp Asp Ile Asp Ala Val Ser Ala Thr Leu Arg Glu Arg Gly Val Gln
                100             105                 110

Leu Leu Tyr Asp Glu Pro Lys Leu Gly Thr Gly Gly Asn Arg Ile Asn
            115             120                 125

Phe Met His Pro Lys Ser Gly Lys Gly Val Leu Ile Glu Leu Thr Gln
    130             135                 140

Tyr Pro Lys Asn
145
```